(12) United States Patent
Witherspoon et al.

(10) Patent No.: US 11,478,920 B2
(45) Date of Patent: *Oct. 25, 2022

(54) EXOSUIT SYSTEMS WITH LUMBAR AND CORE SUPPORT

(71) Applicant: SEISMIC HOLDINGS, INC., Menlo Park, CA (US)

(72) Inventors: Katherine Goss Witherspoon, Menlo Park, CA (US); Nicole Ida Kernbaum, Sunnyvale, CA (US); Hayley Stolee-Smith, Redwood City, CA (US); Richard Mahoney, Los Altos, CA (US)

(73) Assignee: Seismic Holdings, Inc., Menlo Park, CA (US)

( * ) Notice: Subject to any disclaimer, the term of this patent is extended or adjusted under 35 U.S.C. 154(b) by 891 days.

This patent is subject to a terminal disclaimer.

(21) Appl. No.: 16/356,191

(22) Filed: Mar. 18, 2019

(65) Prior Publication Data
US 2019/0283237 A1 Sep. 19, 2019

Related U.S. Application Data

(60) Provisional application No. 62/644,315, filed on Mar. 16, 2018.

(51) Int. Cl.
*A61F 2/70* (2006.01)
*B25J 9/00* (2006.01)
(Continued)

(52) U.S. Cl.
CPC ........... *B25J 9/0006* (2013.01); *A61B 5/1126* (2013.01); *A61B 5/6811* (2013.01);
(Continued)

(58) Field of Classification Search
CPC ... A61B 5/1126; A61B 5/6811; A61B 5/7267; A61B 5/375; A61B 2562/0219; A61B 5/6812; A61H 1/0237; A61H 1/0292; A61H 3/00; A61H 1/0274; A61H 2201/1616; A61H 2201/1638; A61H 2201/1621; A61H 2201/1642; A61H 2201/1626; A61H 1/02;
(Continued)

(56) References Cited

U.S. PATENT DOCUMENTS 9,266,233 B2  2/2016 Kornbluh et al.
10,926,123 B2 * 2/2021 Lear .................... A63B 24/0087
(Continued)

FOREIGN PATENT DOCUMENTS

WO  2016/138264 A1  9/2016

OTHER PUBLICATIONS

Xu et al., Research on Construction Techniques for System Transformation of Self-Anchored Suspension and Cable-Stayed Combination System Bridge, 2009, IEEE, p. 151-154 (Year: 2009).*

(Continued)

*Primary Examiner* — Mcdieunel Marc
(74) *Attorney, Agent, or Firm* — Van Court & Aldridge LLP

(57) ABSTRACT

Exosuits that use core grip members are described herein. Core grip members apply forces in a radially inward manner from the exterior of the body to the interior of the body to provide support to the user and to serve as a platform for mounting power layer segments.

20 Claims, 49 Drawing Sheets

(51) Int. Cl.
*A61H 3/00* (2006.01)
*A61B 5/00* (2006.01)
*B25J 13/08* (2006.01)
*B25J 9/16* (2006.01)
*A61B 5/11* (2006.01)
*A63B 21/00* (2006.01)
*A61H 1/02* (2006.01)
*A61B 5/375* (2021.01)

(52) U.S. Cl.
CPC .............. *A61B 5/7267* (2013.01); *A61F 2/70* (2013.01); *A61H 3/00* (2013.01); *B25J 9/1633* (2013.01); *B25J 13/085* (2013.01); *A61B 5/375* (2021.01); *A61B 5/6812* (2013.01); *A61B 2562/0219* (2013.01); *A61H 1/02* (2013.01); *A61H 2201/1602* (2013.01); *A63B 21/4039* (2015.10); *A63B 2220/803* (2013.01); *A63B 2225/50* (2013.01); *B25J 9/1615* (2013.01)

(58) Field of Classification Search
CPC .... A61H 2201/0221; A61H 2201/0207; A61H 2201/163; A61H 2201/1602; A61H 2201/165; B25J 13/085; B25J 9/0006; B25J 9/1633; B25J 9/1615; A61F 2/70; A63B 21/4039; A63B 2220/803; A63B 2225/50

See application file for complete search history.

(56) References Cited

U.S. PATENT DOCUMENTS

| | | | |
|---|---|---|---|
| 11,192,237 B2 * | 12/2021 | Mahoney | A61F 2/68 |
| 2018/0056104 A1 * | 3/2018 | Cromie | A61H 3/00 |
| 2019/0160651 A1 * | 5/2019 | Mahoney | B25J 9/0006 |
| 2019/0160652 A1 * | 5/2019 | Mahoney | B25J 9/0006 |
| 2020/0223071 A1 * | 7/2020 | Mahoney | A61H 1/00 |
| 2021/0007874 A1 * | 1/2021 | Galiana Bujanda | A61F 5/028 |
| 2022/0040025 A1 * | 2/2022 | Yoshimi | A61H 1/0274 |
| 2022/0047004 A1 * | 2/2022 | Betts | A41D 13/0015 |
| 2022/0062090 A1 * | 3/2022 | Chisolm | A61H 23/02 |
| 2022/0079792 A1 * | 3/2022 | Lear | A61F 5/0102 |

OTHER PUBLICATIONS

Doyle et al., An Avian-Inspired Passive Mechanism for Quadrotor Perching, 2013, IEEE, p. 506-517 (Year: 2013).*
Asbeck et al., Stronger, Smarter, Softer: Next-Generation Wearable Robots, 2014, IEEE, p. 23-33 (Year: 2014).*

* cited by examiner

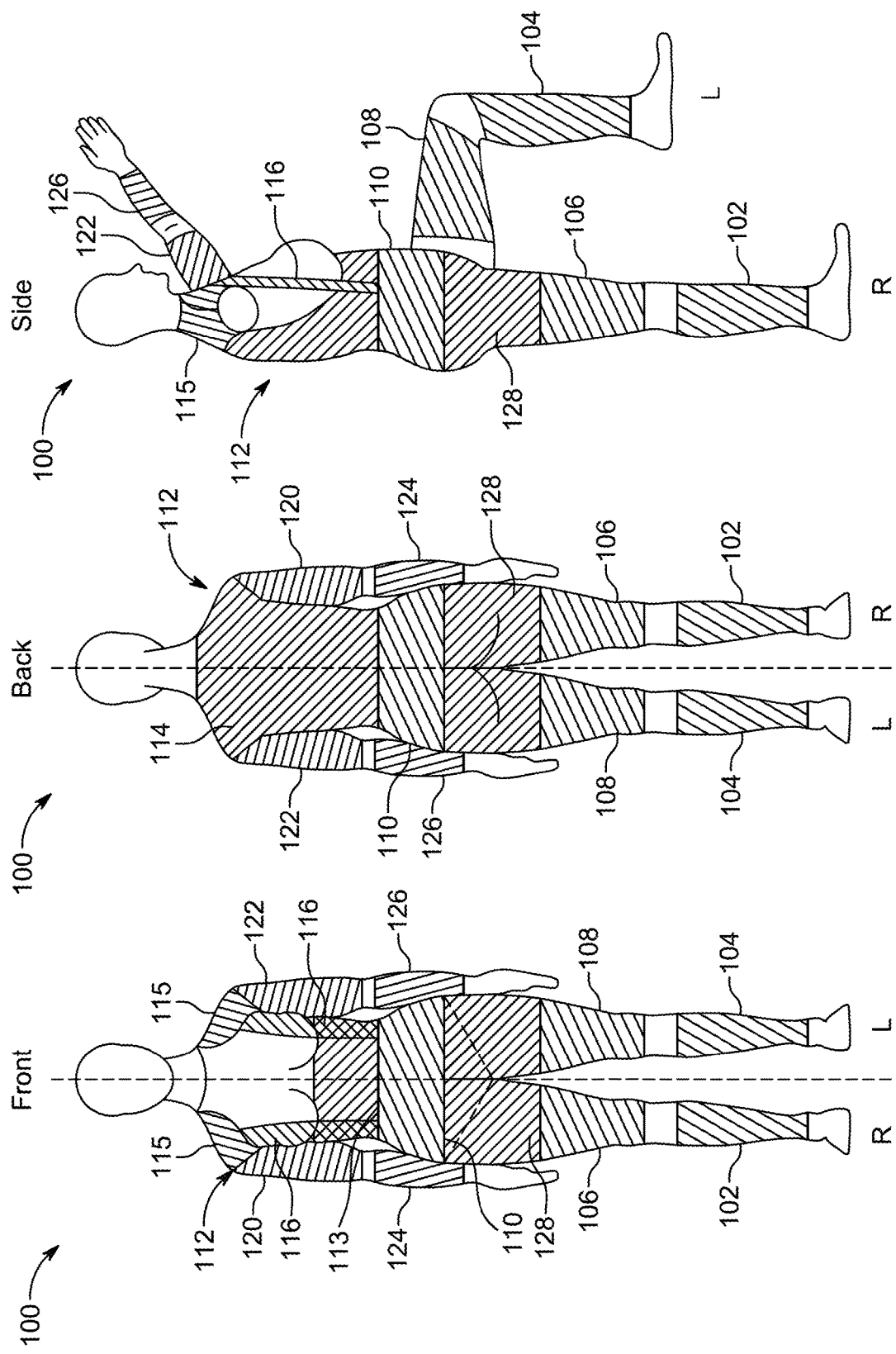

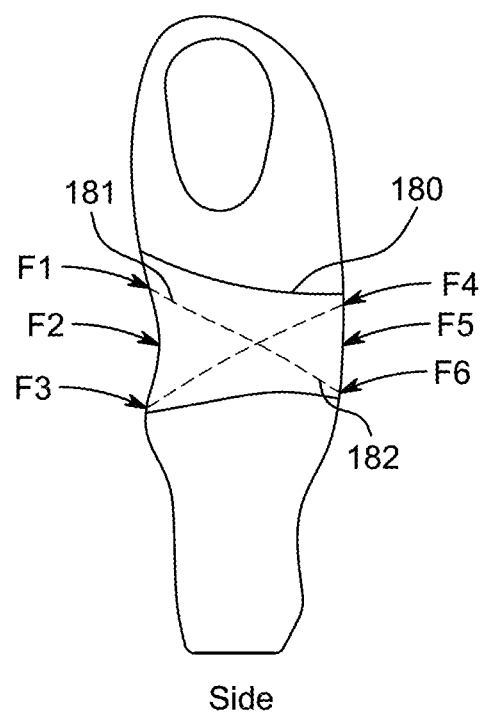
Side
FIG. 1K
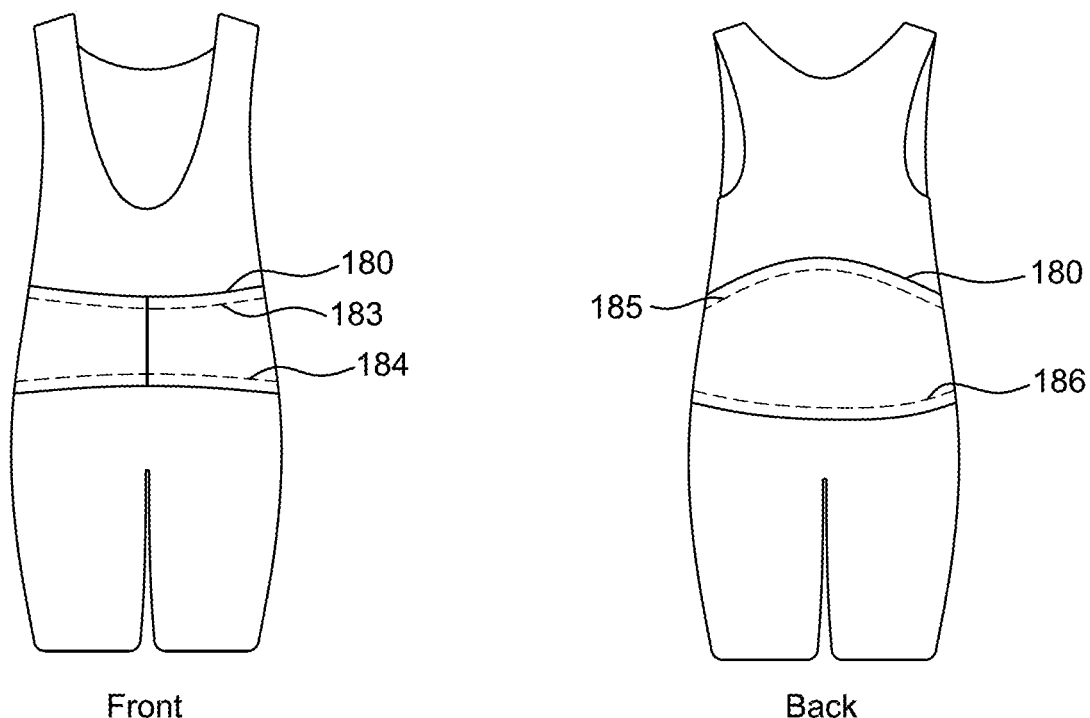
Front
FIG. 1L
Back
FIG. 1M

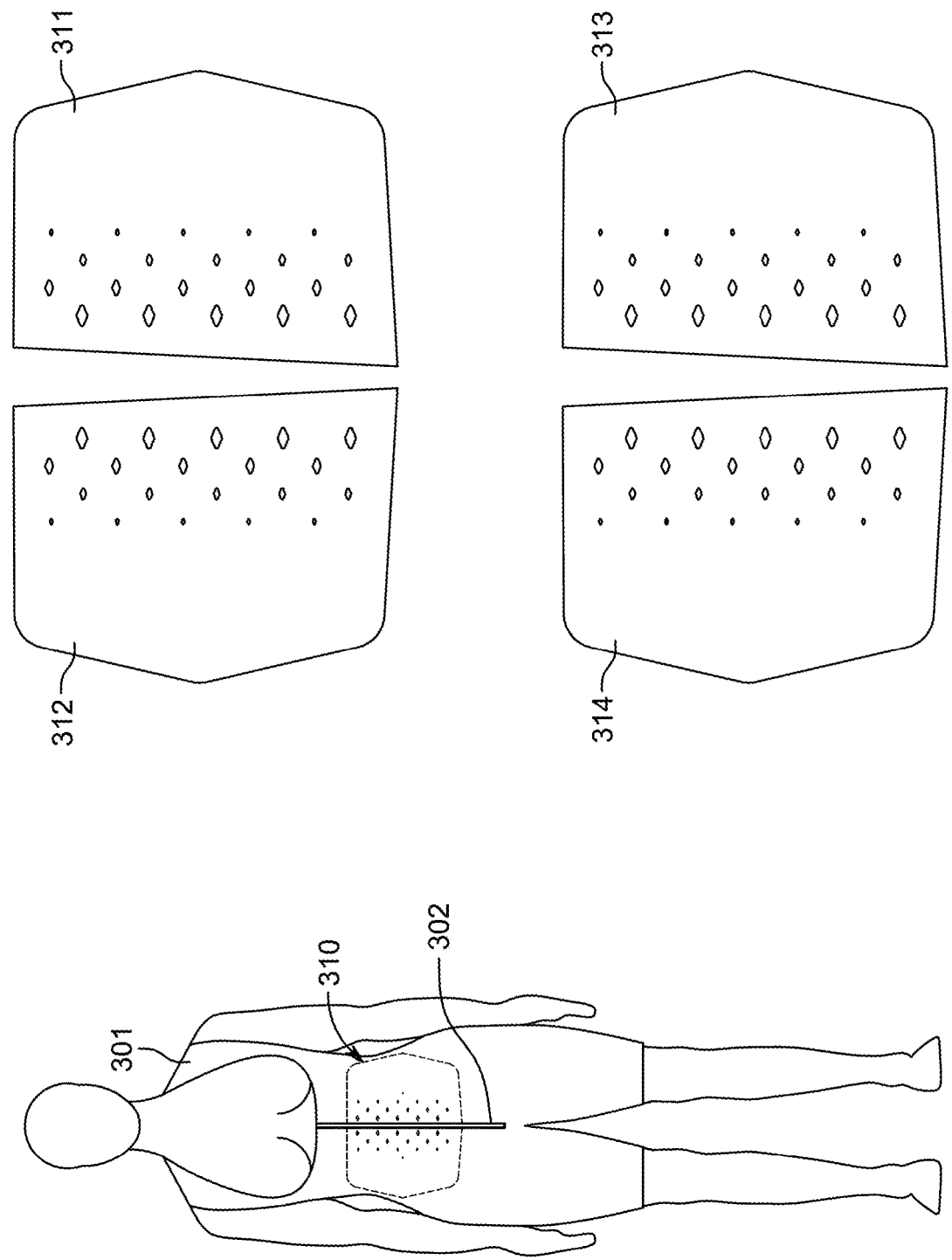

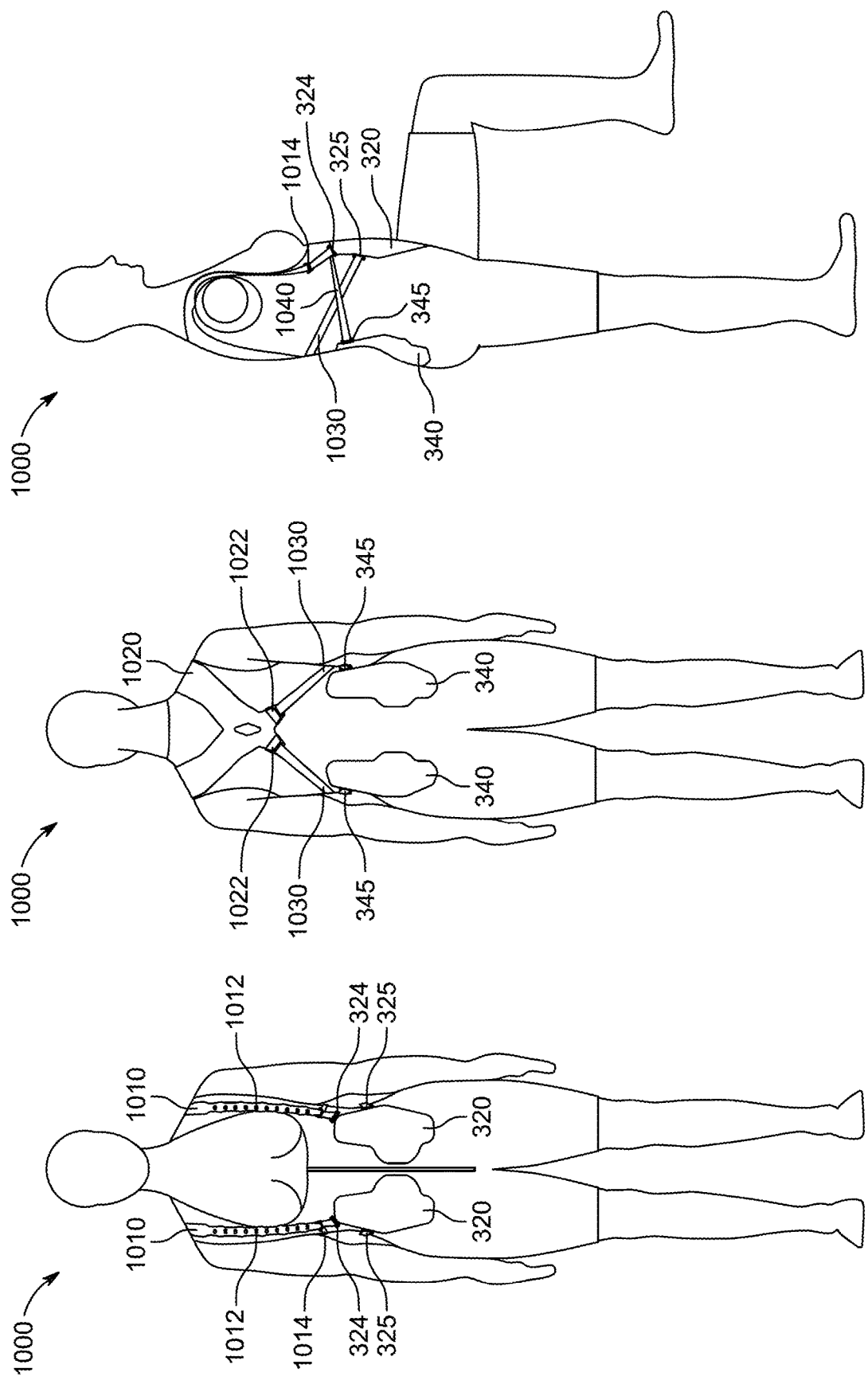

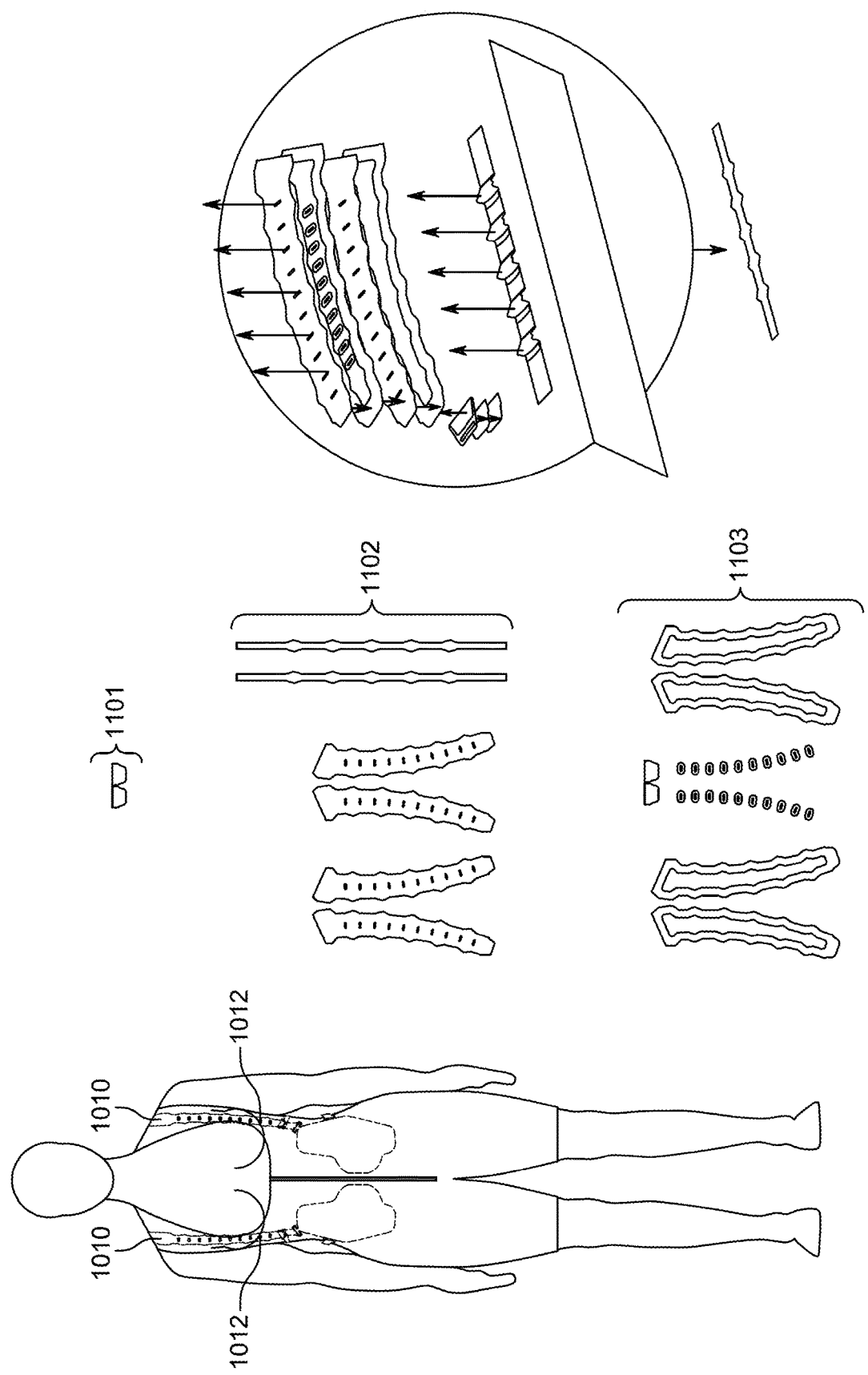

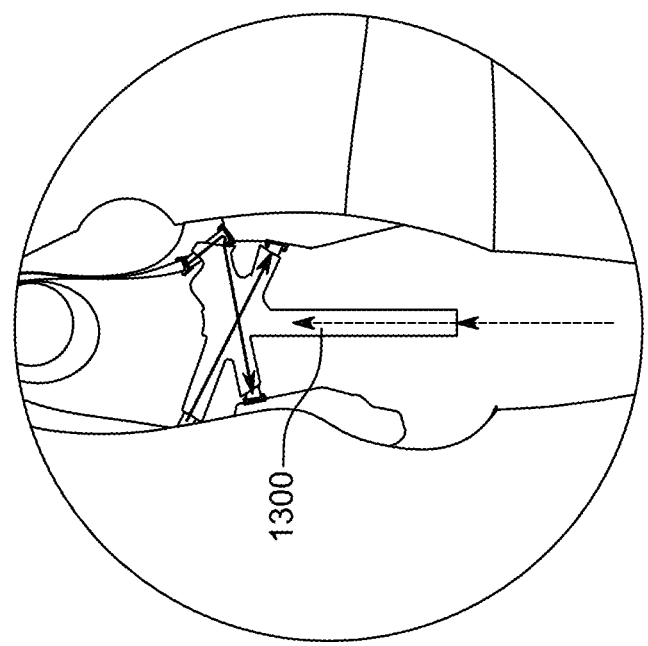
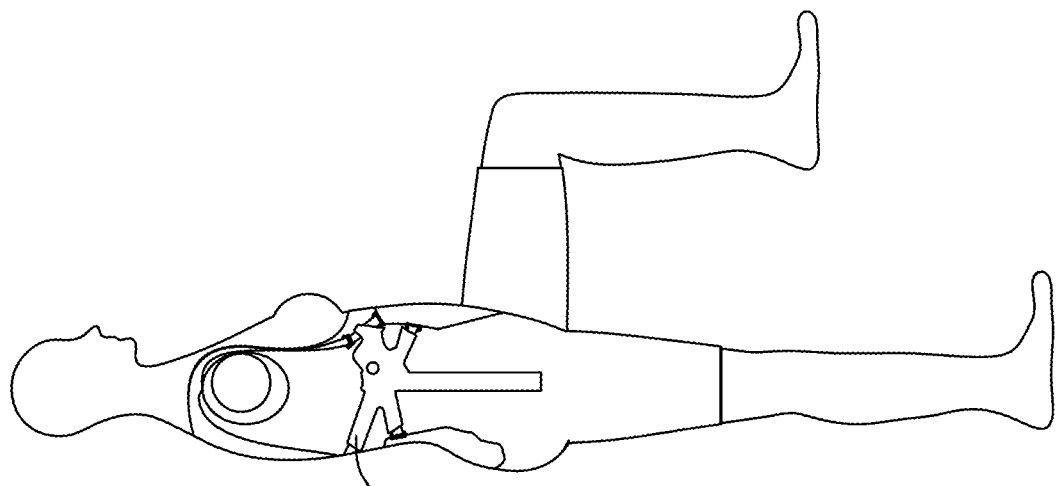
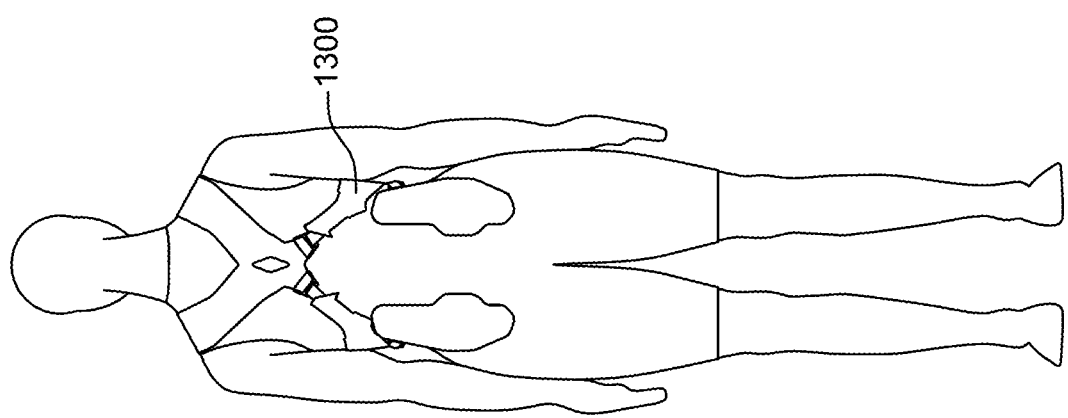
FIG. 13C
FIG. 13B
FIG. 13A

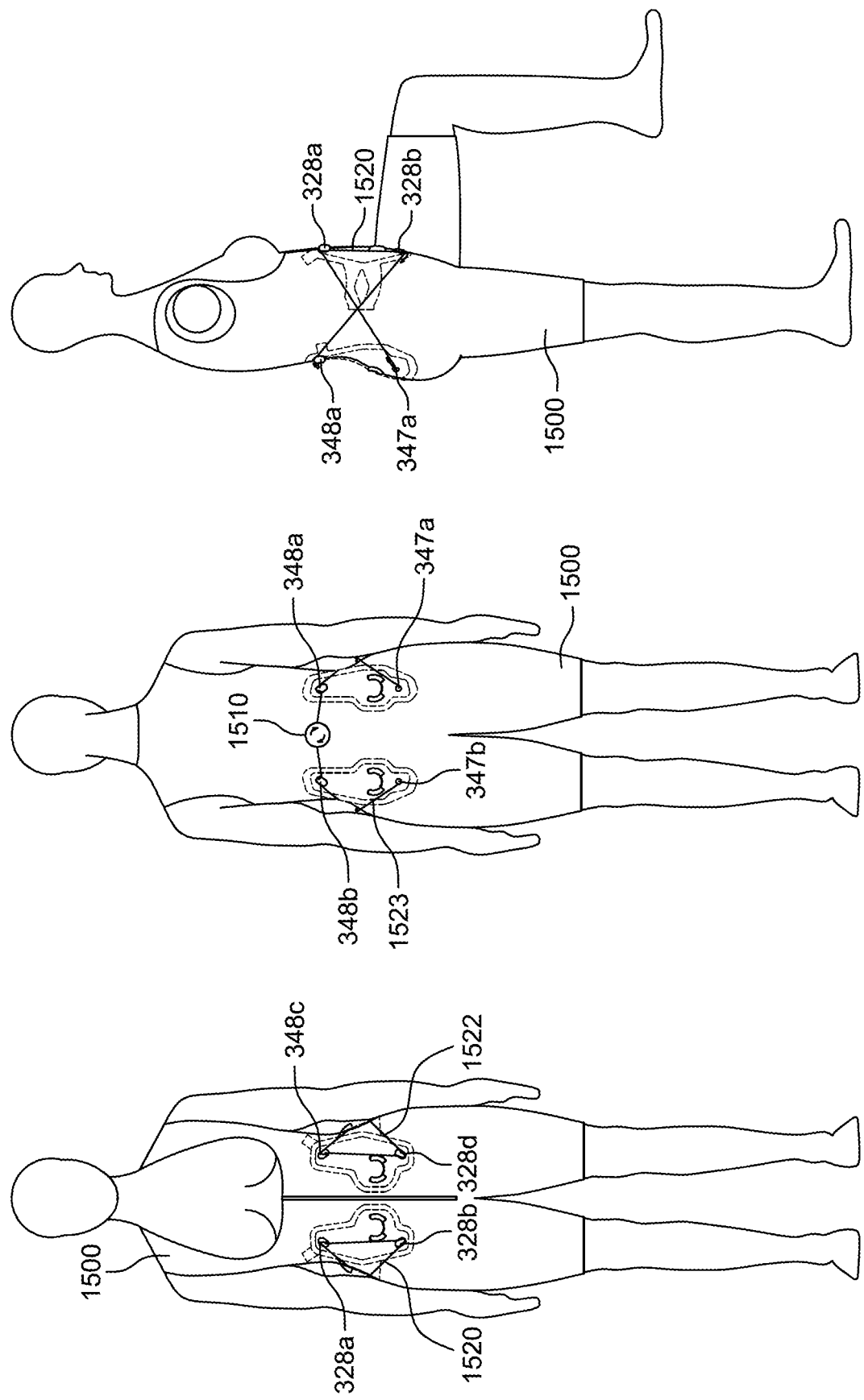

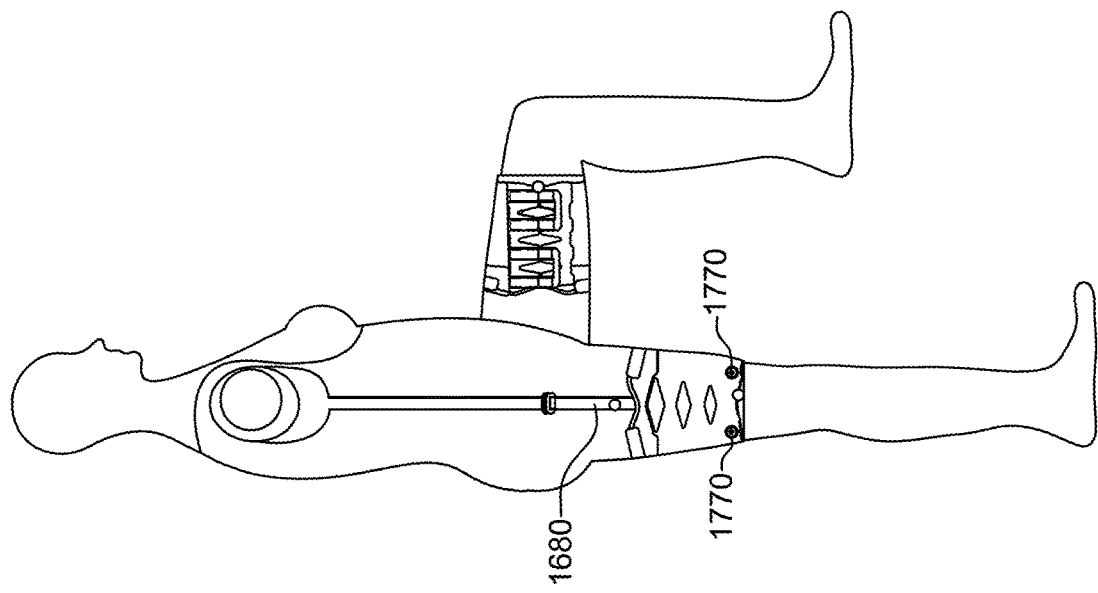
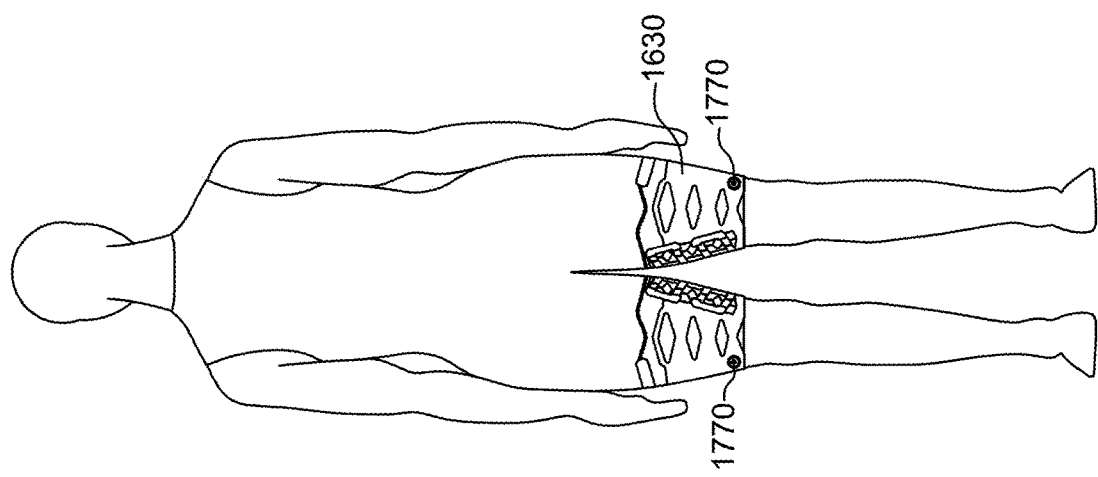
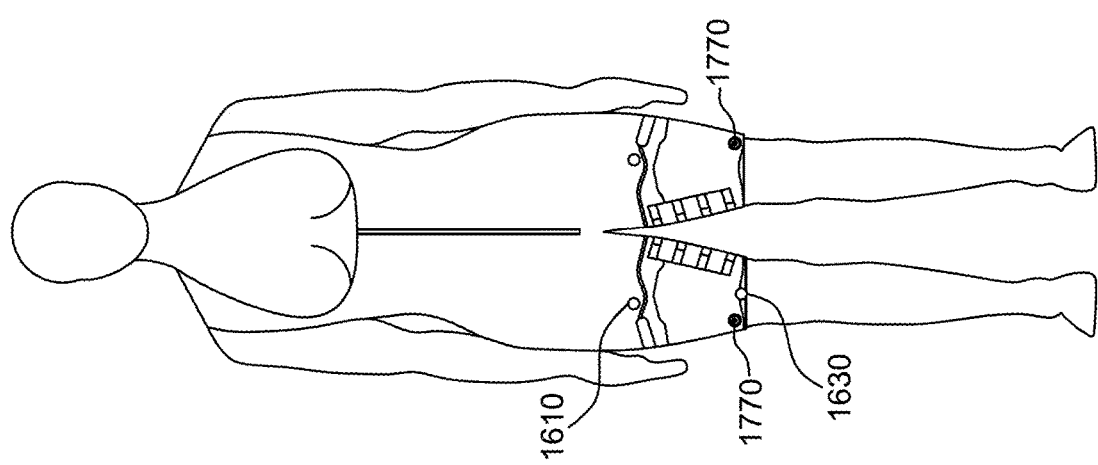
FIG. 16C
FIG. 16B
FIG. 16A

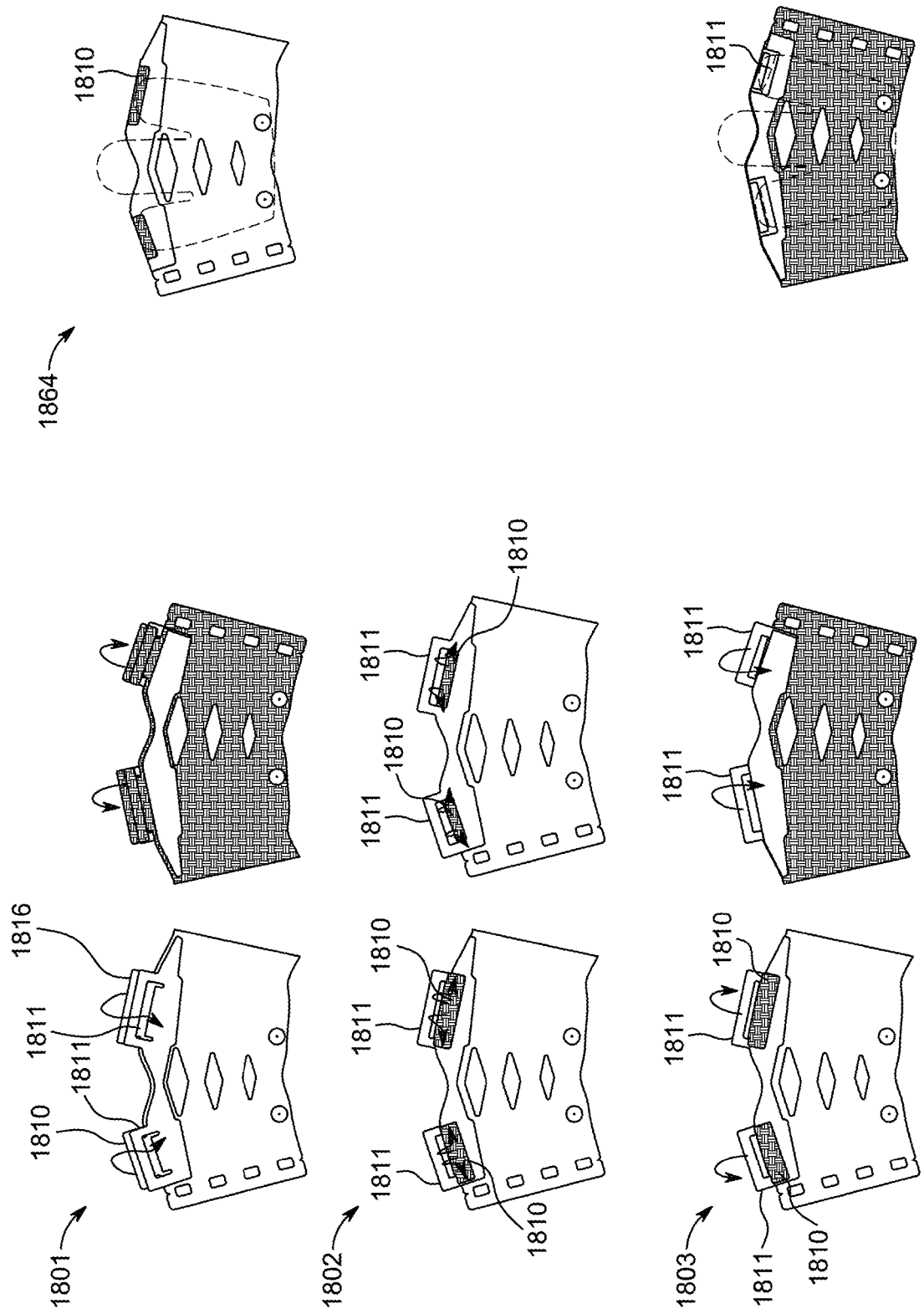

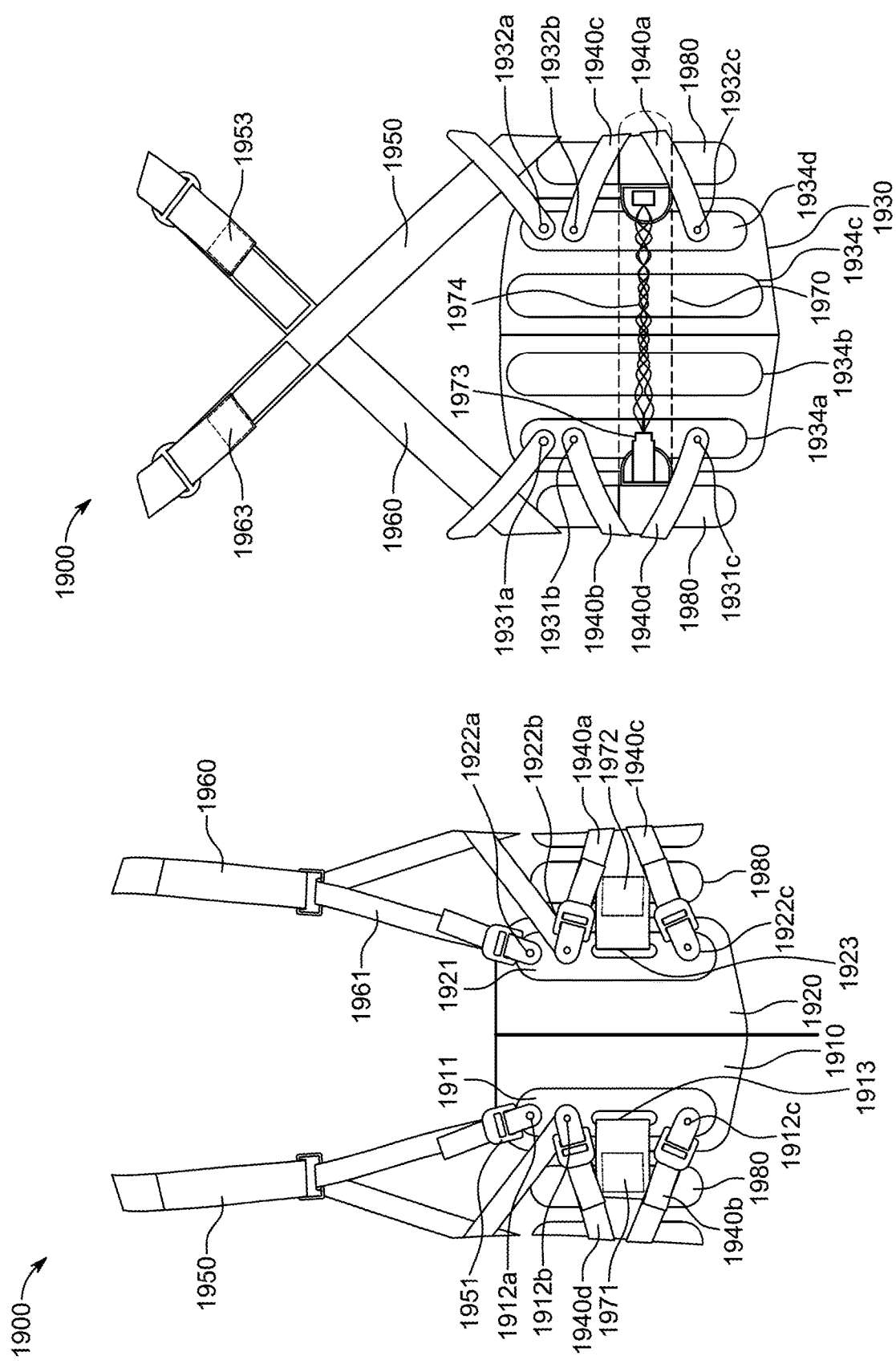

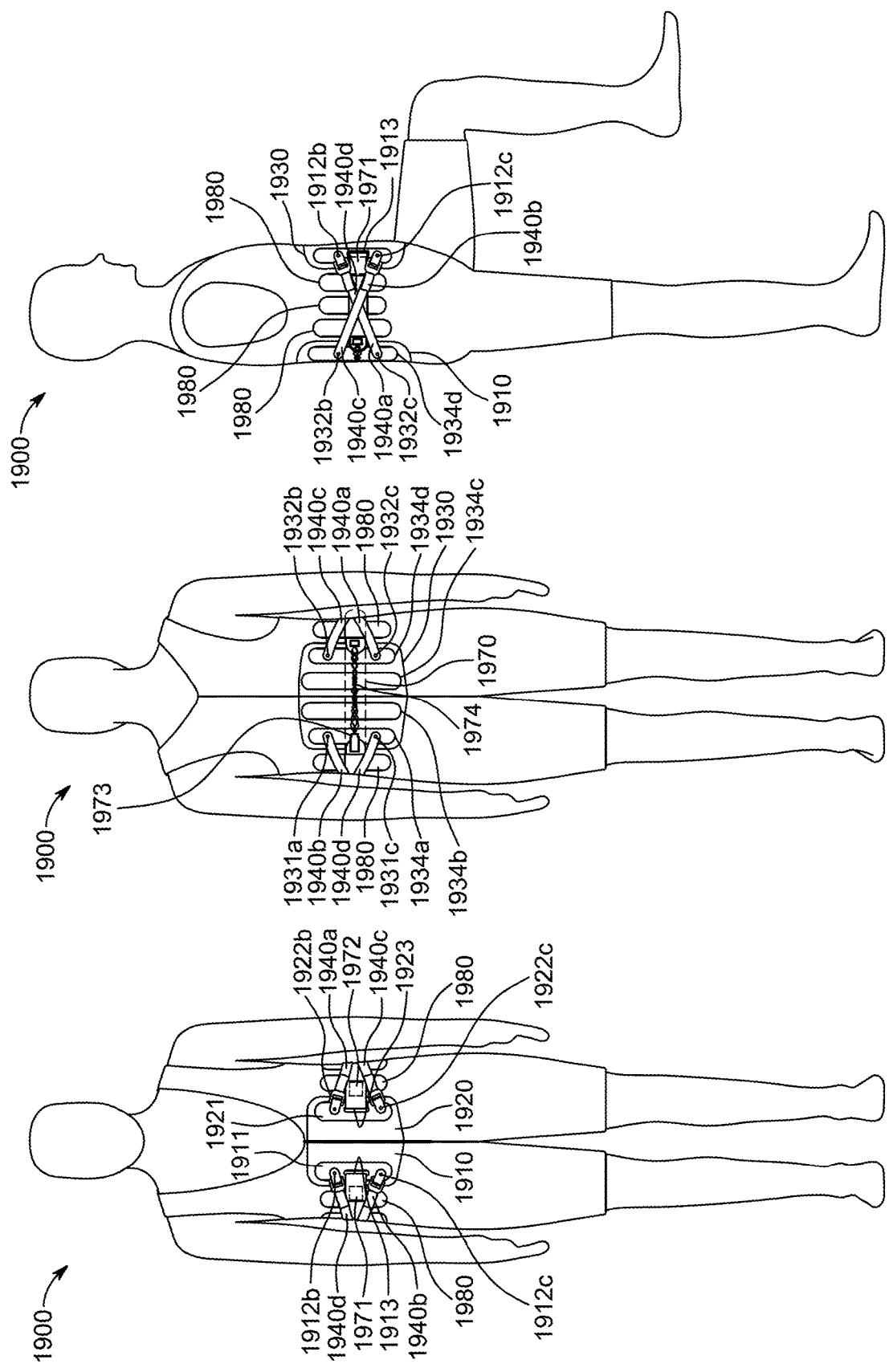

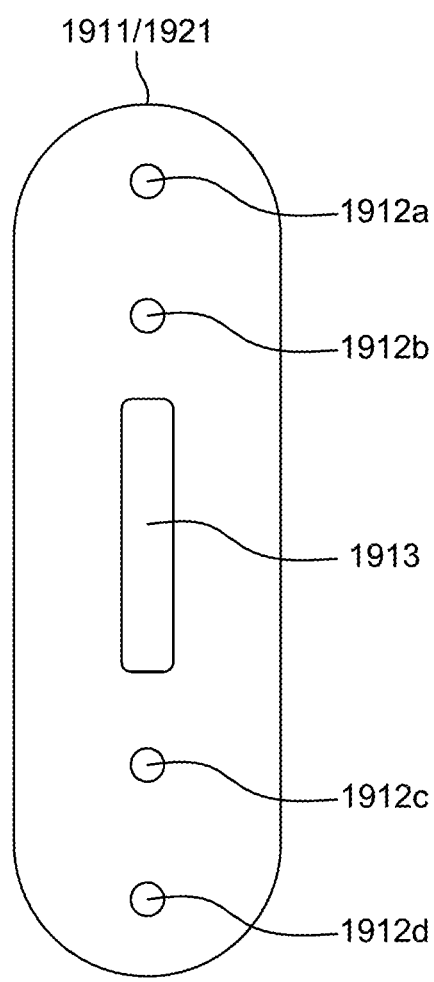
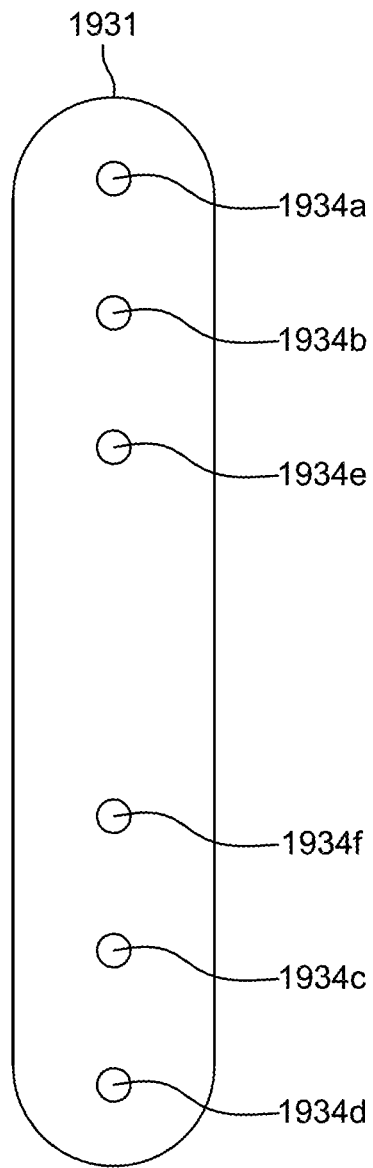
FIG. 22
FIG. 23

EXOSUIT SYSTEMS WITH LUMBAR AND CORE SUPPORT

CROSS-REFERENCE TO RELATED APPLICATIONS

This application claims priority to U.S. Provisional Patent Application No. 62/644,315, filed Mar. 16, 2018, the disclosure of which is incorporated by reference in its entirety.

BACKGROUND

Wearable robotic systems have been developed for augmentation of humans' natural capabilities, or to replace functionality lost due to injury or illness.

SUMMARY

Exosuits that use core grip members are described herein. Core grip members apply forces in a radially inward manner from the exterior of the body to the interior of the body to provide support to the user and to serve as a platform for mounting power layer segments.

In one embodiment, an exosuit is provide that can include a core support grip that is positioned around a core of a human body. The core support grip can include first and second front main stays positioned on an anterior side of the human body, each the first and second main stays comprising a rigid portion and a plurality of ports; and first and second back main stays positioned on a posterior side of the human body, each of the first and second back main stays comprising a rigid portion, a port, and an anchor point. The exosuit can include a tension system connected to the core support grip, the tension system including adjustment member, a first cord that is routed from the adjustment member through the plurality of ports associated with the first front main stay, the port associated with the first back main stay, and secured to the anchor point associated with the with the first back main stay, and a second cord that is routed from the adjustment member through the plurality of ports associated with the second front main stay, the port associated with the second back main stay, and secured to the anchor point associated with the with the second back main stay, wherein the adjustment member is operative to adjust tension applied by the first and second cords to increase or decrease forces applied to the core.

In another embodiment, an exosuit is provided that includes a core support grip that is positioned around a core of a human body, the core support grip including first and second front panels positioned on an anterior side of the human body, each of the first and second front panels comprising a vertical stay, and a back panel positioned on a posterior side of the human body, the back panel comprising a plurality of vertical stays; and a tension system connected to the core support grip and operative to increase or decrease pressure applied to the core by the cores support grip.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIGS. 1A-1C show front, back, and side views of a base layer of an exosuit according to an embodiment;

FIGS. 1K-1M shows illustrative side, front, and back views of core/lumber load distribution member according to an embodiment;

FIGS. 4A-4C show different views of a front sub-stay according to various embodiments;

FIGS. 10A-10C show illustrative front, back, and side view of a shoulder system according to an embodiment;

FIGS. 11A-11C show different views of the front of a shoulder system according to an embodiment;

FIGS. 13A-13C show different illustrative views of a tunnel system according to an embodiment;

FIGS. 15A-15C show illustrative front, back, and side views of a cord system according to an embodiment;

FIGS. 16A-16C show illustrative front, back, and side views of thigh grip members according to an embodiment;

FIG. 18 shows steps for forming thigh grip pockets according to an embodiment;

FIGS. 19A and 19B show front and back views of a core support grip according to an embodiment;

FIGS. 20A-20C show the core support grip of FIGS. 19A and 19B, but with shoulder various components removed, according to an embodiment;

FIG. 20C shows side stays according to an embodiment;

FIG. 22 shows an illustrative front stay according to an embodiment;

FIG. 23 shows an illustrative back stay according to an embodiment;

DETAILED DESCRIPTION

Figures 1D, 1E, 1F:
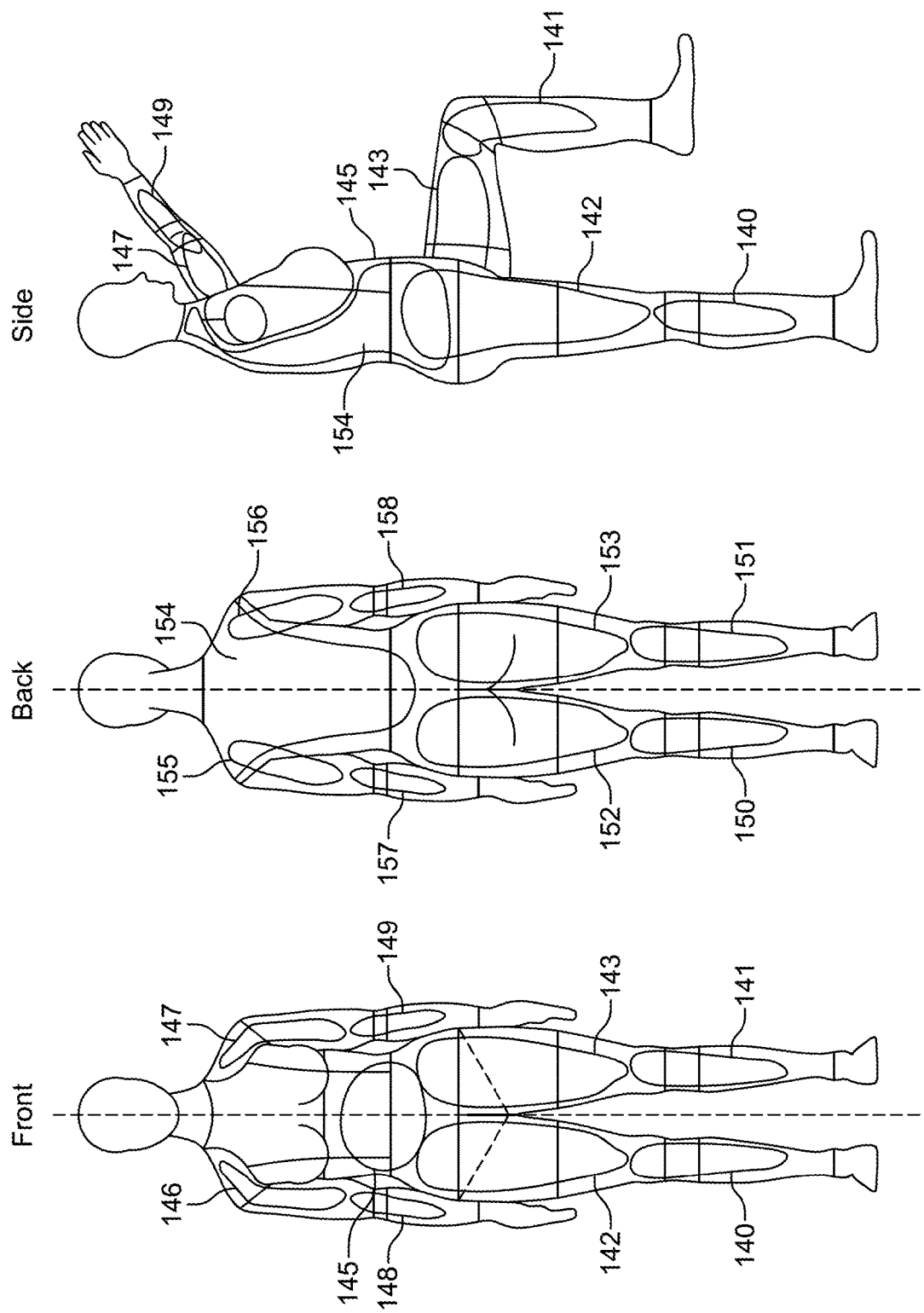
FIGS. 1D-1F show front, back, and side views, respectively, of a power layer according to an embodiment.

In the following description, numerous specific details are set forth regarding the systems, methods and media of the disclosed subject matter and the environment in which such systems, methods and media may operate, etc., in order to provide a thorough understanding of the disclosed subject matter. It can be apparent to one skilled in the art, however, that the disclosed subject matter may be practiced without such specific details, and that certain features, which are well known in the art, are not described in detail in order to avoid complication of the disclosed subject matter. In addition, it can be understood that the examples provided below are exemplary, and that it is contemplated that there are other systems, methods and media that are within the scope of the disclosed subject matter.

In the descriptions that follow, an exosuit or assistive exosuit is a suit that is worn by a wearer on the outside of his or her body. It may be worn under the wearer's normal clothing, over their clothing, between layers of clothing, or may be the wearer's primary clothing itself. The exosuit may be supportive, assistive, resistive, and/or enhancing as it physically interacts with the wearer while performing particular activities, or can provide other functionality such as communication to the wearer through physical expressions to the body, engagement of the environment, or capturing of information from the wearer. In some embodiments, a powered exosuit system can include several subsystems, or layers. In some embodiments, the powered exosuit system can include more or less subsystems or layers. The subsystems or layers can include the base layer, stability layer, power layer, sensor and controls layer, a covering layer, and user interface/user experience (UI/UX) layer.

The base layer provides the interfaces between the exosuit system and the wearer's body. The base layer may be adapted to be worn directly against the wearer's skin, between undergarments and outer layers of clothing, over outer layers of clothing or a combination thereof, or the base layer may be designed to be worn as primary clothing itself. In some embodiments, the base layer can be adapted to be both comfortable and unobtrusive, as well as to comfortably and efficiently transmit loads from the stability layer and power layer to the wearer's body in order to provide the desired assistance. The base layer can typically comprise several different material types to achieve these purposes. Elastic materials may provide compliance to conform to the wearer's body and allow for ranges of movement. The innermost layer is typically adapted to grip the wearer's skin, undergarments or clothing so that the base layer does not slip as loads are applied. Substantially inextensible materials may be used to transfer loads from the stability layer and power layer to the wearer's body. These materials may be substantially inextensible in one axis, yet flexible or extensible in other axes such that the load transmission is along preferred paths. The load transmission paths may be optimized to distribute the loads across regions of the wearer's body to minimize the forces felt by the wearer, while providing efficient load transfer with minimal loss and not causing the base layer to slip. Collectively, this load transmission configuration within the base layer may be referred to as a load distribution member. Load distribution members refer to flexible elements that distribute loads across a region of the wearer's body. Examples of load distribution members can be found in International Application Publication No. WO 2016/138264, titled "Flexgrip," the contents of which are incorporated herein by reference.

The load distribution members may incorporate one or more load lines or catenary curves to distribute loads across the wearer's body. Multiple load distribution members or catenary curves may be joined with pivot points, such that as loads are applied to the structure, the arrangement of the load distribution members pivots tightens or constricts on the body to increase the gripping strength. Compressive elements such as battens, rods, or stays may be used to transfer loads to different areas of the base layer for comfort or structural purposes. For example, a power layer component may terminate in the middle back due to its size and orientation requirements, however the load distribution members that anchor the power layer component may reside on the lower back. In this case, one or more compressive elements may transfer the load from the power layer component at the middle back to the load distribution member at the lower back.

The load distribution members may be constructed using multiple fabrication and textile application techniques. For example, the load distribution member can be constructed from a layered woven 45°/90° with bonded edge, spandex tooth, organza (poly) woven 45°/90° with bonded edge, organza (cotton/silk) woven 45°/90°, and Tyvek (non-woven). The load distribution member may be constructed using knit and lacing or horse hair and spandex tooth. The load distribution member may be constructed using channels and/or laces.

The base layer may include a flexible underlayer that is constructed to compress against a portion of the wearer's body, either directly to the skin, or to a clothing layer, and also provides a relatively high grip surface for one or more load distribution members to attach thereto. The load distribution members can be coupled to the underlayer to facilitate transmission of shears or other forces from the members, via the flexible underlayer, to skin of a body segment or to clothing worn over the body segment, to maintain the trajectories of the members relative to such a body segment, or to provide some other functionality. Such a flexible underlayer could have a flexibility and/or compliance that differs from that of the member (e.g., that is less than that of the members, at least in a direction along the members), such that the member can transmit forces along their length and evenly distribute shear forces and/or pressures, via the flexible underlayer, to skin of a body segment to which a flexible body harness is mounted.

Further, such a flexible underlayer can be configured to provide additional functionality. The material of the flexible underlayer could include anti-bacterial, anti-fungal, or other agents (e.g., silver nanoparticles) to prevent the growth of microorganisms. The flexible underlayer can be configured to manage the transport of heat and/or moisture (e.g., sweat) from a wearer to improve the comfort and efficiency of activity of the wearer. The flexible underlayer can include straps, seams, hook-and-loop fasteners, clasps, zippers, or other elements configured to maintain a specified relationship between elements of the load distribution members and aspects of a wearer's anatomy. The underlayer can additionally increase the ease with which a wearer can don and/or doff the flexible body harness and/or a system (e.g., a flexible exosuit system) or garment that includes the flexible body harness. The underlayer can additionally be configured to protect the wearer from ballistic weapons, sharp edges, shrapnel, or other environmental hazards (by including, e.g., panels or flexible elements of para-aramid or other high-strength materials).

The base layer can additionally include features such as size adjustments, openings and electro-mechanical integration features to improve ease of use and comfort for the wearer.

Size adjustment features permit the exosuit to be adjusted to the wearer's body. The size adjustments may allow the suit to be tightened or loosened about the length or circumference of the torso or limbs. The adjustments may comprise lacing, the Boa system, webbing, elastic, hook-and-loop or other fasteners. Size adjustment may be accomplished by the load distribution members themselves, as they constrict onto the wearer when loaded. In one example, the torso circumference may be tightened with corset-style lacing, the legs tightened with hook-and-loop in a double-back configuration, and the length and shoulder height adjusted with webbing and tension-lock fasteners such as cam-locks, D-rings or the like. The size adjustment features in the base layer may be actuated by the power layer to dynamically adjust the base layer to the wearer's body in different positions, in order to maintain consistent pressure and comfort for the wearer. For example, the base layer may be required to tighten on the thighs when standing, and loosen when sitting such that the base layer does not excessively constrict the thighs when seated. The dynamic size adjustment may be controlled by the sensor and controls layer, for example by detecting pressures or forces in the base layer and actuating the power layer to consistently attain the desired force or pressure. This feature does not necessarily cause the suit to provide physical assistance, but can create a more comfortable experience for the wearer, or allow the physical assistance elements of the suit to perform better or differently depending on the purpose of the movement assistance.

Opening features in the base layer may be provided to facilitate donning (putting the exosuit on) and doffing (taking the exosuit off) for the wearer. Opening features may comprise zippers, hook-and-loop, snaps, buttons or other textile fasteners. In one example, a front, central zipper provides an opening feature for the torso, while hook-and-loop fasteners provide opening features for the legs and shoulders. In this case, the hook-and-loop fasteners provide both opening and adjustment features. In other examples, the exosuit may simply have large openings, for example around the arms or neck, and elastic panels that allow the suit to be donned and doffed without specific closure mechanisms. A truncated load distribution member may be simply extended to tighten on the wearer's body. Openings may be provided to facilitate toileting so the user can keep the exosuit on, but only have to remove or open a relatively small portion to use the bathroom.

Electro-mechanical integration features attach components of the stability layer, power layer and sensor and controls layer into the base layer for integration into the exosuit. The integration features may be for mechanical, structural, comfort, protective or cosmetic purposes. Structural integration features anchor components of the other layers to the base layer. For the stability and power layers, the structural integration features provide for load-transmission to the base layer and load distribution members, and may accommodate specific degrees of freedom at the attachment point. For example, a snap or rivet anchoring a stability or power layer element may provide both load transmission to the base layer, as well as a pivoting degree of freedom. Stitched, adhesive, or bonded anchors may provide load transmission with or without the pivoting degree of freedom. A sliding anchor, for example along a sleeve or rail, may provide a translational degree of freedom. Anchors may be separable, such as with snaps, buckles, magnets, clasps, hooks, or any other suitable closure mechanism; or may be inseparable, such as with stitching, adhesives or other bonding. Size adjustment features as described above may allow adjustment and customization of the stability and power layers, for example to adjust the tension of spring or elastic elements in the passive layer, or to adjust the length of actuators in the power layer.

Other integration features such as loops, pockets, and mounting hardware may simply provide attachment to components that do not have significant load transmission requirements, such as batteries, circuit boards, sensors, or cables. Components that exist as gravitation weight can be transmitted into support grips, for example, the load line on the outseam. In some cases, components may be directly integrated into textile components of the base layer. For example, cables or connectors may include conductive elements that are directly woven, bonded or otherwise integrated into the base layer.

Electromechanical integration features may also protect or cosmetically hide components of the stability, power or sensor and controls layers. Elements of the stability layer (e.g. elastic bands or springs), power layer (e.g. flexible linear actuators or twisted string actuators) or sensor and controls layer (e.g. cables) may travel through sleeves, tubes, or channels integrated into the base layer, which can both conceal and protect these components. The sleeves, tubes, or channels may also permit motion of the component, for example during actuation of a power layer element. The sleeves, channels, or tubes may comprise resistance to collapse, ensuring that the component remains free and uninhibited within.

Enclosures, padding, fabric coverings, or the like may be used to further integrate components of other layers into the base layer for cosmetic, comfort, thermal regulation, or protective purposes. For example, components such as motors, batteries, cables, or circuit boards may be housed within an enclosure, fully or partially covered or surrounded in padded material such that the components do not cause discomfort to the wearer, are visually unobtrusive and integrated into the exosuit, and are protected from the environment. Opening and closing features may additionally provide access to these components for service, removal, or replacement.

In some cases—particularly for exosuits configurable for either provisional use or testing—a tether may allow for some electronic and mechanical components to be housed off the suit. In one example, electronics such as circuit boards and batteries may be over-sized, to allow for added configurability or data capture. If the large size of these components makes it undesirable to mount them on the exosuit, they could be located separately from the suit and connected via a physical or wireless tether. Larger, over-powered motors may be attached to the suit via flexible drive linkages that allow actuation of the power layer without requiring large motors to be attached to the suit. Such over-powered configurations allow optimization of exosuit parameters without constraints requiring all components to be attached or integrated into the exosuit.

Electro-mechanical integration features may also include wireless communication. For example, one or more power layer components may be placed at different locations on the exosuit. Rather than utilizing physical electrical connections to the sensors and controls layer, the sensor and controls layer may communicate with the one or more power layer components via wireless communication protocols such as Bluetooth, ZigBee, ultrawide band, or any other suitable communication protocol. This may reduce the electrical interconnections required within the suit. Each of the one or more power layer components may additionally incorporate a local battery such that each power layer component or group of power layer components are independently powered units that do not require direct electrical interconnections to other areas of the exosuit.

The stability layer provides passive mechanical stability and assistance to the wearer. The stability layer comprises one or more passive (non-powered) spring or elastic elements that generate forces or store energy to provide stability or assistance to the wearer. An elastic element can have an un-deformed, least-energy state. Deformation, e.g. elongation, of the elastic element stores energy and generates a force oriented to return the elastic element toward its least-energy state. For example, elastic elements approximating hip flexors and hip extensors may provide stability to the wearer in a standing position. As the wearer deviates from the standing position, the elastic elements are deformed, generating forces that stabilize the wearer and assist maintaining the standing position. In another example, as a wearer moves from a standing to seated posture, energy is stored in one or more elastic elements, generating a restorative force to assist the wearer when moving from the seated to standing position. Similar passive, elastic elements may be adapted to the torso or other areas of the limbs to provide positional stability or assistance moving to a position where the elastic elements are in their least-energy state.

Elastic elements of the stability layer may be integrated to parts of the base layer or be an integral part of the base layer. For example elastic fabrics containing spandex or similar materials may serve as a combination base/stability layer. Elastic elements may also include discrete components such as springs or segments of elastic material such as silicone or elastic webbing, anchored to the base layer for load transmission at discrete points, as described above.

The stability layer may be adjusted as described above, both to adapt to the wearer's size and individual anatomy, as well as to achieve a desired amount of pre-tension or slack in components of the stability layer in specific positions. For example, some wearers may prefer more pre-tension to provide additional stability in the standing posture, while others may prefer more slack, so that the passive layer does not interfere with other activities such as ambulation.

The stability layer may interface with the power layer to engage, disengage, or adjust the tension or slack in one or more elastic elements. In one example, when the wearer is in a standing position, the power layer may pre-tension one or more elastic elements of the stability layer to a desired amount for maintaining stability in that position. The pre-tension may be further adjusted by the power layer for different positions or activities. In some embodiments, the elastic elements of the stability layer should be able to generate at least 5 lbs force; preferably at least 50 lbs force when elongated.

The power layer can provide active, powered assistance to the wearer, as well as electromechanical clutching to maintain components of the power or stability layers in a desired position or tension. The power layer can include one or more flexible linear actuators (FLA). An FLA is a powered actuator capable of generating a tensile force between two attachment points, over a give stroke length. An FLA is flexible, such that it can follow a contour, for example around a body surface, and therefore the forces at the attachment points are not necessarily aligned. In some embodiments, one or more FLAs can include one or more twisted string actuators. In the descriptions that follow, FLA refers to a flexible linear actuator that exerts a tensile force, contracts or shortens when actuated. The FLA may be used in conjunction with a mechanical clutch that locks the tension force generated by the FLA in place so that the FLA motor does not have to consume power to maintain the desired tension force. Examples of such mechanical clutches are discussed below. In some embodiments, FLAs can include one or more twisted string actuators or flexdrives, as described in further detail in U.S. Pat. No. 9,266,233, titled "Exosuit System," the contents of which are incorporated herein by reference. FLAs may also be used in connection with electrolaminate clutches, which are also described in the U.S. Pat. No. 9,266,233. The electrolaminate clutch (e.g., clutches configured to use electrostatic attraction to generate controllable forces between clutching elements) may provide power savings by locking a tension force without requiring the FLA to maintain the same force.

The powered actuators, or FLAs, are arranged on the base layer, connecting different points on the body, to generate forces for assistance with various activities. The arrangement can often approximate the wearer's muscles, in order to naturally mimic and assist the wearer's own capabilities. For example, one or more FLAs may connect the back of the torso to the back of the legs, thus approximating the wearer's hip extensor muscles. Actuators approximating the hip extensors may assist with activities such as standing from a seated position, sitting from a standing position, walking, or lifting. Similarly, one or more actuators may be arranged approximating other muscle groups, such as the hip flexors, spinal extensors, abdominal muscles or muscles of the arms or legs.

The one or more FLAs approximating a group of muscles are capable of generating at least 10 lbs over at least a ½ inch stroke length within 4 seconds. In some embodiments, one or more FLAs approximating a group of muscles may be capable of generating at least 250 lbs over a 6-inch stroke within ½ second. Multiple FLAs, arranged in series or parallel, may be used to approximate a single group of muscles, with the size, length, power, and strength of the FLAs optimized for the group of muscles and activities for which they are utilized.

The sensor and controls layer captures data from the suit and wearer, utilizes the sensor data and other commands to control the power layer based on the activity being performed, and provides suit and wearer data to the UX/UI layer for control and informational purposes.

Sensors such as encoders or potentiometers may measure the length and rotation of the FLAs, while force sensors measure the forces applied by the FLAs. Inertial measurement units (IMUs) measure and enable computation of kinematic data (positions, velocities and accelerations) of points on the suit and wearer. These data enable inverse dynamics calculations of kinetic information (forces, torques) of the suit and wearer. Electromyographic (EMG) sensors may detect the wearer's muscle activity in specific muscle groups. Electronic control systems (ECSs) on the suit may use parameters measured by the sensor layer to control the power layer. Data from the IMUs may indicate both the activity being performed, as well as the speed and intensity. For example, a pattern of IMU or EMG data may enable the ECS to detect that the wearer is walking at a specific pace. This information then enables the ECS, utilizing the sensor data, to control the power layer in order to provide the appropriate assistance to the wearer. Stretchable sensors may be used as a strain gauge to measure the strain of the elements in the stability layer, and thereby predict the forces in the elastic elements of the stability layer. Stretchable sensors may be embedded in the base layer or grip layer and used to measure the motion of the fabrics in the base layer and the motion of the body.

Data from the sensor layer may be further provided to the UX/UI layer, for feedback and information to the wearer, caregivers or service providers.

The UX/UI layer comprises the wearer's and others' interaction and experience with the exosuit system. This layer includes controls of the suit itself such as initiation of activities, as well as feedback to the wearer and caregivers. A retail or service experience may include steps of fitting, calibration, training and maintenance of the exosuit system. Other UX/UI features may include additional lifestyle features such as electronic security, identity protection and health status monitoring.

The assistive exosuit can have a user interface for the wearer to instruct the suit which activity is to be performed, as well as the timing of the activity. In one example, a user may manually instruct the exosuit to enter an activity mode via one or more buttons, a keypad, or a tethered device such as a mobile phone. In another example, the exosuit may detect initiation of an activity from the sensor and controls layer, as described previously. In yet another example, the user may speak a desired activity mode to the suit, which can interpret the spoken request to set the desired mode. The suit may be pre-programmed to perform the activity for a specific duration, until another command is received from the wearer, or until the suit detects that the wearer has ceased the activity. The suit may include cease activity features that, when activated, cause the suit to cease all activity. The cease activity features can take into account the motion being performed, and can disengage in a way that takes into account the user's position and motion, and safely returns the user to an unloaded state in a safe posture.

The exosuit may have a UX/III controller that is defined as a node on another user device, such as a computer or mobile smart phone. The exosuit may also be the base for other accessories. For example, the exosuit may include a cell phone chip so that the suit may be capable of receiving both data and voice commands directly similar to a cell phone, and can communicate information and voice signals through such a node. The exosuit control architecture can be configured to allow for other devices to be added as accessories to the exosuit. For example, a video screen may be connected to the exosuit to show images that are related to the use of the suit. The exosuit may be used to interact with smart household devices such as door locks or can be used to turn on smart televisions and adjust channels and other settings. In these modes, the physical assist of the suit can be used to augment or create physical or haptic experiences for the wearer that are related to communication with these devices. For instance, an email could have a pat on the back as a form of physical emoji that when inserted in the email causes the suit to physically tap the wearer or perform some other type of physical expression to the user that adds emphasis to the written email.

The exosuit may provide visual, audio, or haptic feedback or cues to inform the user of various exosuit operations. For example, the exosuit may include vibration motors to provide haptic feedback. As a specific example, two haptic motors may be positioned near the front hip bones to inform the user of suit activity when performing a sit-to-stand assistive movement. In addition, two haptic motors may be positioned near the back hip bones to inform the user of suit activity when performing a stand-to-sit assistive movement. The exosuit may include one or more light emitting diodes (LEDs) to provide visual feedback or cues. For example, LEDS may be placed near the left and/or right shoulders within the peripheral vision of the user. The exosuit may include a speaker or buzzer to provide audio feedback or cues.

In other instances, the interaction of the FLA's with the body through the body harness and otherwise can be used as a form of haptic feedback to the wearer, where changes in the timing of the contraction of the FLA's can indicate certain information to the wearer. For instance, the number or strength of tugs of the FLA on the waist could indicate the amount of battery life remaining or that the suit has entered a ready state for an impending motion.

The control of the exosuit may also be linked to the sensors that are measuring the movement of the wearer, or other sensors, for instance on the suit of another person, or sensors in the environment. The motor commands described herein may all be activated or modified by this sensor information. In this example, the suit can exhibit its own reflexes such that the wearer, through intentional or unintentional motions, cues the motion profile of the suit. When sitting, for further example, the physical movement of leaning forward in the chair, as if to indicate an intention to stand up, can be sensed by the suit IMU's and be used to trigger the sit to stand motion profile. In one embodiment, the exosuit may include sensors (e.g., electroencephalograph (EEG) sensor) that are able to monitor brain activity may be used to detect a user's desire to perform a particular movement. For example, if the user is sitting down, the EEG sensor may sense the user's desire to stand up and cause the exosuit to prime itself to assist the user in a sit-to-stand assistive movement.

The suit may make sounds or provide other feedback, for instance through quick movements of the motors, as information to the user that the suit has received a command or to describe to the user that a particular motion profile can be applied. In the above reflex control example, the suit may provide a high pitch sound and/or a vibration to the wearer to indicate that it is about to start the movement. This information can help the user to be ready for the suit movements, improving performance and safety. Many types of cues are possible for all movements of the suit.

Control of the suit includes the use of machine learning techniques to measure movement performance across many instances of one or of many wearers of suits connected via the internet, where the calculation of the best control motion for optimizing performance and improving safety for any one user is based on the aggregate information in all or a subset of the wearers of the suit. The machine learning techniques can be used to provide user specific customization for exosuit assistive movements. For example, a particular user may have an abnormal gait (e.g., due to a car accident) and thus is unable to take even strides. The machine learning may detect this abnormal gait and compensate accordingly for it.

FIGS. 1A-1C show front, back, and side views of a base layer 100 of an exosuit according to an embodiment. Base layer 100 may be worn as a single piece or as multiple pieces. As shown, base layer 100 is shown to represent multiple pieces that can serve as load distribution members (LDMs) for the power layer (shown in FIGS. 1D-1F). Base layer 100 and any LDMs thereof can cover or occupy any part of the human body as desired. The LDMs shown in FIGS. 1A-1C are merely illustrative of a few potential locations and it should be appreciated that additional LDMs may be added or certain LDMs may be omitted.

Base layer 100 can include calf LDMs 102 and 104 that are secured around the calf region or lower leg portion of the human. Calf LDMs 102 and 104 are shown to be positioned between the knees and the ankles, but this is merely illustrative. If desired, calf LDM 102 and 104 can also cover the foot and ankle and/or the knee.

Base layer 100 can include thigh LDMs 106 and 108 that are secured around the thigh region of the human. Thigh LDMs 106 and 108 are shown to be positioned between the knees and an upper region of the thighs. In some embodiments, thigh LDMs 106 and 108 and calf LDMs 102 and 104, respectively, may be merged together to form leg LDMs that cover the entirety of the legs and/or feet.

Base layer 100 can include hip LDM 110 that is secured around a hip region of the human. LDM 110 may be bounded such that it remains positioned above the toileting regions of the human Such bounding may make toileting relatively easy for the human as he or she would be not be required to remove base layer 100 to use the bathroom. In some embodiments, LDM 110 may be attached to thigh LDMs 106 and 108, but the toileting regions may remain uncovered. In another embodiment, a removable base layer portion may exist between LDM 100 and thigh LDMS 106 and 108.

Base layer 100 can include upper torso LDM 112 that is secured around an upper torso region of the human. Upper torso LDM 112 may include waist LDM 113, back LDM 114, shoulder LDM 115, and shoulder strap LDMs 116. Waist LDM 113, back LDM 114, shoulder LDM 115, and shoulder strap LDMs 116 may be integrally formed to yield upper torso LDM 112. In some embodiments, a chest LDM (not shown) may also be integrated into upper torso LDM 112. Female specific exosuits may have built in bust support for the chest LDM.

Base layer 100 can include upper arm LDMs 120 and 122 and lower arm LDMs 124 and 126. Upper arm LDMs 120 and 122 may be secured around bicep/triceps region of the arm and can occupy space between the shoulder and the elbow. Lower arm LDMs 124 and 126 may be secured around the forearm region of the arm and can occupy the space between the elbow and the wrist. If desired, upper arm LDM 120 and lower arm LDM 124 may be integrated to form an arm LDM, and upper arm LDM 122 and lower arm LDM 126 may be integrated to form another arm LDM. In some embodiments, arm LDMS 120, 122, 124, and 126 may form part of upper torso LDM 112.

Base layer 100 can include gluteal/pelvic LDM 128 that is secured the gluteal and pelvic region of the human. LDM 128 may be positioned between thigh LDMs 106 and 108 and hip LDM 110. LDM 128 may have removable portions such as buttoned or zippered flaps that permit toileting. Although not shown in FIGS. 1A-1C, LDMs may exist for the feet, toes, neck, head, hands, fingers, elbows, or any other suitable body part.

As explained above, the LDMs may serve as attachment points for components of the power layer. In particular, the components that provide muscle assistance movements typically need to be secured in at least two locations on the body. This way, when the flexible linear actuators are engaged, the contraction of the actuator can apply a force between the at least two locations on the body. With LDMs strategically placed around the body, the power layer can also be strategically placed thereon to provide any number of muscle assistance movements. For example, the power layer may be distributed across different LDMs or within different regions of the same LDM to approximate any number of different muscles or muscle groups. The power layer may approximate muscle groups such as the abdominals, adductors, dorsal muscles, shoulders, arm extensors, wrist extensors, gluteals, arm flexors, wrist flexors, scapulae fixers, thigh flexors, lumbar muscles, surae, pectorals, quadriceps, and trapezii. The power layer may also apply forces along paths that are not representative of biological muscle groups. For example, the power layer may wrap around the knee for stability and support.

FIGS. 1D-1F show front, back, and side views, respectively, of a power layer according to an embodiment. The power layer is shown as multiple segments distributed across and within the various LDMs. As shown, the power layer can include power layer segments 140-158. Each of power layer segments can include any number of flexible linear actuators. Some of the power layer segments may exist solely on the anterior side of the body, exist solely on the posterior side, start on the anterior side and wrap around to the posterior side, start on the posterior side and wrap around to the anterior side, or wrap completely around a portion of the body. Power layer segment (PLS) 140 may be secured to LDM 102 and LDM 106, and PLS 141 may be secured to LDM 104 and LDM 108. PLS 142 may be secured to LDM 106 and LDM 110 and/or LDM 114, and PLS 143 may be secured to LDM 108 and LDM 110 and/or LDM 114. PLS 145 may be secured to LDM 110 and LDM 113 and/or to LDM 114 or LDM 128. PLS 146 may be secured to LDM 115 and LDM 120, and PLS 147 may be secured to LDM 115 and LDM 122. PLS 148 may be secured to LDM 120 and LDM 124, and PLS 149 may be secured to LDM 122 and LDM 126.

PLS 150 may be secured to LDM 104 and LDM 108, and PLS 151 may be secured to LDM 102 and LDM 106. PLS 152 may be secured to LDM 106 and LDM 110 and/or to LDM 113, and PLS 153 may be secured to LDM 108 and LDM 110 and/or LDM 113. PLS 154 may be secured to LDM 112 and LDM 110. PLS 155 may be secured to LDM 112 and LDM 120, and PLS 156 may be secured to LDM 112 and LDM 122. PLS 157 may be secured to LDM 120 and LDM 124, and PLS 158 may be secured to LDM 122 and LDM 126.

It should be appreciated that the power layer segments are merely illustrative and that additional power layer segments may be added or that some segments may be omitted. In addition, the attachment points for the power layer segments are merely illustrative and that other attachment points may be used.

The human body has many muscles, including large and small muscles that are arranged in all sorts of different configuration. For example, FIGS. 1G and 1H show respective front and back views of a human male's musculature anatomy, which shows many muscles. In particular, the abdominals, adductors, dorsal muscles, shoulders, arm extensors, wrist extensors, gluteals, arm flexors, wrist flexors, scapulae fixers, thigh flexors, lumbar muscles, pectorals, quadriceps, and trapezii are all shown. It should be understood that several muscles and tendons are not shown.

The LDMs may be designed so that they can accommodate different sizes of individuals who don the exosuit. For example, the LDMs may be adjusted to achieve the best fit. In addition the LDMs are designed such that the location of the end points and the lines of action are co-located with the bone structure of the user in such a way that the flexdrive placement on the exosuit system are aligned with the actual muscle structure of the wearer for comfort, and the moment arms and forces generated by the flexdrive/exosuit system feel aligned with the forces generated by the wearer's own muscles.

Figure 1J:
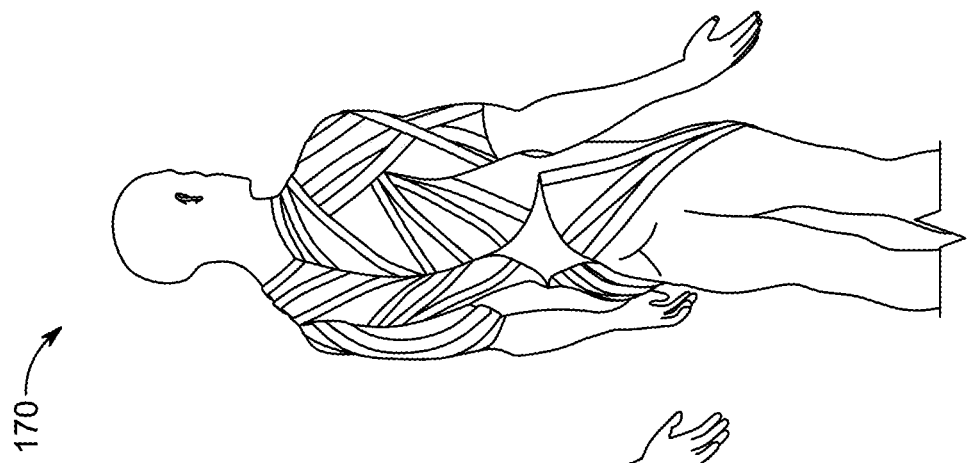
FIGS. 1I and 1J show front and side views of an illustrative exosuit having several power layer segments that approximate many of the muscles shown in FIGS. 1G and 1H, according to various embodiments.
Figure 1I:
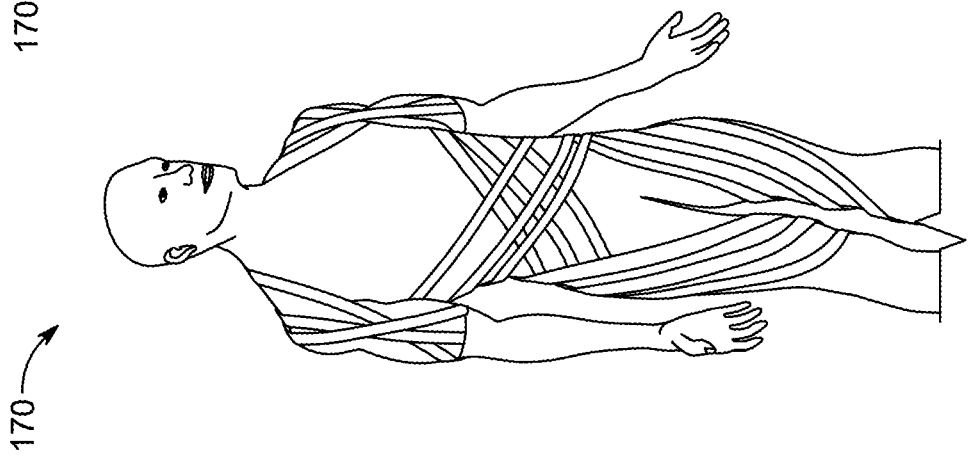
Figure 1H:
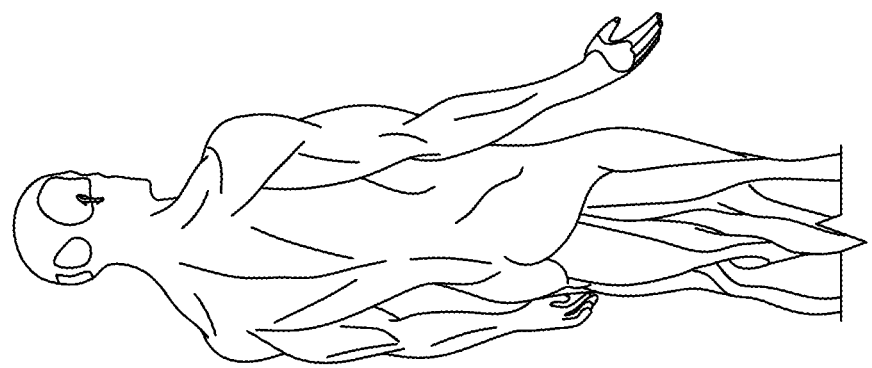
FIGS. 1G and 1H show respective front and back views of a human male's musculature anatomy, according to an embodiment.
Figure 1G:
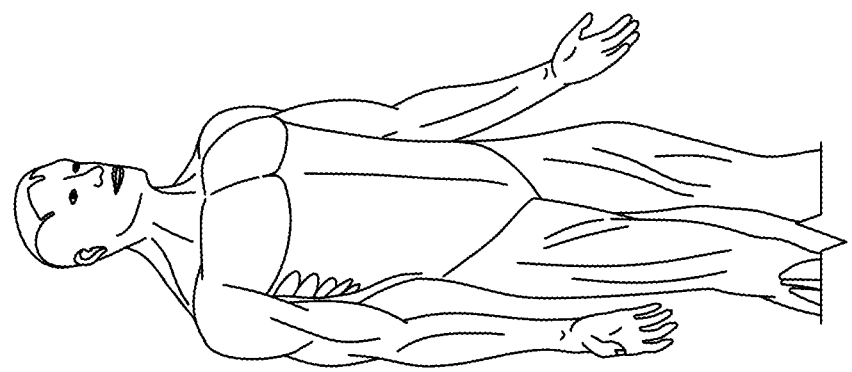

FIGS. 1I and 1J show front and side views of illustrative exosuit 170 having several power layer segments that approximate many of the muscles shown in FIGS. 1G and 1H. The power layer segments are represented by the individual lines that span different parts of the body. These lines may represent specific flexible linear actuators or groups thereof that work together to form the power layer segments that are secured to the LDMs (not shown). As shown, the FLAs may be arrayed to replicate at least a portion of each of the abdominal muscles, dorsal muscles, shoulder muscles, arm extensor and flexor muscles, gluteal muscles, quadriceps muscles, thigh flexor muscles, and trapezii muscles. Thus, exosuit 170 exemplifies one of many possible different power layer segment arrangements that may be used in exosuits in accordance with embodiments discussed herein. These power layer segments are arranged so that the moment arms and forces generated feel like forces being generated by the user's own muscles, tendons, and skeletal structure. It should be appreciated that the power layer segments can be designed to approximate other muscles and tendons that are not shown in FIGS. 1G and 1H. Other possible power layer segment arrangements are illustrated and discussed below.

The power layer segments may be arranged such that they include opposing pairs or groups, similar to the way human muscles are arranged in opposing pairs or groups of muscles. That is, for a particular movement, the opposing pairs or groups can include protagonist and antagonist muscles. While performing the movement, protagonist muscles may perform the work, whereas the antagonist muscles provide stabilization and resistance to the movement. As a specific example, when a user is performing a curl, the biceps muscles may serve as the protagonist muscles and the triceps muscles may serve as the antagonist muscles. In this example, the power layer segments of an exosuit may emulate the biceps and triceps. When the biceps human muscle is pulling to bend the elbow, the exosuit triceps power layer segment can pull on the other side of the joint to resist bending of the elbow by attempting to extend it. The power layer segment can be, for example, either be a FLA operating alone to apply the force and motion, or a FLA in series with an elastic element. In the latter case, the human biceps would be working against the elastic element, with the FLA adjusting the length and thereby the resistive force of the elastic element.

Thus, by arranging the power layer segments in protagonist and antagonist pairs, the power layers segments can mimic or emulate any protagonist and antagonist pairs of the human anatomy musculature system. This can be used to enable exosuits to provide assistive movements, alignment movements, and resistive movements. For example, for any exercise movement requires activation of protagonist muscles, a subset of the power layer segments can emulate activation of antagonist muscles associated with that exercise movement to provide resistance.

The design flexibility of the LDMs and PLSs can enable exosuits to be constructed in accordance with embodiments discussed herein. Using exosuits, the power layer segments can be used to resist motion, assist motion, or align the user's form.

FIGS. 1K-1M shows illustrative side, front, and back views of core/lumber LDM 180 according to an embodiment. Power layers are not shown. LDM 180 encircles the lumbar, abdomen, and sides of the person wearing the exosuit. LDM 180 can be designed to apply forces in a radially inward manner from the exterior of the body to the interior of the body (e.g., such that the inward applied forces are directed to the spine). Different illustrative forces, F1-F3, are shown being applied to the lumbar region and forces, F4-F6 are shown being applied to the abdominal region. In some embodiments, LDM 180 may be tuned to provide a subset of forces F1-F6. For example, in one embodiment, LDM 180 may be constructed to primarily apply forces F2 and F4. In another embodiment, LDM 180 may be constructed to primarily apply forces F1, F3, F5, and F6. Dashed lines 181-186 illustrate potential paths along which one or more power layers operate to increase or decrease applied pressure to the core/lumbar region of the user. For example, one or more FLAs may shorten their respective lengths along one or more lines 181-186 to apply the desired forces. Note that lines 181 and 182 cross each other as they wrap around the waist. This crossing may stabilize LDM 180 while it is under load and providing support for flexor and extensor assistive actions. Paths 183 and 184 are shown crossing the abdomen and paths 185 and 186 are shown crossing the lumbar. It should be understood that the LDM 180 may designed to cover any suitable region of the core, including any region between the rib cage and the bottom part of the pelvis. Different embodiments discussed herein show different implementations that provide core/lumbar support.

Figure 2A:
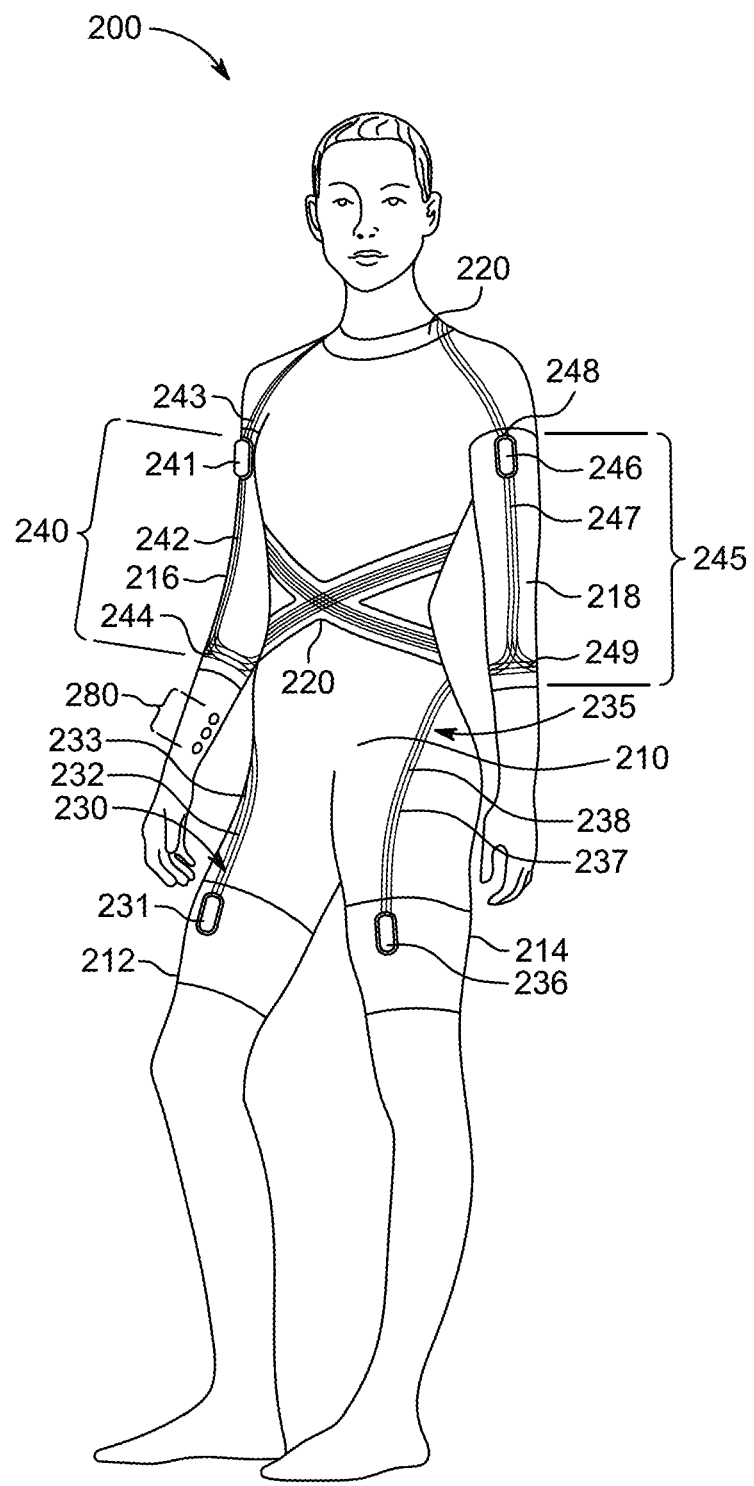
FIGS. 2A and 2B show front and back view of illustrative exosuit according to an embodiment.
Figure 2B:
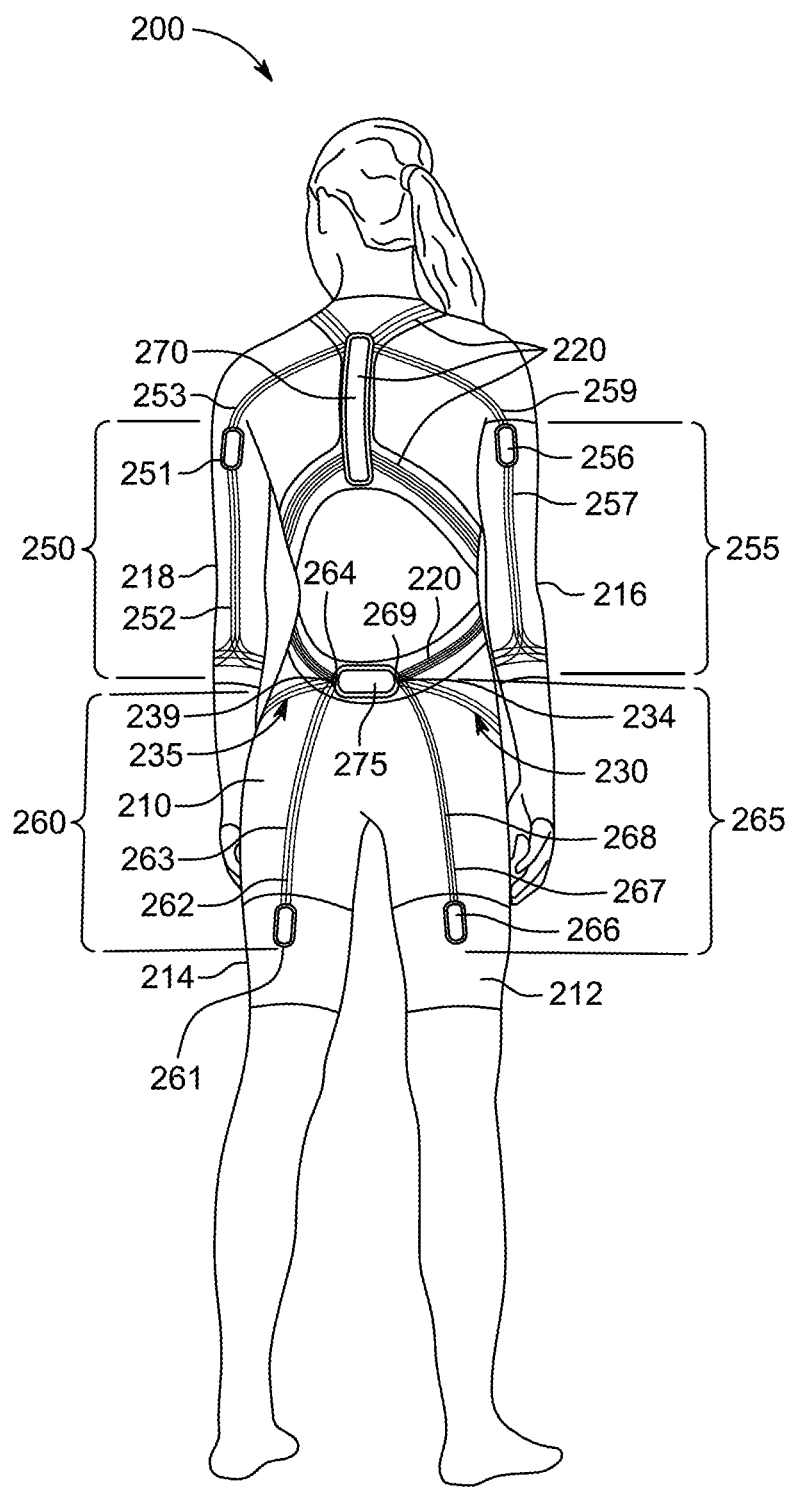

FIGS. 2A and 2B show front and back view of illustrative exosuit 200 according to an embodiment. Exosuit 200 may embody some or all of the base layer, stability layer, power layer, sensor and controls layer, a covering layer, and user interface/user experience (UI/UX) layer, as discussed above. In addition, exosuit 200 may represent one of many different specification implementations of the exosuit shown in FIGS. 1A-1F. Exosuit 200 can include base layer 210 with thigh LDMs 212 and 214, arm LDMs 216 and 218, and upper torso LDM 202. Thigh LDMs 212 and 214 may wrap around the thigh region of the human, and arm LDMs 216 and 218 may wrap around arm region (including the elbow) of the human. Upper torso LDM 220 may wrap around the torso and neck of the human as shown. In particular, LDM 220 may cross near the abdomen, abut the sacrum, cover a portion of the back, and extend around the neck.

Exosuit 200 can include PLSs 230 and 235 secured to thigh LDM 212 and 214 and upper torso LDM 220. PLSs 230 and 235 may provide leg muscle flexor movements. PLS 230 may include flexdrive subsystem 231, twisted string 232, and power/communication lines 233. Flexdrive subsystem 231 may include a motor, sensors, a battery, communications circuitry, and/or control circuitry. Twisted string 232 may be attached to flexdrive subsystem 231 and an attachment point 234 on LDM 220. Power/communications lines 233 may convey control signals and/or power to flexdrive subsystem 231. PLS 235 may include flexdrive subsystem 236, twisted string 237, and power/communication lines 238. Twisted string 237 may be attached to flexdrive subsystem 236 and attachment point 239.

Exosuit 200 can include PLSs 240 and 245 and PLSs 250 and 255 that are secured to LDMs 216, 218, and 220 (as shown). PLSs 240 and 245 may provide arm muscle flexor movements, and PLSs 250 and 255 may provide arm muscle extensor movements. PLS 240 may include flexdrive subsystem 241, twisted string 242, and power/communication lines 243. Twisted string 242 may be attached to flexdrive subsystem 241 and attachment point 244. Power/communication lines 243 may be coupled to power and communications module 270. PLS 245 may include flexdrive subsystem 246, twisted string 247, and power/communication lines 248. Twisted string 247 may be attached to flexdrive subsystem 246 and attachment point 249. Power/communication lines 248 may be coupled to power and communications module 270. PLS 250 may include flexdrive subsystem 251, twisted string 252, and power/communication lines 253. Twisted string 252 may be attached to flexdrive subsystem 251 and attachment point 254. Power/communication lines 253 may be coupled to power and communications module 270. PLS 250 may include flexdrive subsystem 256, twisted string 257, and power/communication lines 258. Twisted string 256 may be attached to flexdrive subsystem 256 and attachment point 259. Power/communication lines 258 may be coupled to power and communications module 270.

Exosuit 200 can include PLS 260 and 265 that are secured to thigh LDMs 212 and 214 and LDM 220. PLSs 260 and 265 may provide lea muscle extensor movements. PLS 260 may include flexdrive subsystem 261, twisted string 262, and power/communication lines 263. Twisted string 262 may be attached to flexdrive subsystem 261 and attachment point 264. Power/communication lines 263 may be coupled to power and communications module 275. PLS 266 may include flexdrive subsystem 266, twisted string 267, and power/communication lines 268. Twisted string 267 may be attached to flexdrive subsystem 266 and attachment point 269. Power/communication lines 263 may be coupled to power and communications module 275

Exosuit 200 is designed to assist, resist, align, or enhance movements being performed by the user of the suit. Exosuit 200 may include many sensors in various locations to provide data required by control circuitry to provide such movements. These sensors may be located anywhere on base layer 210 and be electrically coupled to power and communications lines (e.g., 233, 237, 243, 247, 253, 257, 263, 267, or other lines). The sensors may provide absolute position data, relative position data, accelerometer data, gyroscopic data, inertial moment data, strain gauge data, resistance data, or any other suitable data.

Exosuit 200 may include user interface 280 that enables the user to control the exosuit. For example, user interface 280 can include several buttons or a touch screen interface. User interface 280 may also include a microphone to receive user spoken commands. User interface 280 may also include a speaker that can be used to playback voice recordings. Other user interface element such as buzzers (e.g., vibrating elements) may be strategically positioned around exosuit 200.

Exosuit 200 can include communications circuitry such as that contained in power and communications module 270 or 275 to communicate directly with a user device (e.g., a smartphone) or with the user device via a central server. The user may use the user device to select one or more movements he or she would like to perform, and upon selection of the one or more movements, exosuit 200 can the assist, resist, or align movement. The user device or exosuit 200 may provide real-time alignment guidance as to the user's performance of the movement, and exosuit 200 may provide resistance, alignment, or assistance to the movement.

Lumbar/Core/waist support structures according to various embodiments discussed herein provide core and lumbar support to the user of the exosuit. Core and lumbar support can be used to facilitate various exosuit assistance movements and stability functionality. Different configurations can be used to apply forces to different core regions of the user. Embodiments discussed in connection with FIGS. 3-15 show a lumbar/core support grip configuration that can be integrated into the base layer of N2S layer of the exosuit. FIGS. 3A-15E shows a vertical stay core support grip configuration. FIGS. 19A-26B shows another core support grip that minimizes or eliminates the use of hard rigid materials such as plastic.

Figure 2C:
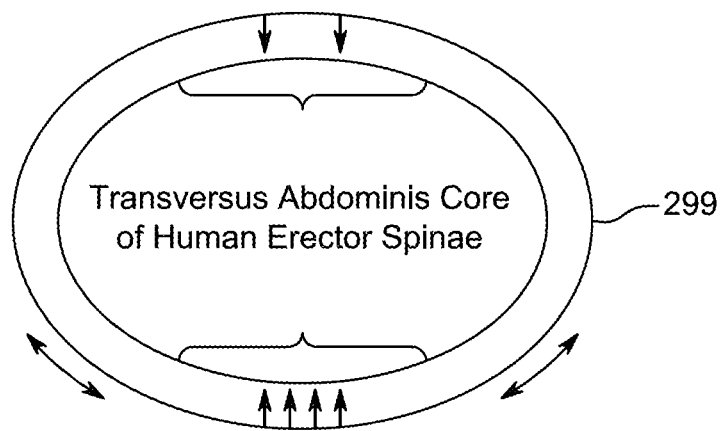
FIG. 2C shows illustrative cross-section of a core region of a human being, according to an embodiment.
Figure 2D:
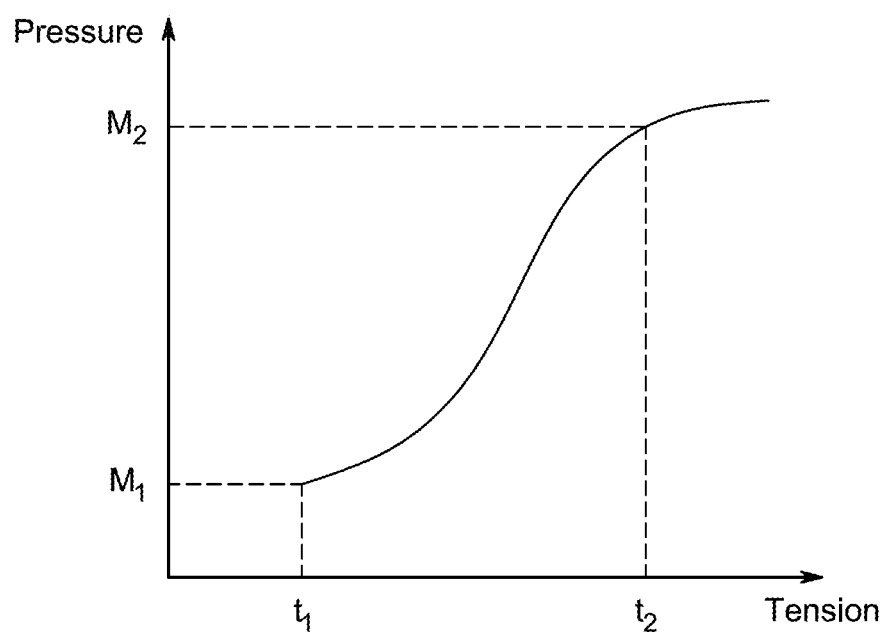
FIG. 2D shows an illustrative graph showing pressure exerted onto the core of a human in response to a tension applied by a adjustable lumbar tensioning member, according to an embodiment.

FIG. 2C shows illustrative cross-section of a core region of a human being, with emphasis showing the transversus abdominis (e.g., ab muscles) and erector spinae (e.g., back extension muscles), and also showing an adjustable lumbar tensioning member 299 that is situated around the core region. FIG. 2D shows an illustrative graph showing pressure exerted onto the core of a human in response to a tension applied by adjustable lumbar tensioning member 299. The graph in FIG. 2D is shown as non-linear, but it could be linear. Lumbar tensioning member 299 can exert pressure to a person's lower back and/or abs in response to an increase of tension or decrease said pressure in response to a decrease in tension. That is, as lumbar tensioning member 299 tightens it grip around the core of the person, it is able to exert more and more pressure to the lower back and/or abs. Depending on the design of lumbar tensioning member, more pressure may be applied to the lower back than the abs, or vice versa, or the application of pressure may be approximately equal. In addition, pressure can be applied above the lumbar region to provide upward pressure that acts as a spinal traction/upper body load holder to reduce load on the spine. The core/lumbar grip members discussed herein can be outfitter with one of several different lumbar tensioning systems.

FIGS. 3A-15D shows a core support system that can be integrated with the base layer of an exosuit or mounted around the core region of a user. The core support system can include several different stay members that are strategically positioned on the exosuit to provide load distribution support and core support.

Figures 3A, 3B, 3C:
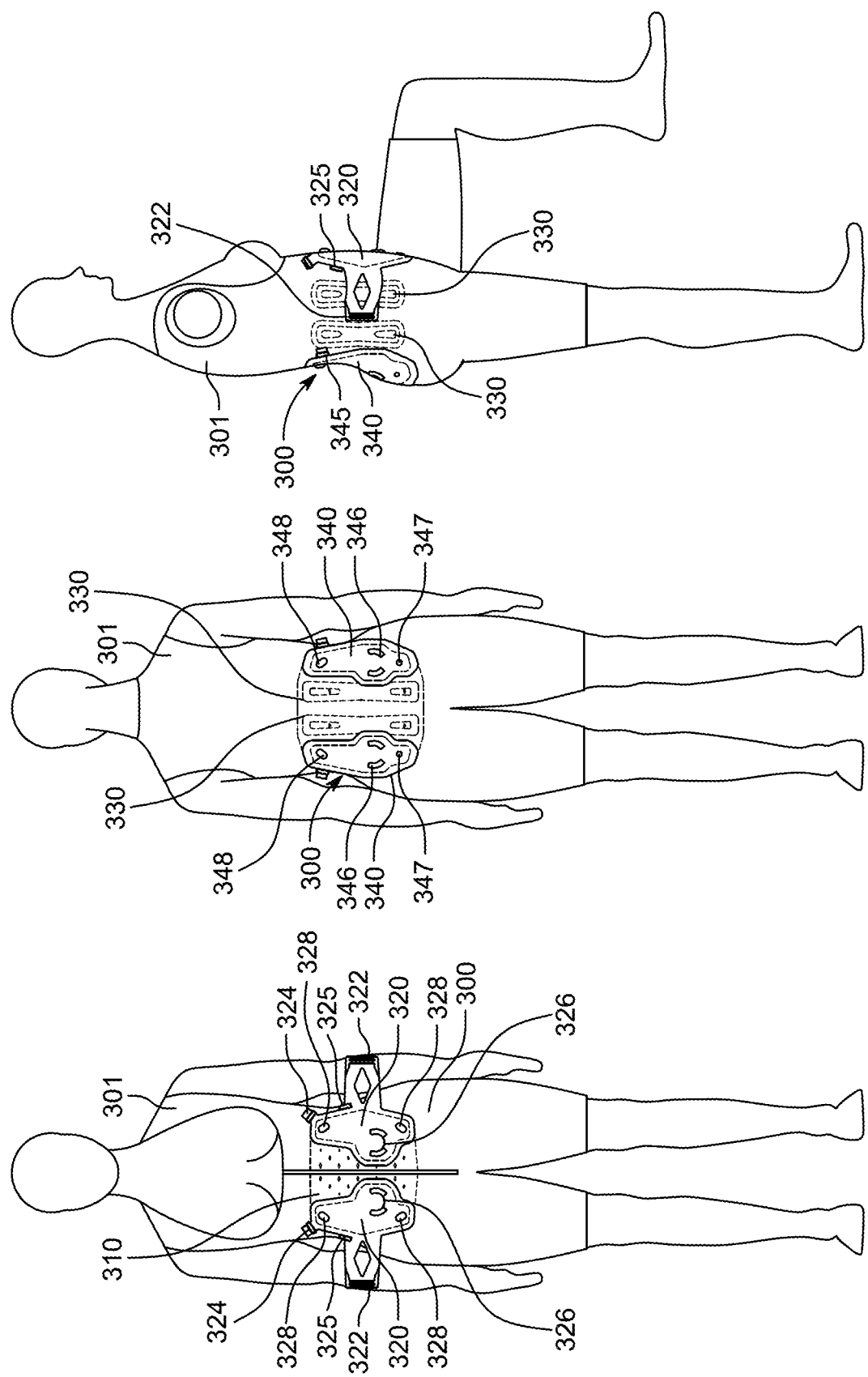
FIGS. 3A-3C show illustrative front, back, and side views of a core support grip according to an embodiment.

FIGS. 3A-3C show illustrative front, back, and side views of core support grip (CSG) 300 according to an embodiment. CSG 300 is at partially integrated with base layer 301 and is designed to wrap around the torso in the lumbar, hip, and abdomen regions. CSG 300 is adjustable to fit different body sizes and types. CSG 300 can serve as a load distribution member for interfacing with FLAs and other load distribution members. CSG 300 may be able to selectively adjust compression it applies to the body via power layer segments (not shown). CSG 300 can include front sub-stay 310, front main stay 320, back sub-stay 330, back main stay 340, and side stays 350. Each of stays 310, 320, 330 and 340 may be constructed from a stack up of materials and components or a change in the mechanical properties of one material using an engineered fabrication process (e.g., an engineered woven, knit, or non-woven material). Each of stays 310, 320, 330, and 340 provide stability for distributing loads.

Front main stay 320 may include attachment points 322, adjustable buckles 324 and 325, FLA attachment points 326, and pass through ports 328. Back main stay 340 may include attachment points 347 adjustable buckles 345, FLA attachment points 346, and pass through ports 348.

Front sub-stay 310 may be integrated into base layer 301 and front main stay 320 may interface with and be secured to front sub-stay 310. Back sub-stay 330 may be integrated into base layer 301 and back main stay 340 may interface with and be secured to back sub-stay 330. Side stays 350 may be integrated into base layer 301. Attachment points 322 may be connected to back main stay 340 or a tensioning member (not shown) that is connected to a first attachment point 322, wraps around back main stay 340 and is connected to a second attachment point 322. Adjustable buckles 324 may interface with a shoulder yoke (not shown). Adjustable buckles 325 and 345 may be used to couple front and back main stays 320 and 340 together via a strap or tensioning member.

Figure 4C:
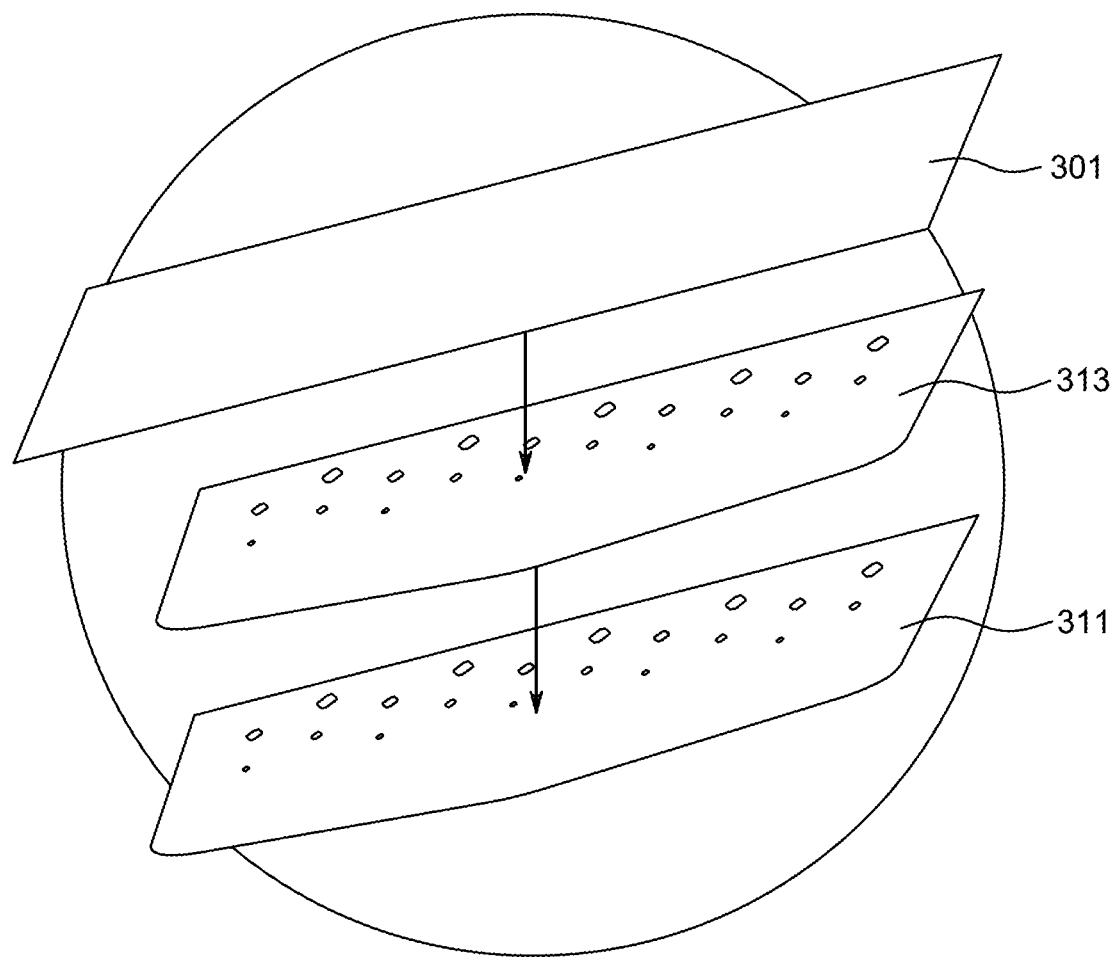

FIGS. 4A-4C show different views of front sub-stay 310 according to various embodiments. In particular, FIG. 4A shows sub-stay 310 as it exists with respect to base layer 301. Sub-stay 310 may exist on the underside of base layer 301 and directly interface with the skin of the wearer. FIG. 4B shows that sub-stay 310 includes textile portions 311 and 312 and adhesive portions 313 and 314. Portions 311 and 313 may be secured to base layer 301 adjacent to a first side of zipper 302 and portions 312 and 314 may be secured to base layer 301 adjacent to a second side of zipper. FIG. 4C illustrates the stack up, which shows base layer 301, adhesive portion 313 or 314 and textile portion 311 or 312. Thus, the textile portions 311 and 312 directly contact the wearer's skin and adhesive portions 313 and 314 secure the textile portions 311 and 312 to base layer 301. Portions 311 and 313 may be cut to be approximately the same size so that they line up perfectly when they are attached to base layer 301. The same holds true for portions 312 and 314.

Figure 5B:
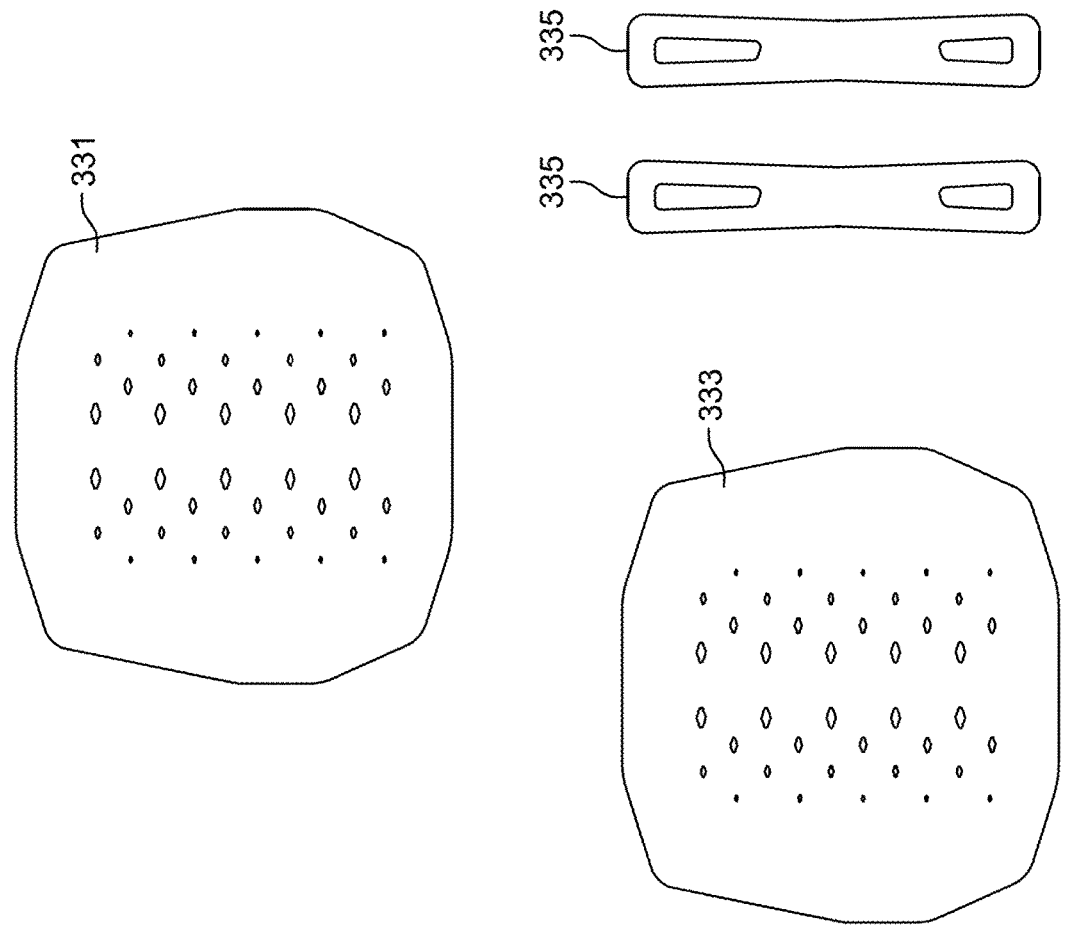
FIGS. 5A-5C show different views of a back sub-stay according to various embodiments.
Figure 5A:
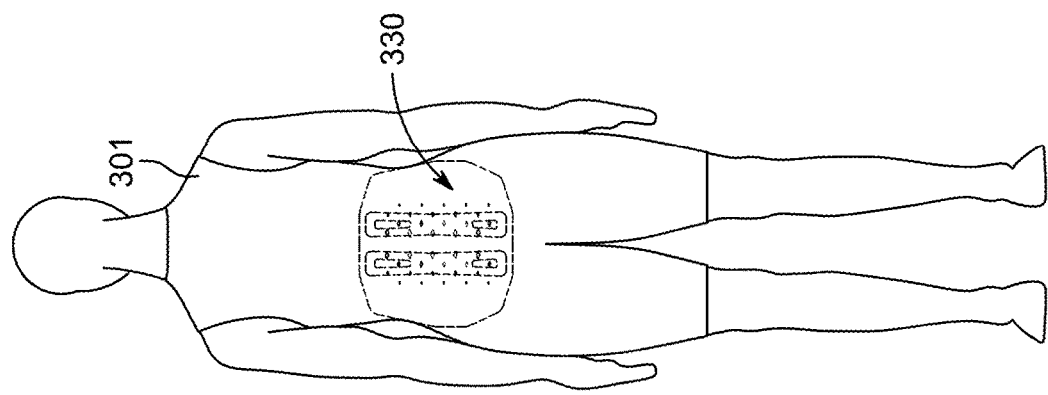
Figure 5C:
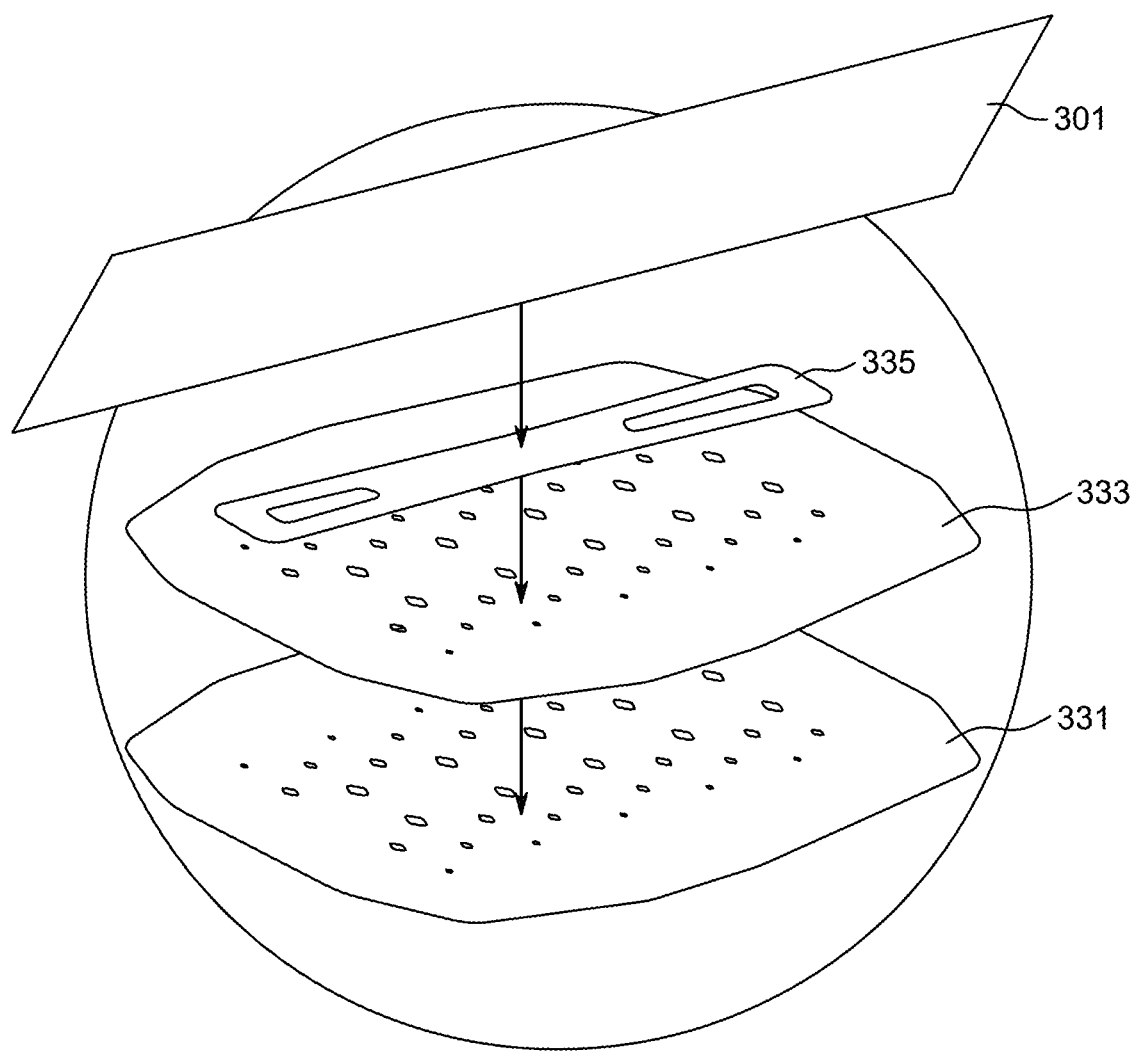

FIGS. 5A-5C show different views of back sub-stay 330 according to various embodiments. In particular, FIG. 5A shows sub-stay 330 as it exists with respect to base layer 301. Sub-stay 330 may exist on the underside of base layer 310 and directly interface with the skin of the wearer. FIG. 5B shows that sub-stay 330 includes textile portion 331, adhesive portion 333, and rigid portions 335. Rigid portions 335 may be constructed from nylon, plastic, or other material that has minimum degree of rigidity. FIG. 5C shows that sub-stay 330 stack up has textile portion 331 positioned direct next to the user's skin, with adhesive 333 on top of textile portion 331 and sandwiching rigid portions 335 between adhesive 333 and base layer 301. Portions 331 and 333 may be sized approximately the same size and rigid portions 335 may be sized such that two or more can be used in back sub-stay 330. In some embodiments, one rigid portion 335 may be placed adjacent to a first side of the user's spine and a second rigid portion 335 may be placed adjacent to a second side of the user's spine.

Figures 6A, 6B:
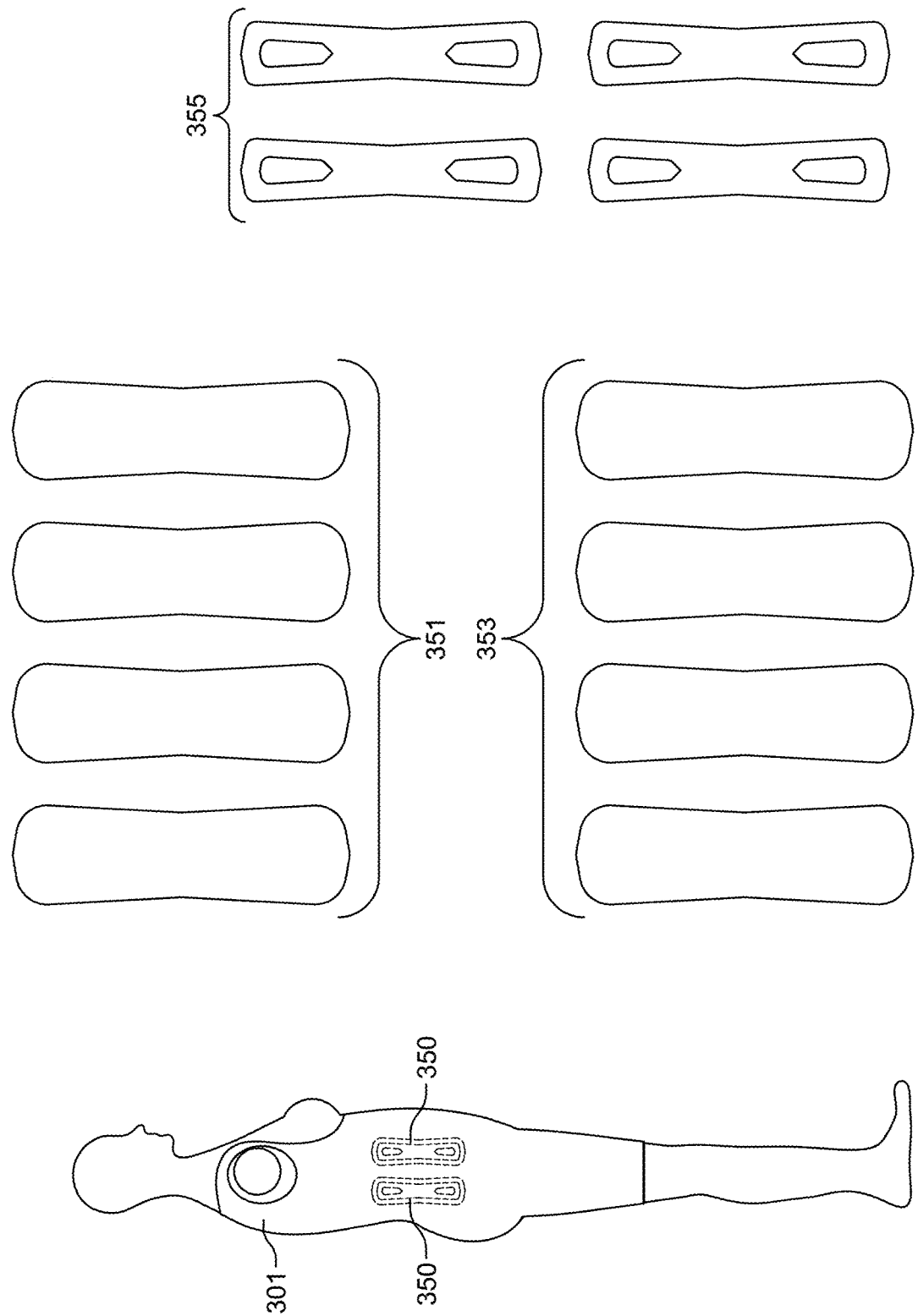
FIGS. 6A-6C show different views of a side stay according to various embodiments.
Figure 6C:
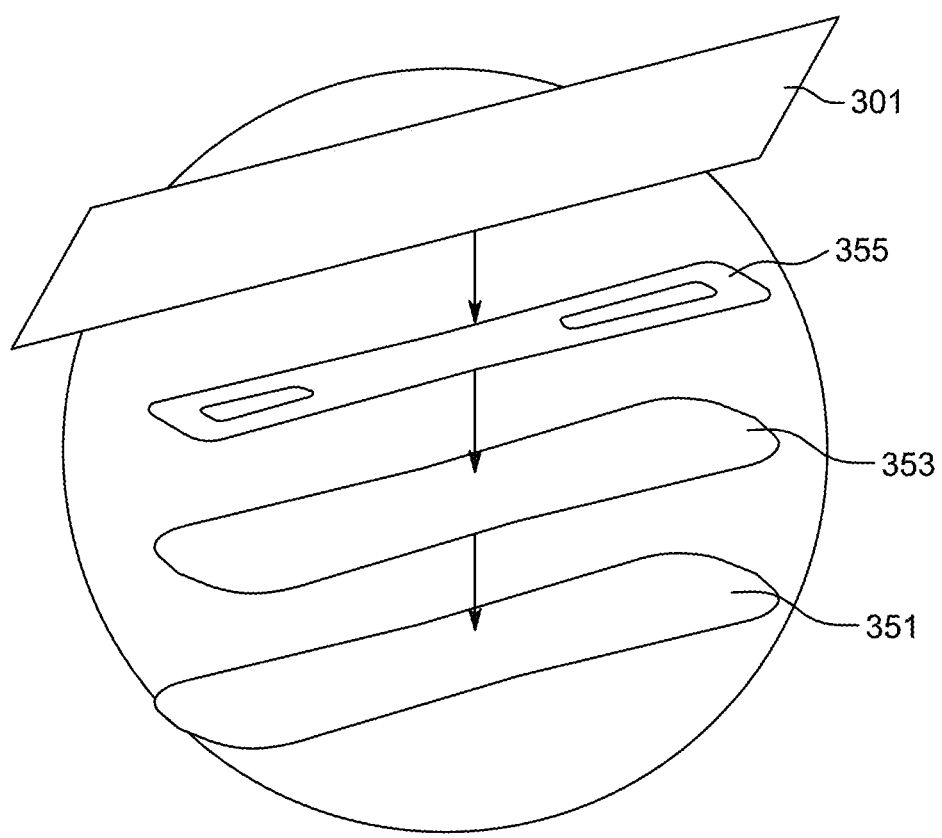

FIGS. 6A-6C show different views of side stay 350 according to various embodiments. In particular, FIG. 6A shows multiple side stays 350 as they exist with respect to base layer 301. As shown, two side stays 350 may exist on each side of the user. Side stay 350 may exist on the underside of base layer 310 and directly interface with the skin of the wearer. FIG. 6B shows that side stay 350 can include textile portion 351, adhesive portion 353, and rigid portion 355. Rigid portions 355 may be constructed from nylon, plastic, or other material that has minimum degree of rigidity. FIG. 6C shows that side stay 350 stack up has textile portion 351 positioned direct next to the user's skin, with adhesive 353 on top of textile portion 331 and sandwiching rigid portions 355 between adhesive 353 and base layer 301. Portions 351 and 353 may be sized approximately the same size and rigid portions 355 may be sized differently (e.g., smaller) than portions 351 and 353.

Figure 7A:
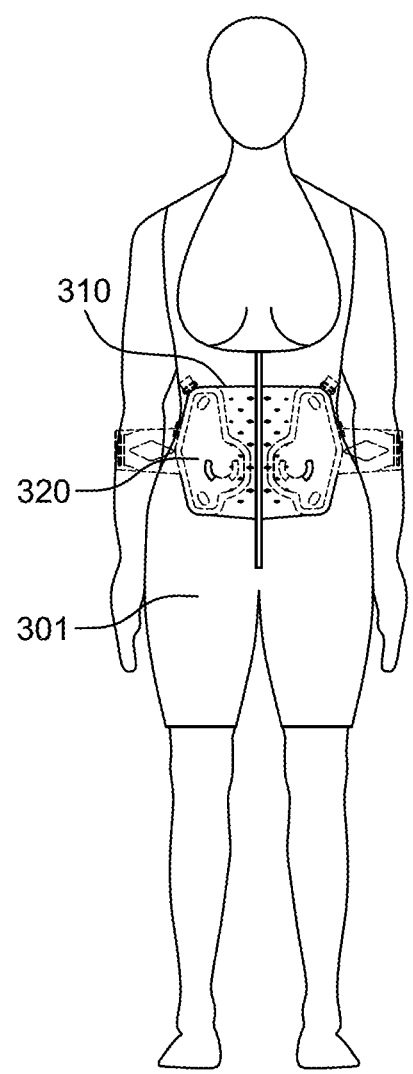
FIGS. 7A-7C show different views of a front main stay according to an embodiment.
Figure 7B:
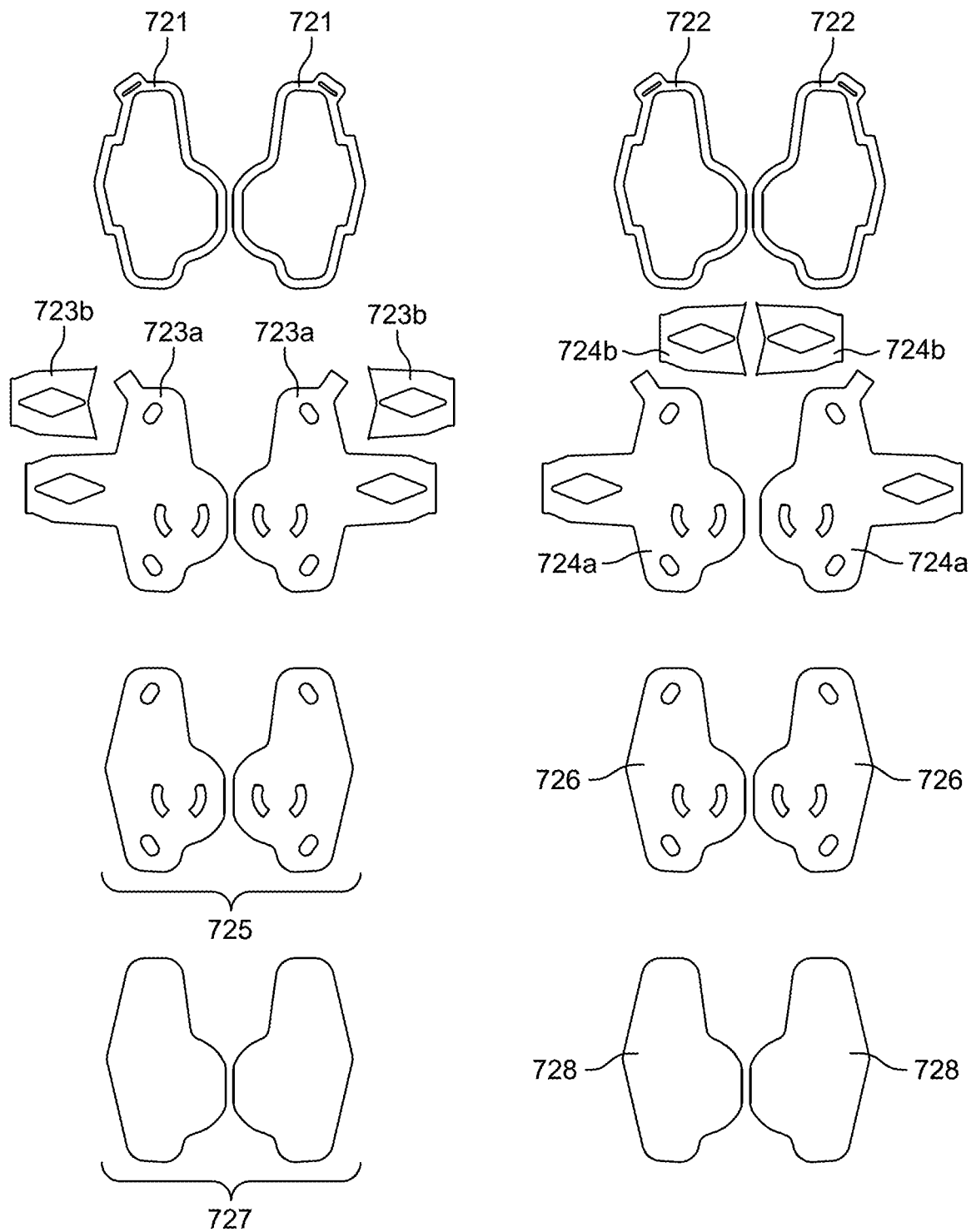
Figure 7C:
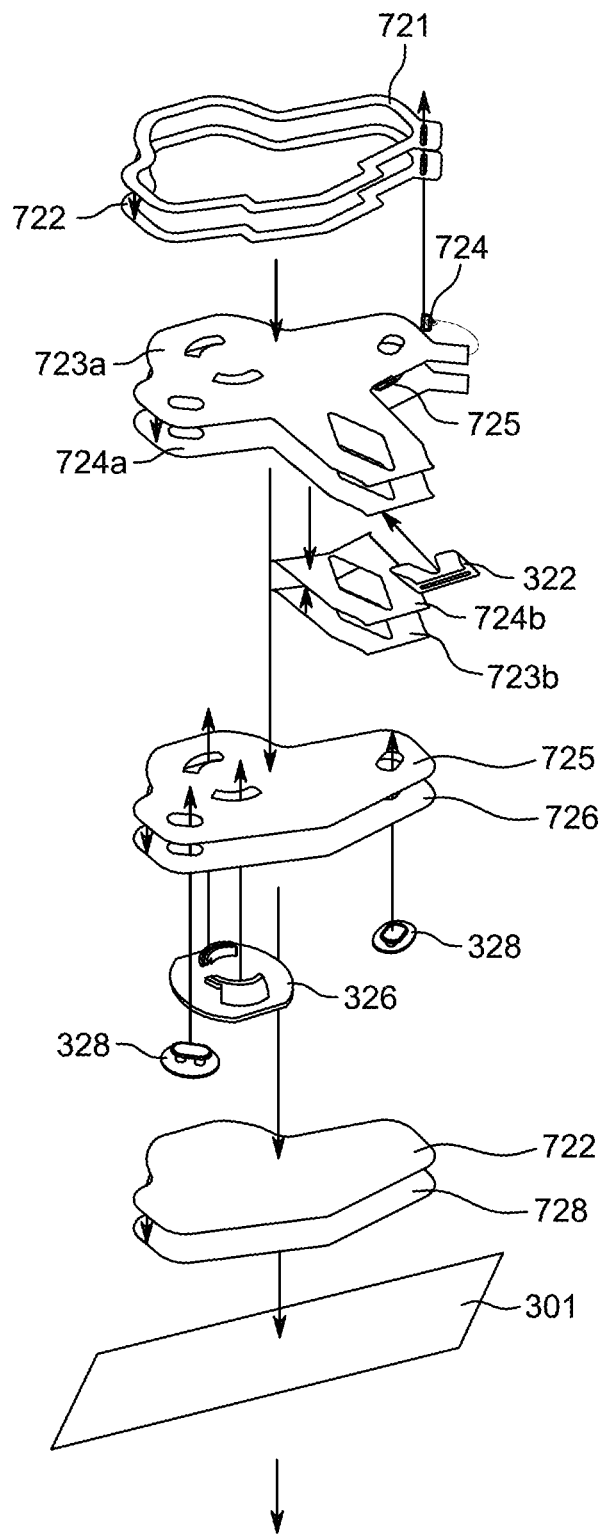

FIGS. 7A-7C show different views of front main stay 320 according to an embodiment. FIG. 7A shows the positioning of main stay 320 as it is overlaid over sub-stay 310. Attachment points 322 are shown extending outwards away from the body and not wrapped around the body as they would otherwise be positioned during use. Main stay 320 may be secured to sub-stay 310 via an adhesive or other securing agent such as sewing. FIG. 7B shows that main stay 320 is includes outline portions 721, textile portions 723a and 723b, rigid portions with cutouts 725, rigid portions 727, adhesive portions 722, adhesive portions 724a and 724b, adhesive portions 726, and adhesive portions 728. All the layers may have cutouts, if desired, and the shape of each cutout may alter the load path on the stay. Adhesive portions 722, adhesive portions 724a and 724b, adhesive portions 726, and adhesive portions 728 are sized the same as outline portions 721, textile portions 723a and 723b, rigid portions with cutouts 725, and rigid portions 727, respectively.

FIG. 7C shows the stack up arrangement of front main stay 320. Starting at the top, outline portion 721 is secured to textile portion 723a via adhesive portion 722. Buckles 324 and 325 are bonded to textile portion 723a by being sandwiched between textile portion 723a and adhesive portion 724a. Textile portion 723b may be secured to adhesive portion 724b, which couples buckle 322 to adhesive portion 724a. Rigid portion with cutout 725 may be secured to adhesive portion 724a. FLA attachment points 326 and pass through ports 328 may be secured to rigid portion with cutout 725. FLA attachment points 326 and pass through ports 328 may extend through the cutouts in rigid portion 725, adhesive portions 724a and 726, and textile portion 723a. Rigid portion 727 may hold FLA attachment points 326, and pass through ports 328 in place against adhesive portion 726, and adhesive portion 728 may couple rigid portion 727 to base layer 301.

Figure 8A:
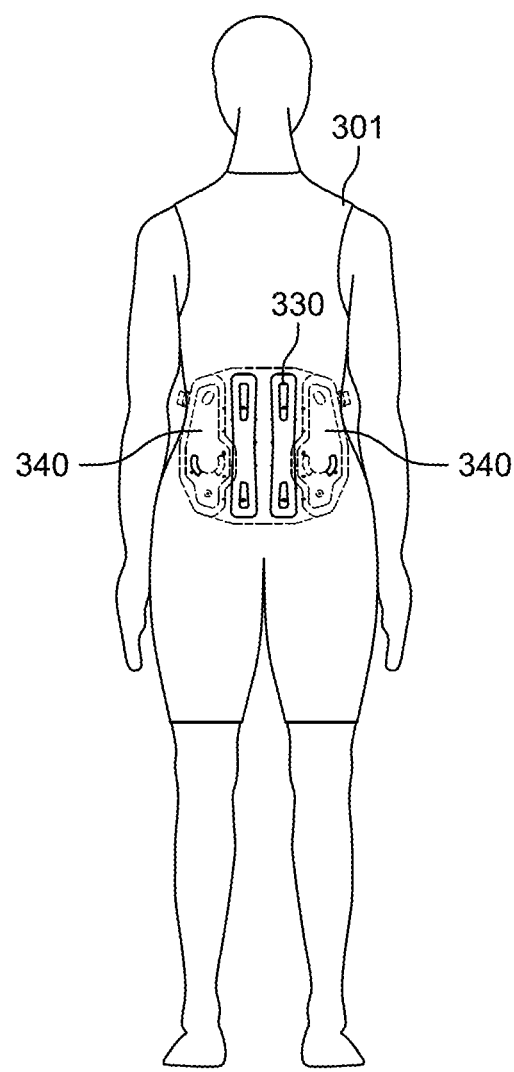
FIGS. 8A-8C show different views of a back main stay according to an embodiment.
Figure 8B:
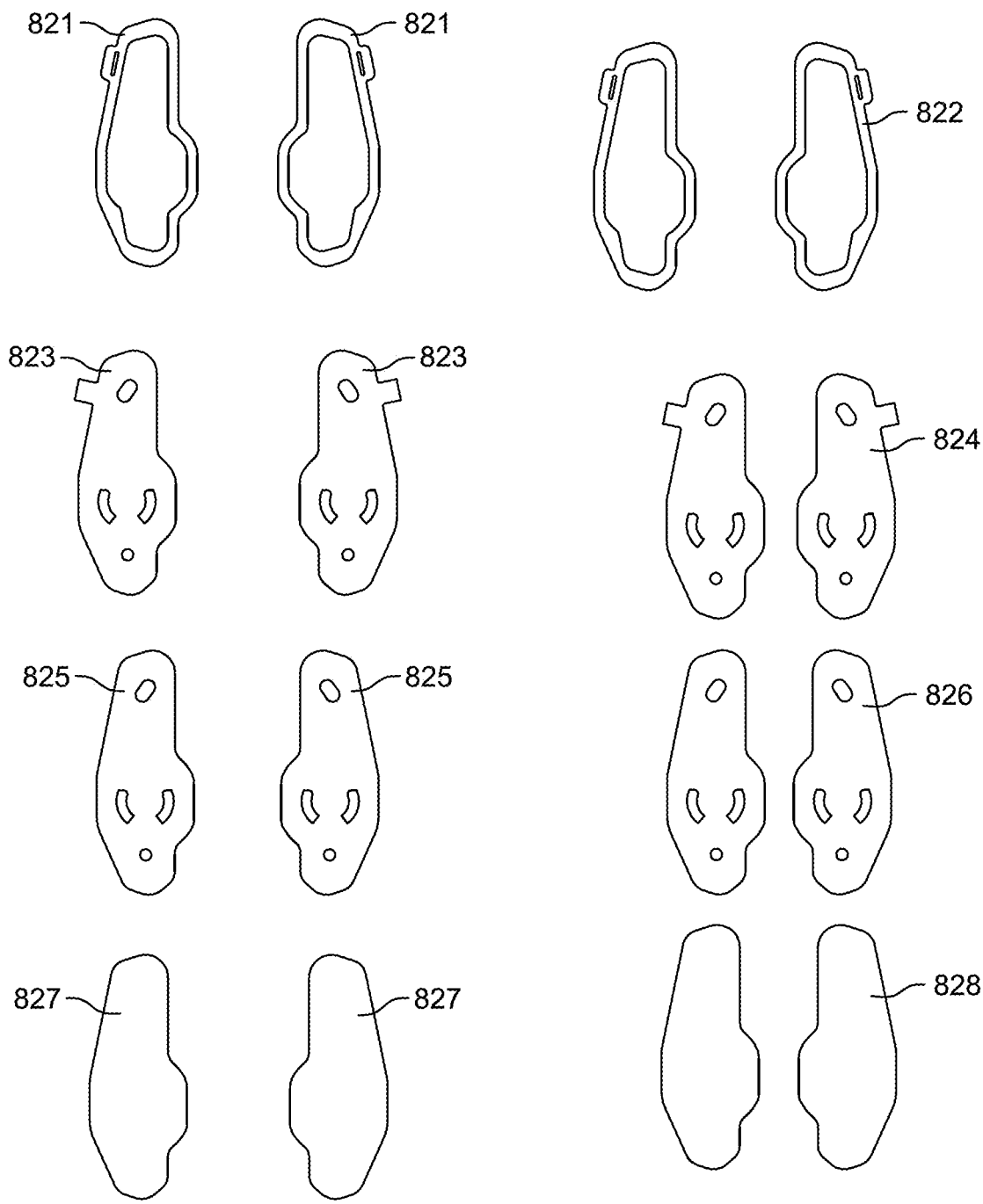
Figure 8C:
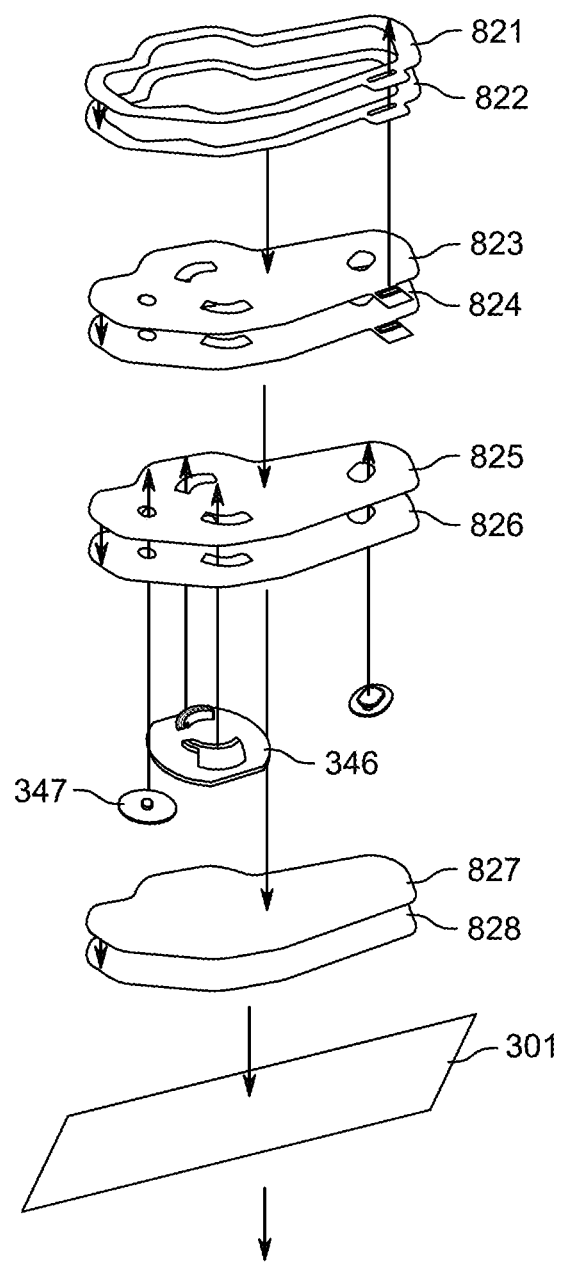

FIGS. 8A-8C show different views of back main stay 340 according to an embodiment. FIG. 8A shows the positioning of main stay 340 as it is overlaid over sub-stay 330. Back main stay 340 may be secured to sub-stay 330 via an adhesive or other securing agent such as sewing. FIG. 8B shows that main stay 340 can include outline portions 821, textile portions 823, rigid portions with cutouts 825, rigid portions 827, adhesive portions 822, adhesive portions 824, adhesive portions 826, and adhesive portions 828. Adhesive portions 822, adhesive portions 824, adhesive portions 826, and adhesive portions 828 are sized the same as outline portions 821, textile portions 823, rigid portions with cutouts 825, and rigid portions 827, respectively.

FIG. 8C shows the stack up arrangement of back main stay 340. Starting at the top, outline portion 821 is secured to textile portion 823 via adhesive portion 822. Buckle 345 is bonded to textile portion 823 by being sandwiched between textile portion 823 and adhesive portion 824. Rigid portion with cutout 725 may be secured to adhesive portion 724a. FLA attachment points 326 and pass through ports 328 may be secured to rigid portion with cutout 725. FLA attachment points 326 and pass through ports 328 may extend through the cutouts in rigid portion 725, adhesive portions 724a and 726, and textile portion 723a. Rigid portion 727 may hold FLA attachment points 326, and pass through ports 328 in place against adhesive portion 726, and adhesive portion 728 may couple rigid portion 727 to base layer 301.

Figure 9:
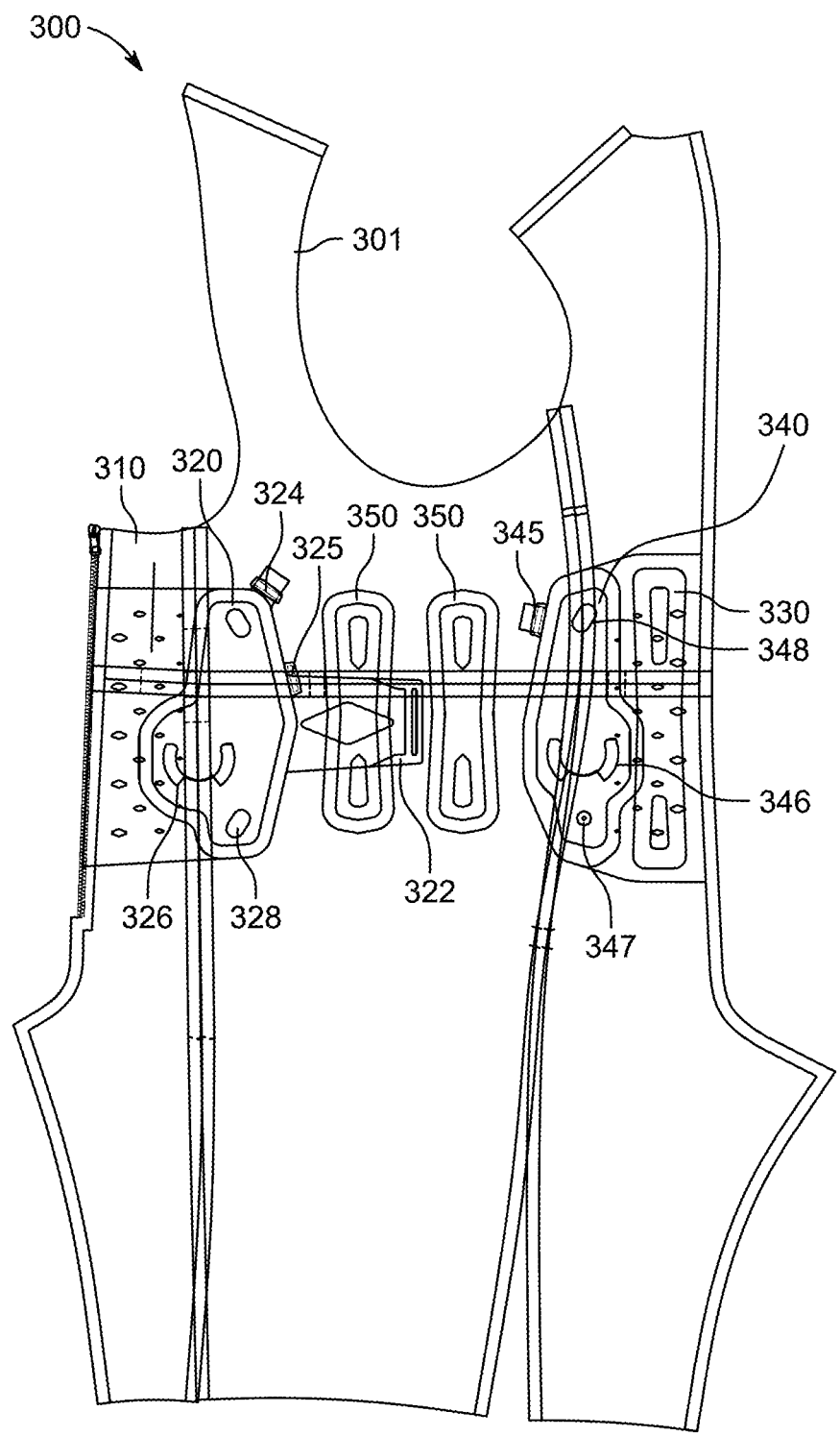
FIG. 9 shows illustrative side view of a portion of a core support grip, according to an embodiment.

FIG. 9 shows illustrative side view of a portion of CSG 300, according to an embodiment. In particular, FIG. 9 shows front sub-stay 310, front main stay 320, back sub-stay 330, back main stay 340, and side stays 350 as they exist on that portion of CSG 300.

Figure 10D:
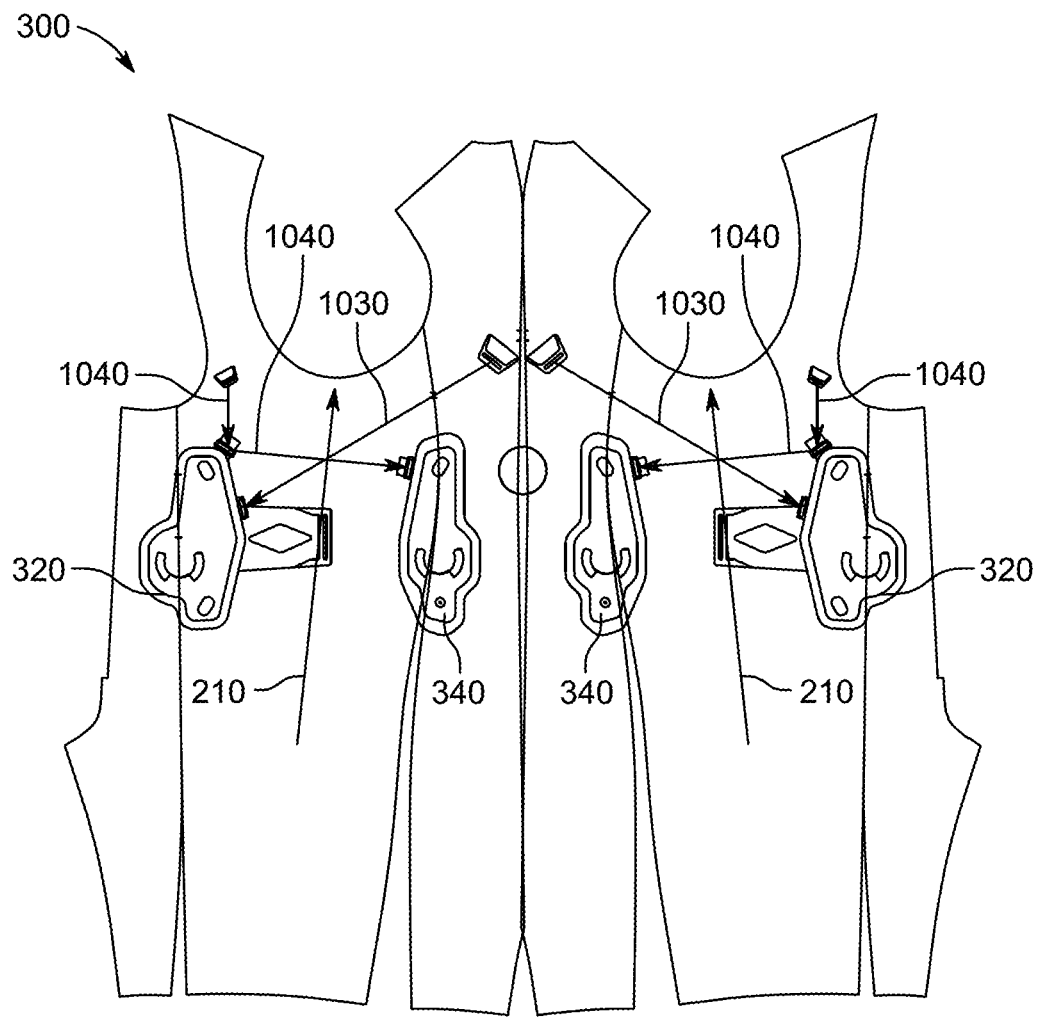
FIG. 10D shows the routing paths of webbings according to an embodiment.

FIGS. 10A-10C show illustrative front, back, and side view of shoulder system 1000 according to an embodiment. Shoulder system 1000 can include front straps 1010, fitter strips 1012, front buckles 1016, shoulder yoke 1020, yoke buckles 1022, yoke-to-front main stay webbing 1030, and front strap to back main stay webbing 1040. Front and back main stays 320 and 340 and buckles 324, 325 and 345 are also shown. Webbing 1030 originates from one of yoke buckles 1022 and wraps around the body towards front main stay 320 and is attached to buckle 325. Two instances of webbing 1030 exists in shoulder system 1000. Webbing 1040 originates at one of buckles 1014, passes through buckle 324 and terminated at buckle 345 on back main stay 340. Two instances of webbing 1040 exists in shoulder system 1000. FIG. 10D shows the routing paths of webbings 1030 and 1040.

FIGS. 11A-11C show different views of front strap 1010 of shoulder system 1000 according to an embodiment. FIG. 11A shows straps 1010. FIG. 11B shows the different components that of front strap 1010. In particular, FIG. 11 shows ripstop textile portion 1101, fitter textile portions 1102, and adhesive portions 1103. FIG. 11C shows how the different portions are stacked on top of each other to form front strap 1010. Ripstop textile portions discussed herein may be non-stretch materials. Fitter textile portions discussed herein refer to elastic materials.

Figure 12C:
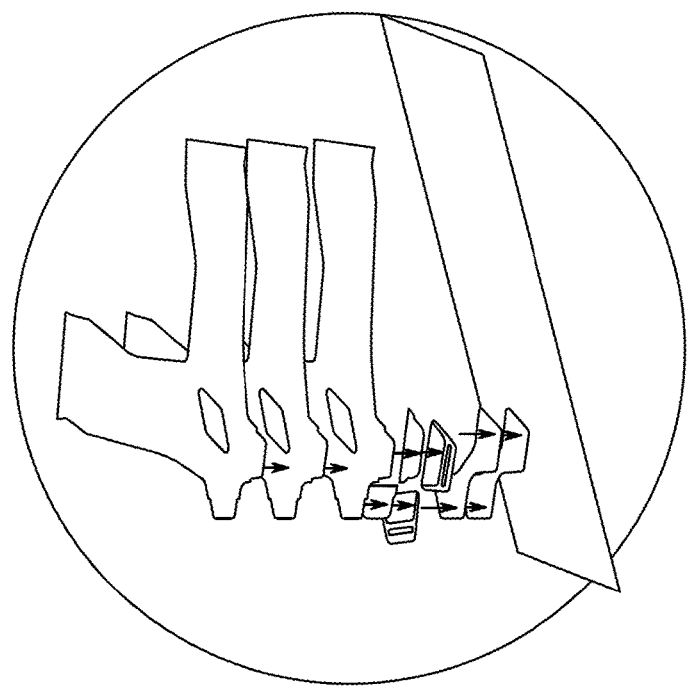
FIGS. 12A-12C show different views of shoulder yoke strap of a shoulder system according to an embodiment.
Figure 12B:
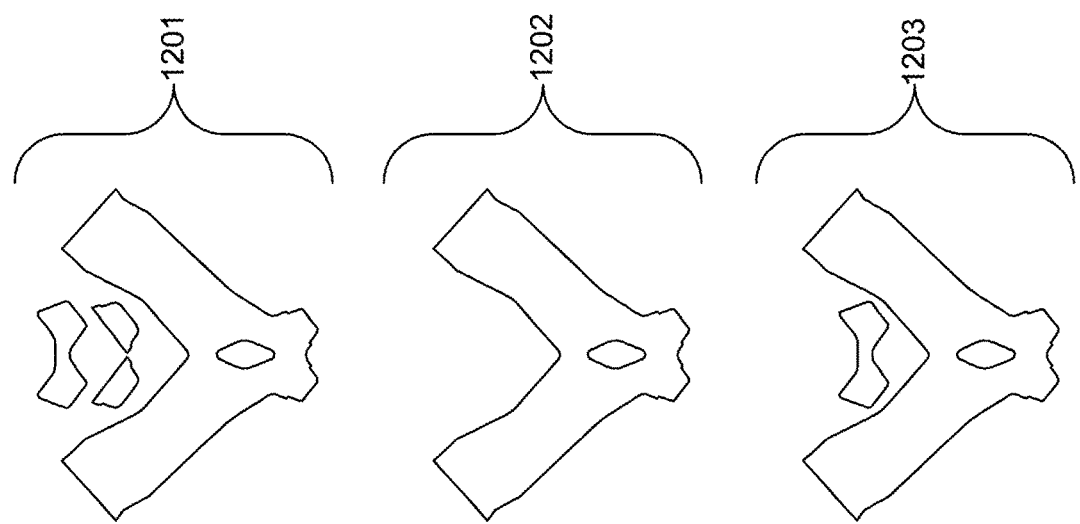
Figure 12A:
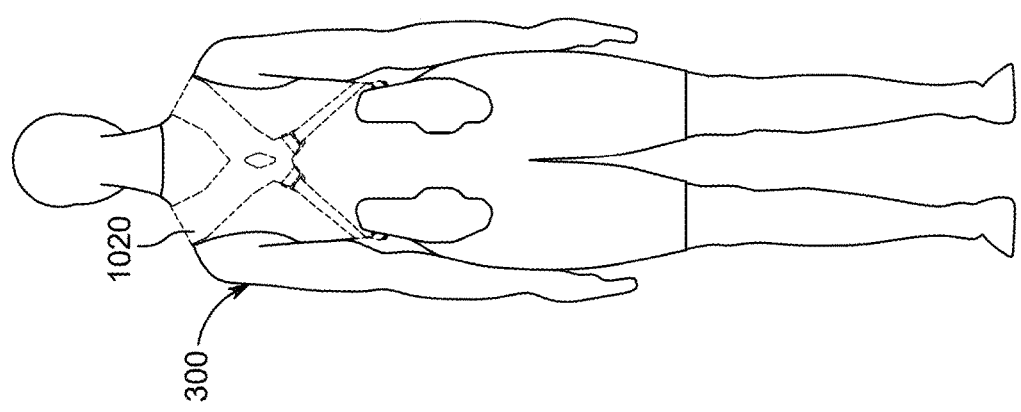

FIGS. 12A-12C show different views of shoulder yoke strap 1020 of shoulder system 1000 according to an embodiment. FIG. 12A shows yoke 1020 integrated with CSG 300. FIG. 12B shows adhesive portion 1201, fitter textile portions 1202, and ripstop portions 1203. FIG. 12C shows how portions 1201-1203 are stacked on top of each other form yoke 1020.

FIGS. 13A-13C show different illustrative views of tunnel system 1300 according to an embodiment. Tunnel system 1300 may be bonded to base layer 301 and include channels (not shown) that allow webbings 1030 and 1040 to pass from their respective origination points to their respective termination points. Webbings 1030 and 1040 may be routed through tunnel system 1300. Tunnel system 1300 keeps webbings 1030 and 1040 (not shown) close to the body and does not allow webbings 1030 and 1040 to flop around in an unwieldly manner or prevent the potential for snagging.

Figures 14A, 14B, 14C:
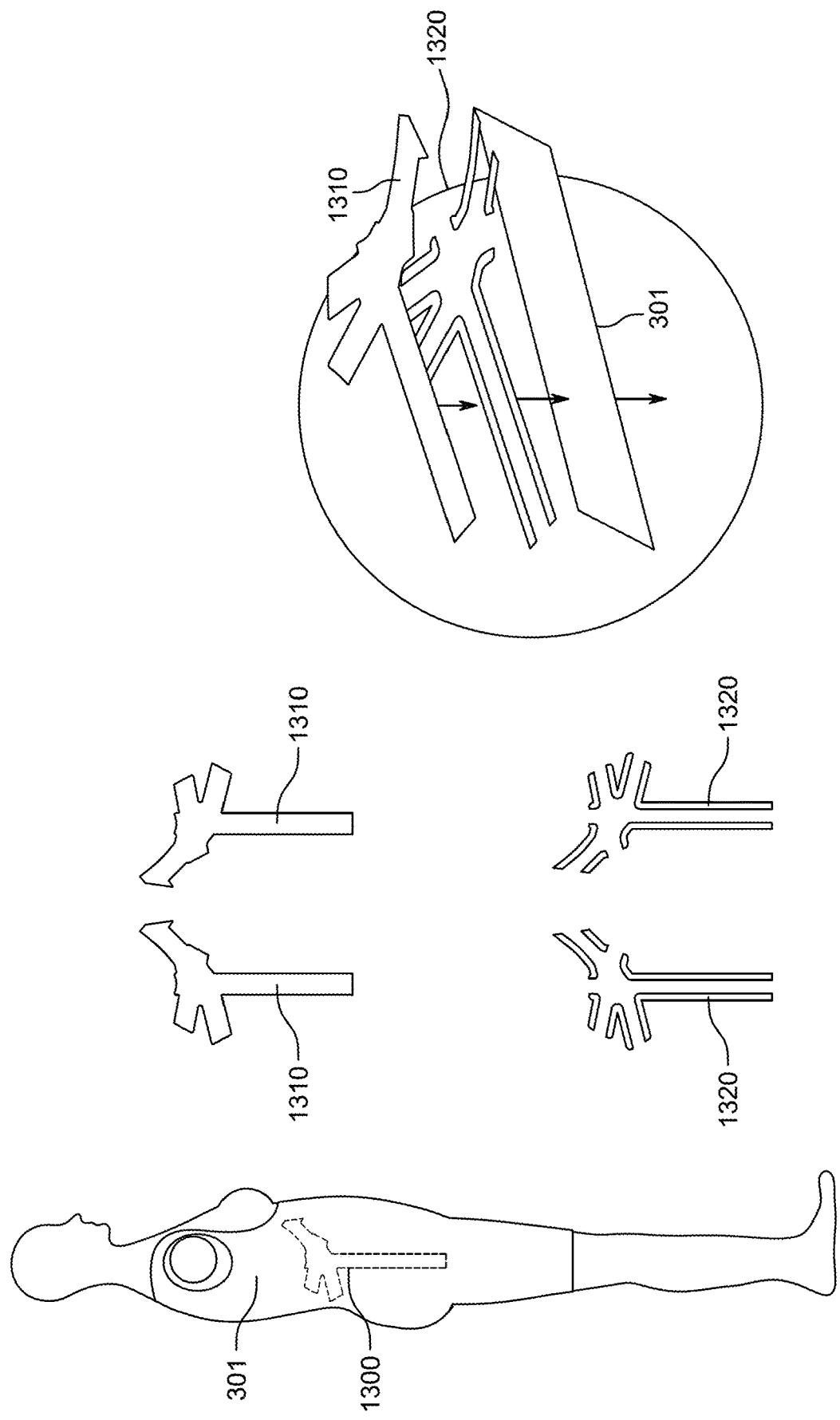
FIGS. 14A-14C shows different views of a tunnel system according to an embodiment.

FIGS. 14A-14C shows different views of tunnel system 1300 according to an embodiment. FIG. 14A shows approximate location of system 1300 on base layer 301. FIG. 14B shows textile portions 1310 and adhesive portions 1320. Adhesive portions 1320 include channels or tunnels through which webbing or line of extensions can pass through. FIG. 14C shows the stack up of system 1300. In particular, FIG. 14C shows adhesive portion 1320 sandwiched between textile portion 1310 and base layer 301.

Figure 15D:
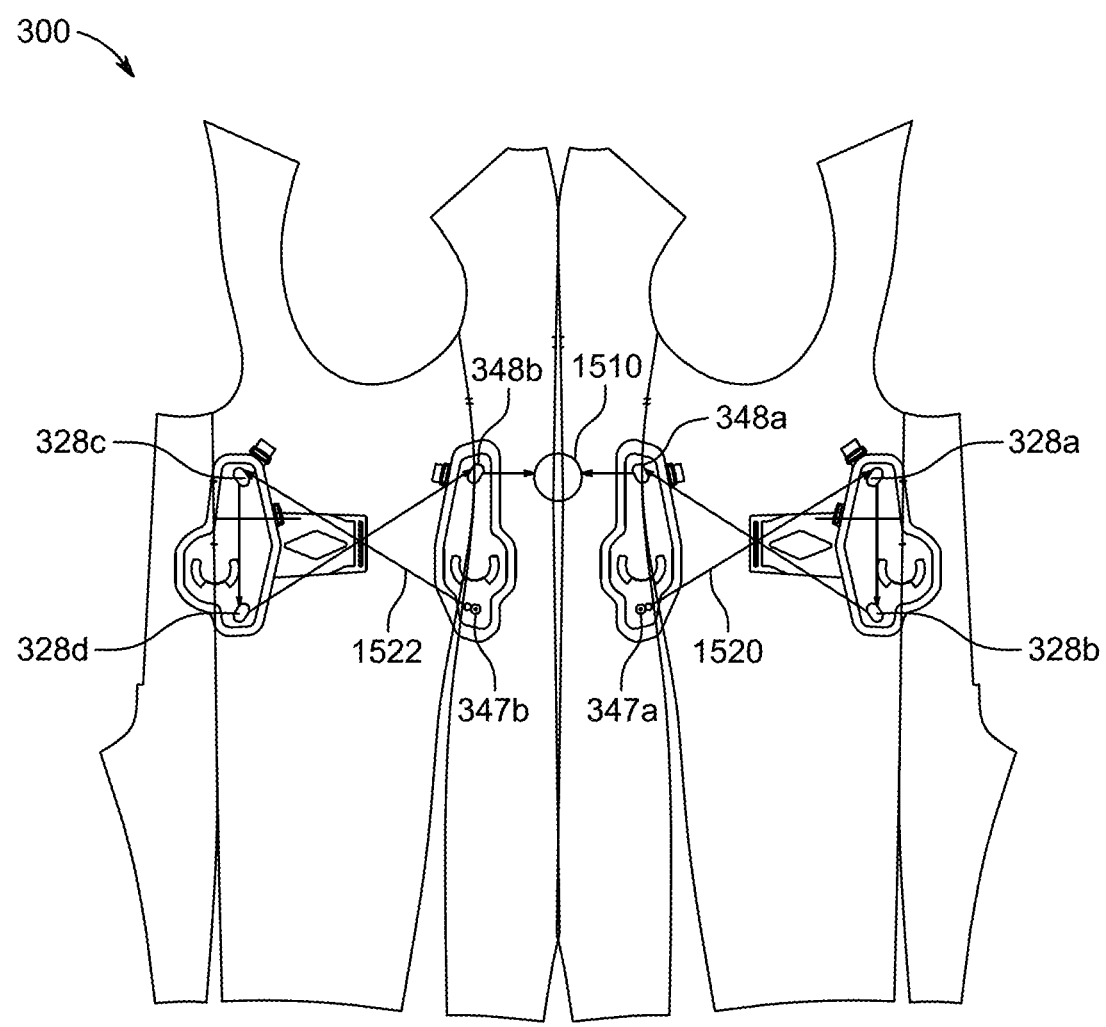
FIG. 15D shows the cord system with a core support grip in a flattened pattern according to an embodiment.
Figure 15E:
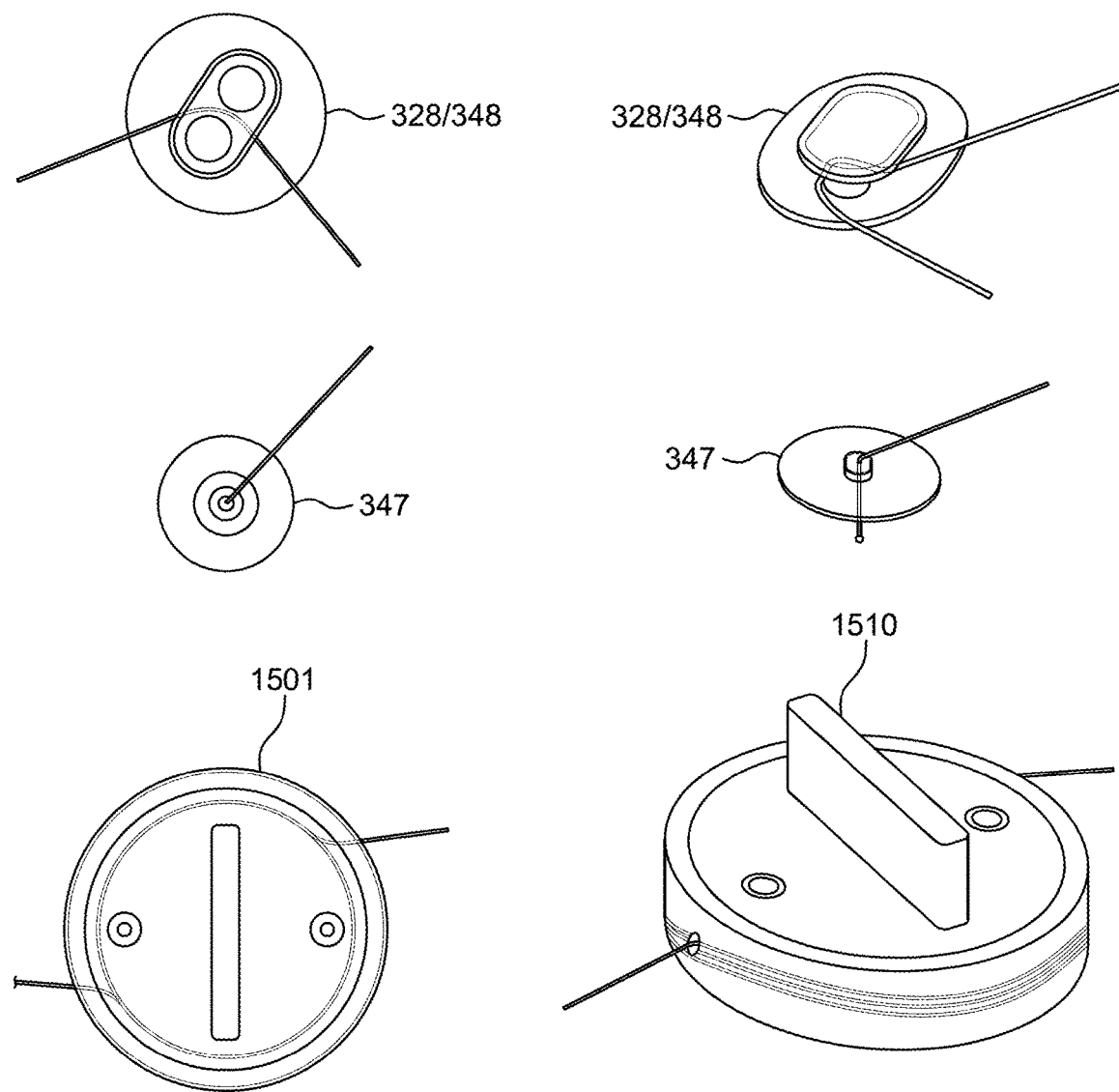
FIG. 15E shows different views of pass through ports, anchor points, and an adjustment member according to an embodiment.

FIGS. 15A-15C show illustrative front, back, and side views of cord system 1500 according to an embodiment. FIG. 15D shows cord system 1500 with CSG 300 in a flattened pattern according to an embodiment. Cord system 1500 includes adjustment member 1510 and cords 1520 and 1522. Cords 1520 and 1522 are routed through pass through ports 328 and 348 and secured to anchor points 357 and adjustment member 1510. In particular, cord 1520 may originate at a first anchor point 357a (shown here on the right side of the person), and is routed around the hip towards pass through port 328a, and then routed down through pass through port 328b, and then is routed back around the hip (such that is crisscrosses itself) and routed through pass through port 348a and is terminated at adjustment member 1510. Cord 1522 may originate at anchor point 347b (shown here on the left side of the person), and is routed around the hip towards pass through port 328c, and then routed down through pass through port 328d, and then is routed back around the hip (such that is crisscrosses itself) and routed through pass through port 348b and is terminated at adjustment member 1510. Cords 1520 and 1522 provide tensioning of CSG 300 and the adjustment member 1510 is used to adjust the tensioning of cords 1520 and 1522. Adjustment member 1510 can be a circular mechanism in which cords 1520 and 1522 wrap around a core, which can be locked in place. For example, a user may turn the core clockwise to increase tension or turn counter-clockwise to decrease tension. FIG. 15E shows different views of pass through ports 328 and 348, anchor points 357, and adjustment member 1510.

It should be understood that cord system 1500 can be integrated with one or more motorized mechanisms that are able to adjust the tension of cords 1520 and 1522. For example, cords 1520 and 1522 can be connected to one or more FLAs. In some embodiments, cord system 1500 can be replaced with a tensioning system.

FIGS. 16A-16C show illustrative front, back, and side views of thigh grip members 1600, according to an embodiment. Thigh grip members 1600 are secured to the thigh regions of the wearer and provide anchor support for securing power layer segments thereto. Each thigh grip member 1600 includes sub-stack 1610, main thigh stack-up 1630, and line-of-extension (LOE) interconnect 1680. LOE 1680 may offset weight of a power layer segment attached to grip member 1600 and can be adjusted for user height and is designed to not extend during use. Sub-stack 1610 is positioned at the front of thighs. Main thigh-stack up 1630 wraps around the thigh and interlocks with itself. LOE interconnect 1680 is coupled to buckle 215 of LOE 210. Members 1600 also include snaps 1770 for securing power layer components to members 1600.

Figure 17C:
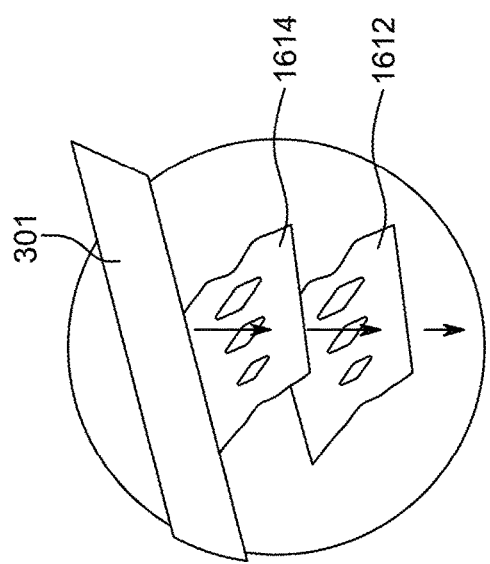
FIGS. 17A-17I show different views of main thigh stack-up according to an embodiment.
Figure 17B:
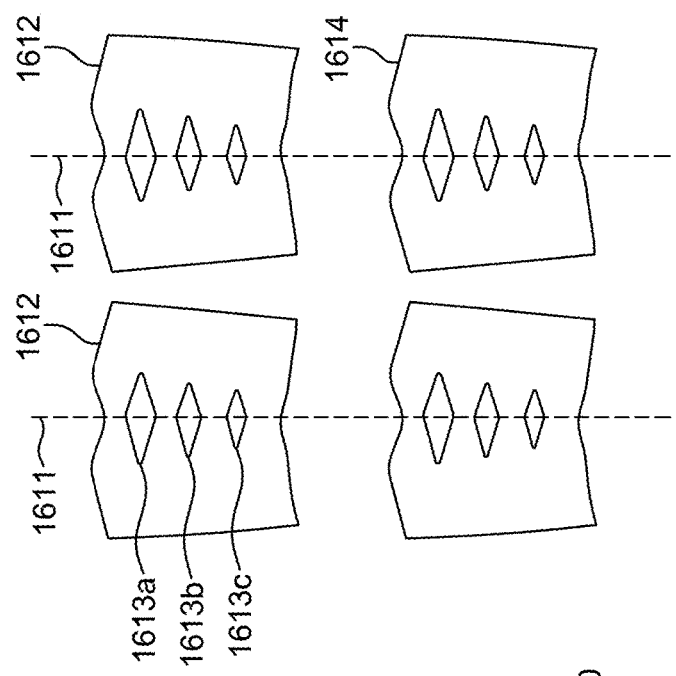
Figure 17A:
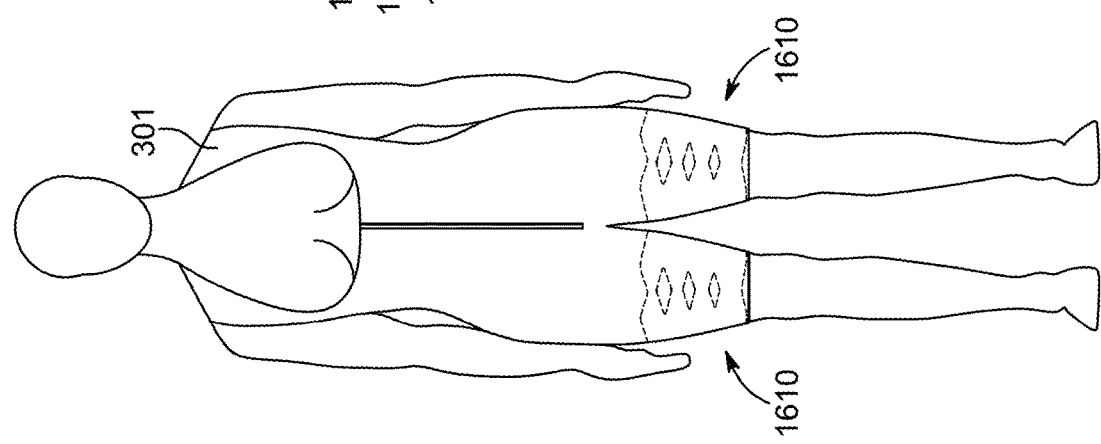
Figure 17D:
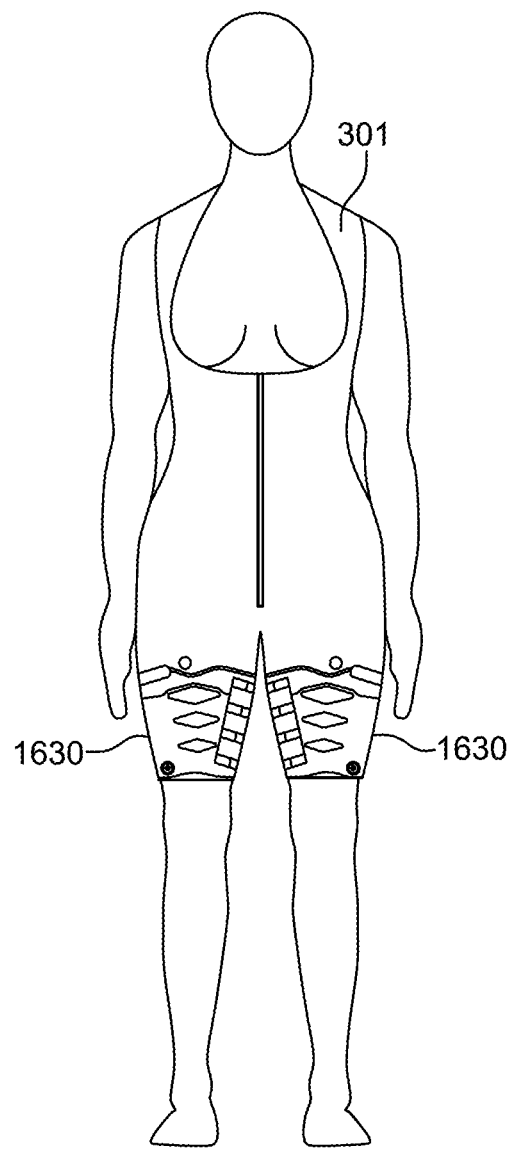
Figure 17E:
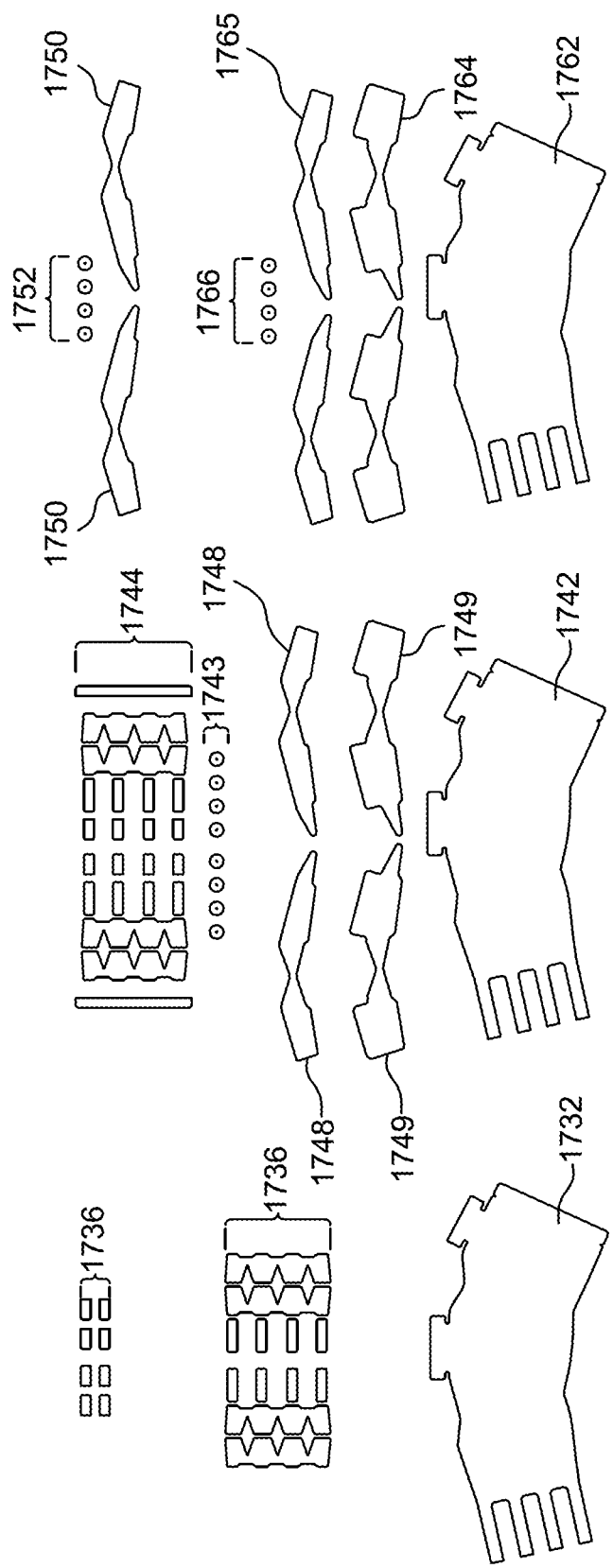

FIGS. 17A-17C show different views of sub-stack 1610 according to an embodiment. FIG. 17A shows the positioning of sub-stack 1610 as it positioned on base layer 301. Sub-stack 1610 may exist on the underside of base layer 301 and directly interface with the skin of the wearer. FIG. 5B shows that sub-stack 1610 includes textile portion 1612 and adhesive portion 1614. Textile portion 1612 may have cutouts 1613a-c that are positioned along center axis 1611. Cutouts 1613a-c may be sized differently, with cutout 1613a being larger than cutout 1613b, which is larger than cutout 1613c. Adhesive portion 1614 may have cutouts 1615a-c that are positioned along center axis 1611. Cutouts 1615a-c may be sized exactly the same as cutouts 1615a-c, respectively. FIG. 17C shows that stack up 1610 is arranged such that adhesive portion 1614 is sandwiched between base layer 301 and textile portion 1612. Stack up 1610 can be created using a multi process that uses engineered FIGS. 17D-17I show different views of main thigh stack-up 1630 according to an embodiment. FIG. 17D shows placement of thigh stack-up 1630 with respect base layer 301. A portion of thigh stack-up 1630 may line up with sub-stack 1610. In particular, the cutouts of thigh stack-up 1630 align with the cutouts of sub-stack 1610. FIG. 17E shows different layers that make up the composition of thigh stack-up 1630. These layers can include rip stop textile 1732, loop Velcro portions 1734, hook Velcro portions 1736, adhesive portions 1742, adhesive portions 1743, adhesive portions 1744, adhesive portions 1748 and 1749, flexible polyurethane portions 1750 and 1752, and fitter textile portions 1762, 1764, 1765, and 1766.

Figure 17F:
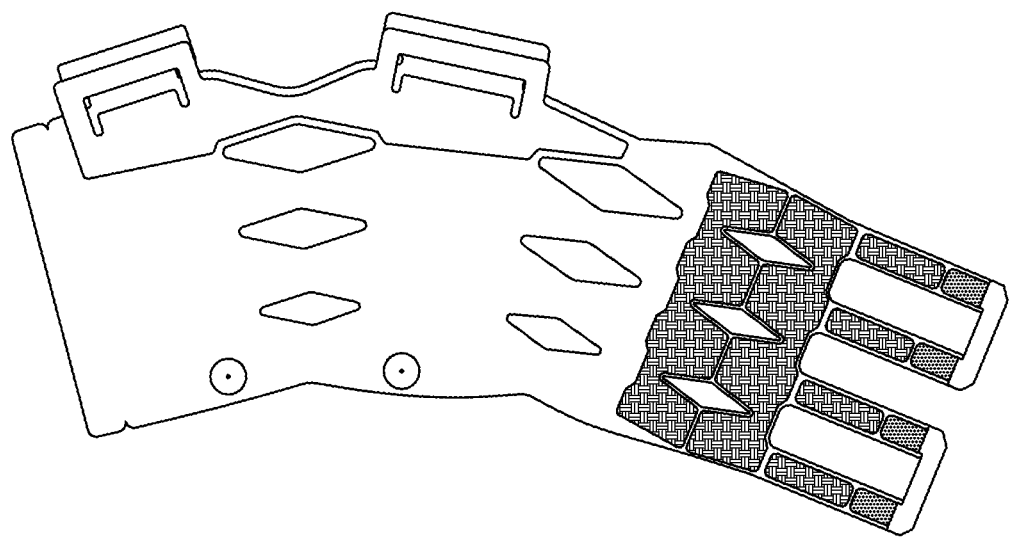
Figure 17G:
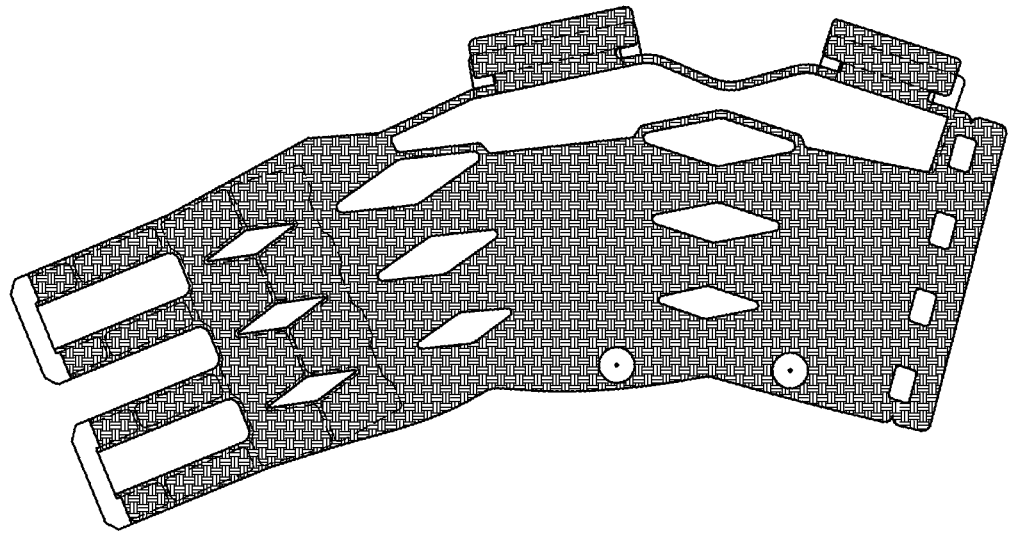
Figure 17H:
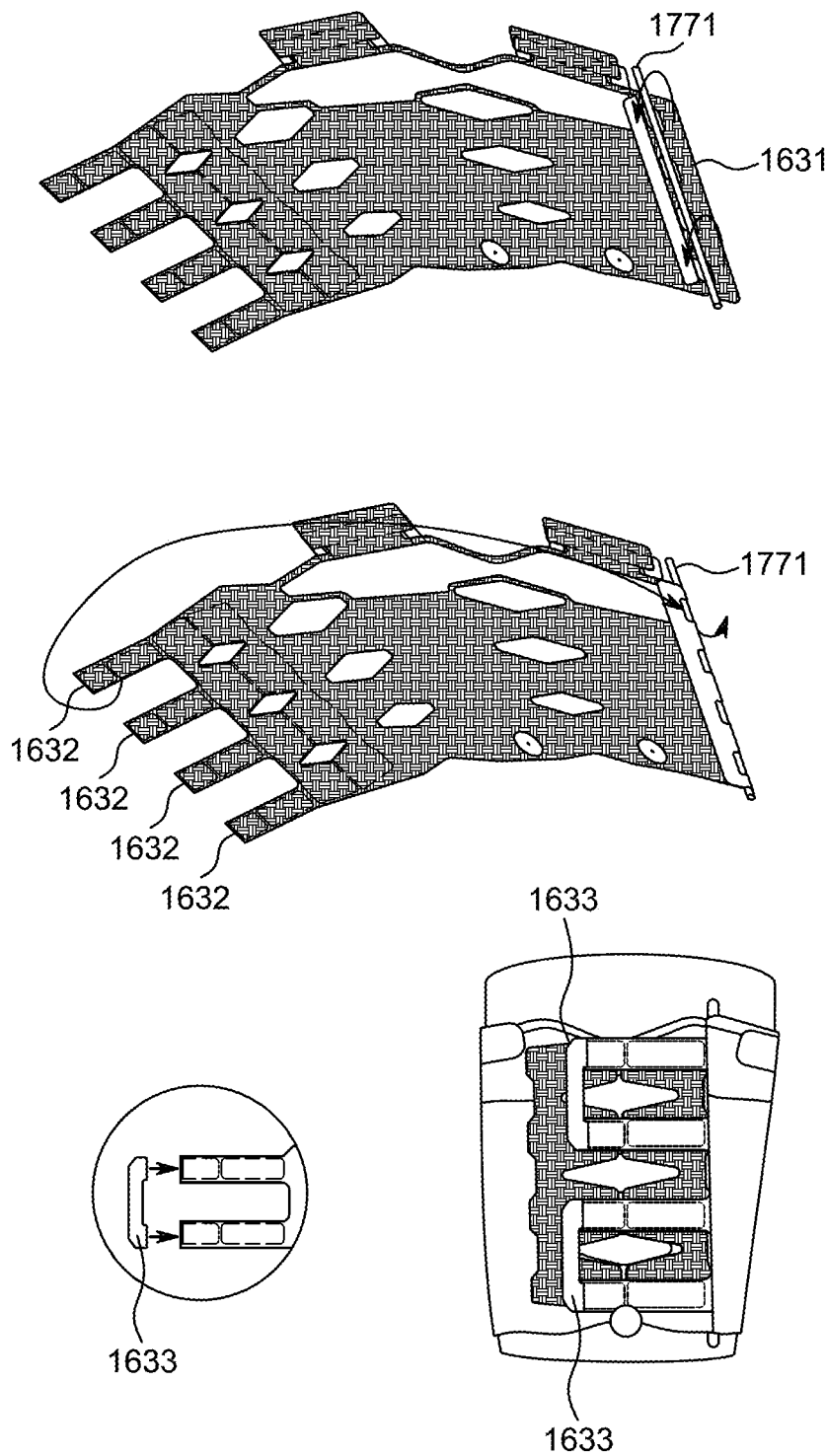
Figure 17I:
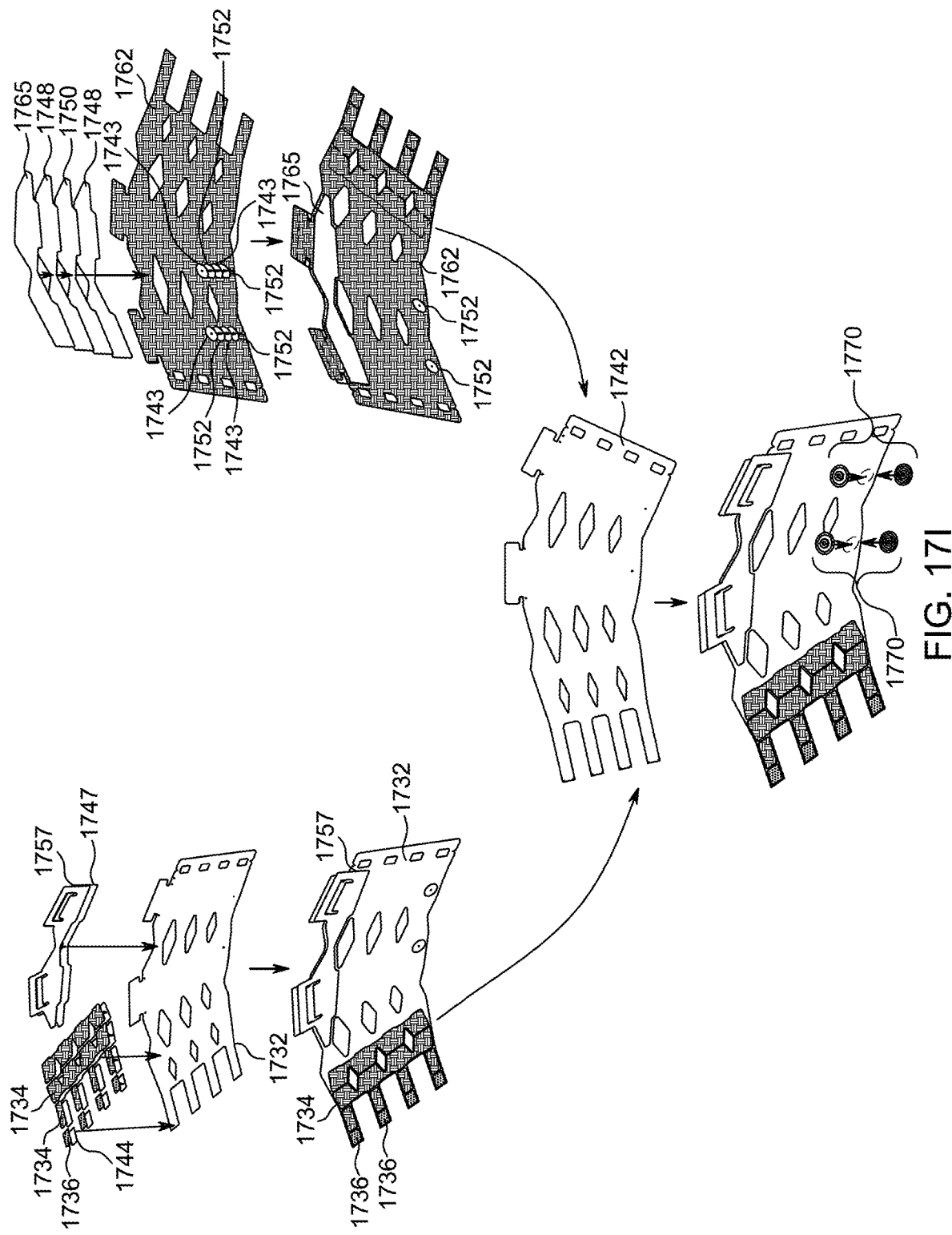

FIG. 17I shows illustrative assembly of thigh stack-up 1630. The left side of FIG. 17I shows front side of the grip in which adhesive layers 1744 and 1747 are placed on top of rip stop textile 1732. Loop portions 1734 and hook portions 1736 are placed on top of adhesive layers 1744. Semi-rigid member 1757 is placed on top of adhesive layer 1747. The right side of FIG. 17I shows the back side of the grip in which adhesive layer 1748 is mounted to textile portion 1762, and portion 1750 is mounted on top of layer 1748. Another adhesive layer 1748 is mounted on top of portion 1750 and textile portion 1765 is mounted on top of adhesive 1748. Adhesive layer 1743 is mounted to textile portion 1762, and portion 1752 is mounted on top of that. The next step shows that rip stop textile 1732 is mated to textile portion 1762 via adhesive layer 1742. After rip stop textile 1732 is mated to textile portion 1762, snaps 1770 (e.g., male snaps) are secured to the portion of stack-up 1630 including adhesive portions 1743 and portions 1752.

FIG. 17F and FIG. 17G show respective front and back sides of thigh grip 1630 after assembly steps in FIG. 17I are completed.

FIG. 17H shows how a grip closure assembly is constructed. Tube 1771 is placed as shown, and flap portion 1631 folds over tube 1771 and is bonded to portion 1762. Each of fingers 1632 are slipped around tube 1771 and pairs of fingers 1632 are capped with bridge member 1633. Bridge member 1632 prevents flap portions 1632 from sliding away from tube 1771.

FIG. 18 shows steps for forming thigh grip pockets. Both front and back sides of grip member 1630 are shown for each step. Starting at step 1801, flap portions 1810 are folded and passed through windows 1811. The portion of flap portions 1810 that passed through respective windows 1811 are bonded to ripstop textile 1732 via an adhesive, as shown in step 1802. In step 1803, window portions 1811 are folded towards textile portion 1762 and bonded thereto. Step 1804 shows the end result. Flap portions 1810 form pockets that provide toe-ins for power layer components to be secured to thigh grip member 1600. The power layer component can be secured to snaps 1770.

Figure 19D:
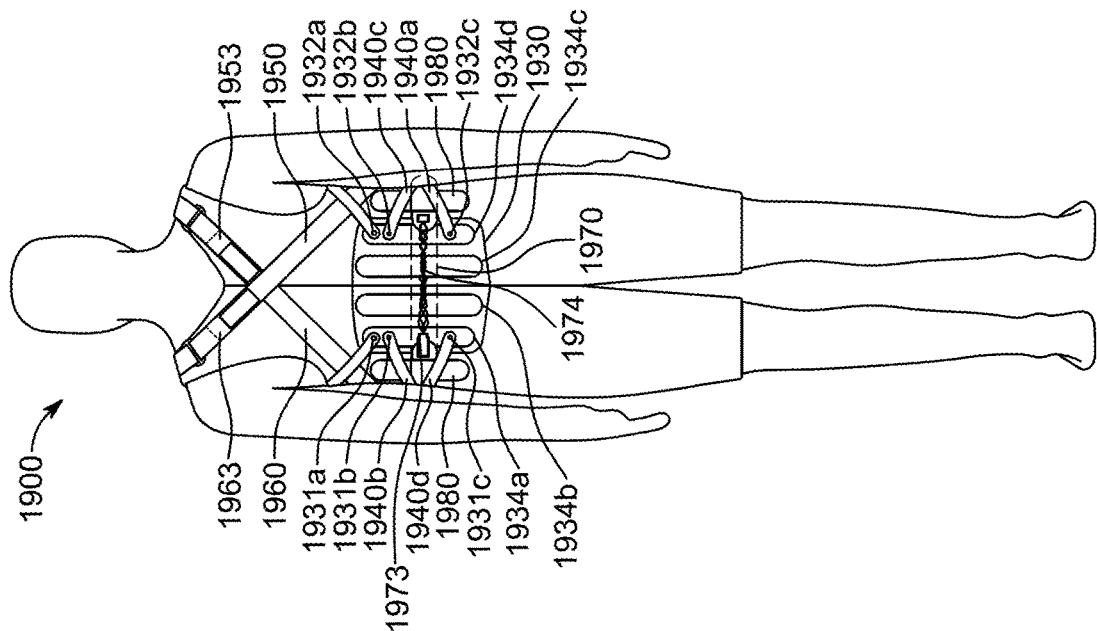
FIGS. 19C and 19D shows front and back views of core support grip positioned on an exosuit according to an embodiment.
Figure 19C:
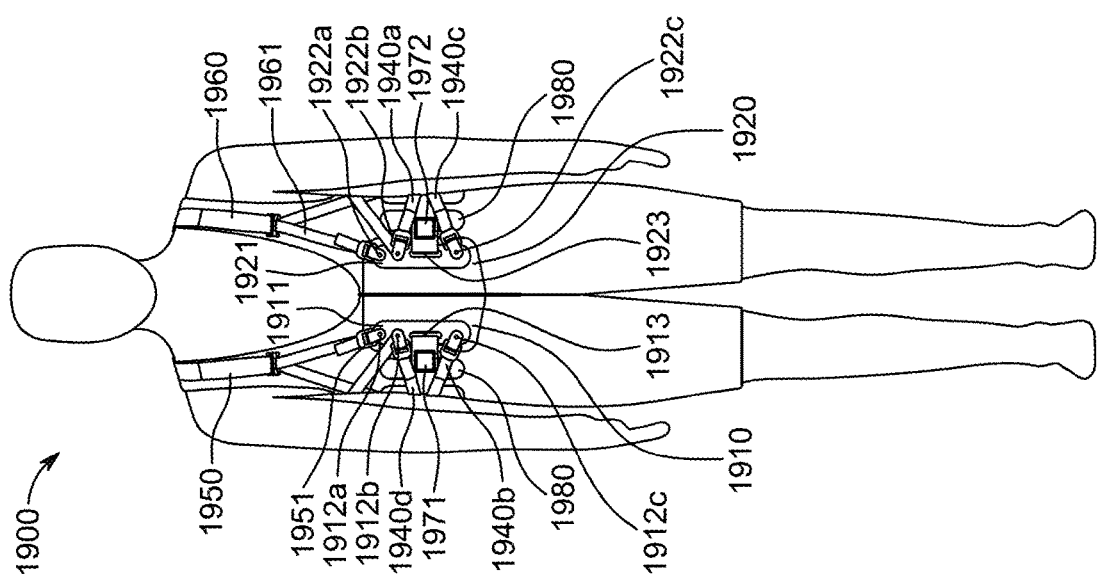

FIG. 19A-26B show several illustrative views of another core support grip (CSG 1900) and components thereof according to an embodiment. CSG 1900 may integrate use of vertical stays to distribute loads across the user's core. FIGS. 19A and 19B show front and back views of CSG 1900, and FIGS. 19C and 19D shows front and back views of CSG 1900 positioned on an exosuit. CSG 1900 can include front panels 1910 and 1920, back panel 1930, cross bands 1940*a-d*, shoulder straps 1950 and 1960, tension system 1970, and side stays 1980. Front panel 1910 can include vertical stay 1911, anchor points 1912*a-c*, and tension interfacing member 1913. Front panel 1920 can include vertical stay 1921, anchor points 1922*a-c*, and tension interfacing member 1923. Back panel 1930 can include anchor points 1931*a-c*, anchor points 1932*a-c*, vertical stays 1934*a-d*. Cross band 1940*a* can be connected to anchor points 1922*b* and 1932*c*. Cross band 1941*b* can be connected to anchor points 1931*b* and 1912*c*. Cross band 1941*c* can be connected to anchor points 1922*c* and 1932*b*. Cross band 1941*d* can be connected to anchor points 1931*c* and 1912*a*. Shoulder strap 1950 can include adjustable strap member 1951, which is connected to anchor point 1912*a* and anchor point 1931*a*. Shoulder strap 1950 can include adjustable back strap member 1953, which is connected to anchor point 1912*b*. Shoulder strap 1960 can include adjustable strap member 1961, which is connected to anchor point 1922*a* and anchor point 1932*a*. Shoulder strap 1960 can include adjustable back strap member 1963, which is connected to anchor point 1922*b*. Shoulder straps 1950 and 1960 provide load distribution from right to left, front and back, and allow twist and lean.

Front panels 1910 and 1920, and back panel 1930 may be constructed from several non-stretch fabrics that are integrated into the base layer and that sandwich respective stays 1910, 1920, and 1934. For example, Stays 1911, 1921, and 1934, and side stays 1980 are designed to distribute squeeze load to a broader area, for example, to protect soft tissue from being compressed too much and to prevent pinching of the core region. Stays 1911, 1921, 1934, and 1980 may be constructed from a rigid material such as plastic, a composition of layers, for example, including fabric and plastic. Front stays 1911 and 1921 can serve as an LDM for flexor FLAs (not shown) and back stay 1930 can serve as an LDM for extensor FLAs (not shown). Cross band 1940*a-d* can counteract loads being applied by the flexor and extensor loads.

Tension system 1970 can include belt segments 1971 and 1972, motor 1973, twisted string 1974. Belt segment 1971 may be connected to tension interfacing member 1913 to motor 1973. Belt segment 1972 may be connected to tension interfacing member 1923 and twisted string 1974. When motor 1973 shortens twisted string 1974, this pulls belt segments 1971 and 1972 together and cause forces to be applied to the core via the CSG 1900.

FIGS. 20A-20C show CSG 1900, but without shoulder straps 1950 and 1960, and anchor points 1912*a*. 1922*a*, 1931*a*, and 1932*a* removed. FIG. 20C shows side stays 1980 more clearly.

Figure 21:
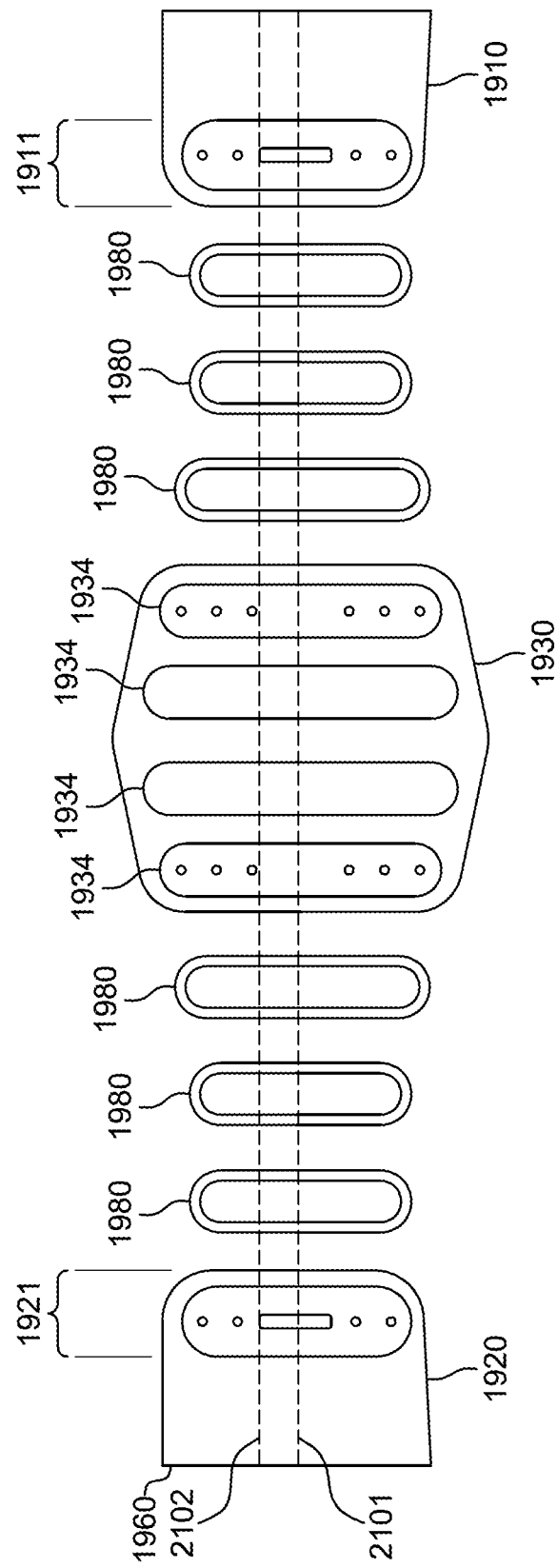
FIG. 21 shows illustrative arrangement of panels and stays according to an embodiment.
Figure 24:
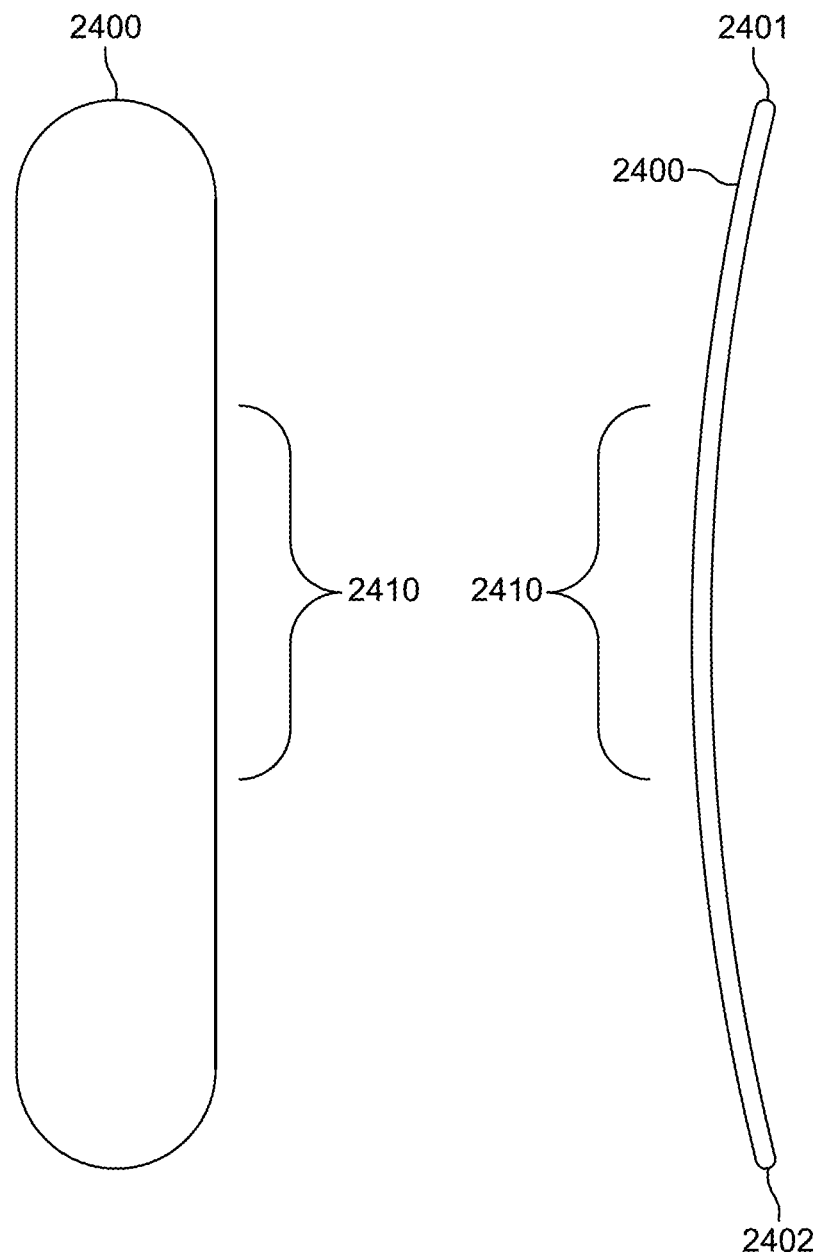
FIG. 24 shows illustrative front and side views of a vertical stay according to an embodiment.

FIG. 21 shows illustrative arrangement of panels and stays according to an embodiment. The number and size of stays may vary depending on the size of the user intended to don the exosuit. For example, a woman may have fewer side stays than a man, and the height of the stays may be less than those used for a man. In some embodiments, center axis 2101 of CSG 1900 may be offset with respect to waistline 2102. In particular, center axis 2101 may be positioned below waistline 2102 (e.g., about an inch). The distance between stays may depend on size of the exosuit (and by extension, the size of the person wearing the exosuit). It may be desirable for the stays to be evenly spaced apart. In some embodiments, there may be minimum spacing requirements (e.g., at least 1 inch apart) and maximum spacing requirements (e.g., more than 1.75 inches apart). The stays may be a flexible material that may have a natural curve, such as that shown in FIG. 24. The stays may have an engineering curve to target forces in an un-uniformed manner such as a bow shape or a C shape. FIG. 24 shows an illustrative stay 2400 according to an embodiment.

FIG. 22 shows an illustrative front stay 1911 according to an embodiment. Stay 1911 can include anchor points 1912*a-d*, and tension interfacing member 1913. Anchor point 1912*d* is not shown in FIG. 19A and may serve as a flexor anchor point. FIG. 23 shows an illustrative back stay 1931 according to an embodiment. Stay 1931 can include anchor points 1934*a-f*. Anchor points 1934*d-f* are not shown in FIG.

19B. Anchor point 1934*d* may be an extensor anchor point. Anchor points 1934*e-f* can be interface locations for tension system 1970.

FIG. 24 shows illustrative front and side views of a stay 2400 according to an embodiment. Stay 2400 may have a bow like curve that enables ends 2401 and 2402 to press into the body when they are attached to front and back panels. A tensioning system (not shown) may apply pressure to a center region 2410 of stay 2400. In addition to, or alternatively, the tensioning system may be able to apply pressure to ends 2401 and 2402.

Figure 25:
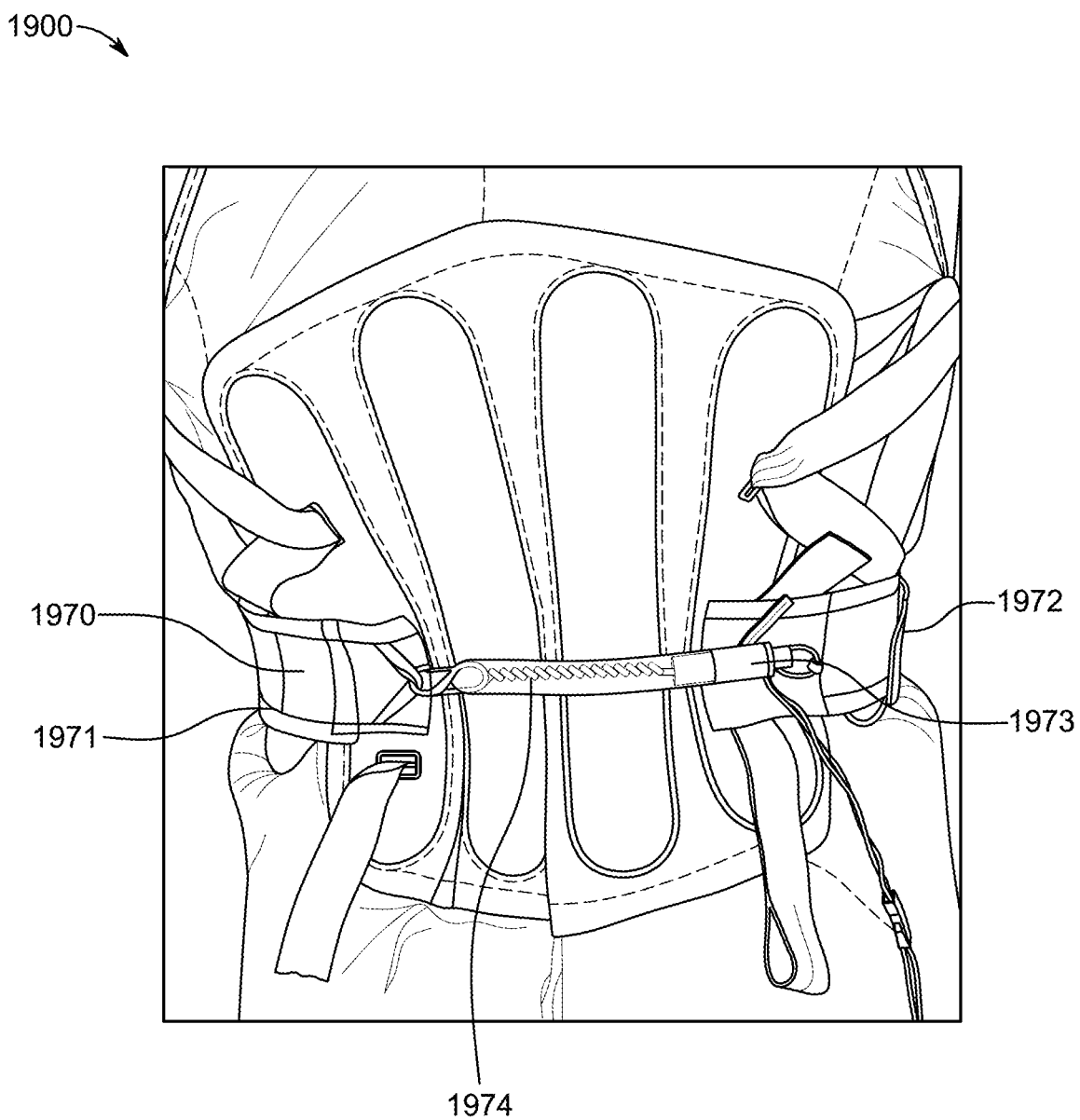
FIG. 25 shows an example of a tensioning system interfacing with a core support grip according to an embodiment.
Figure 26A:
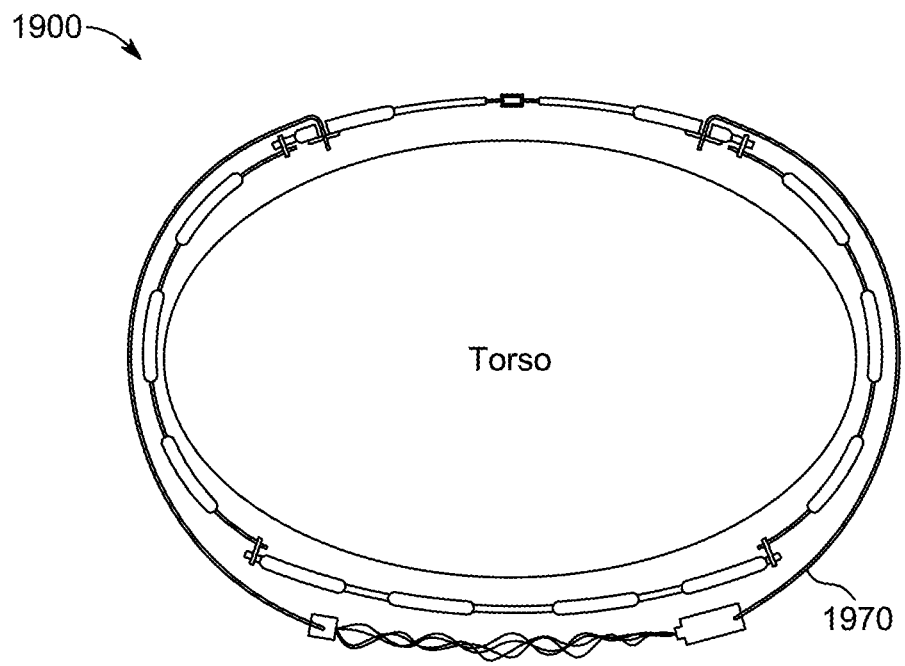
FIGS. 26A and 26B show core support grip and a tensioning system in respective relaxed and constricted states, according to an embodiment.
Figure 26B:
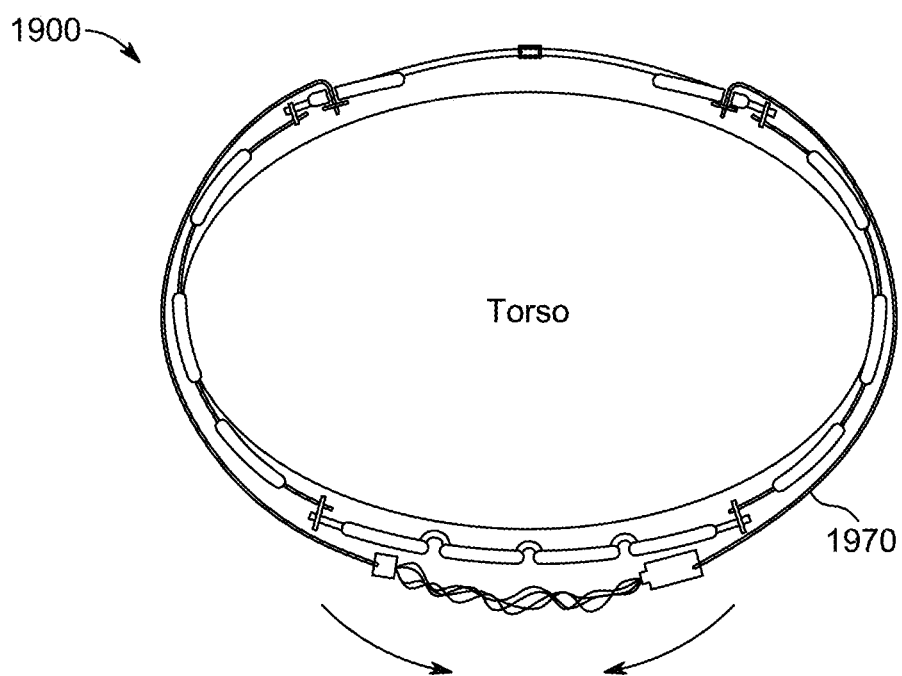

FIG. 25 shows an example of tensioning system 1970 interfacing with CSG 1900 according to an embodiment. Tensioning system 1970 is shown to be in a contracted state in which pressure is being applied to a center region of CSG 1900. When tensioning system 1970 is contracted, inwardly facing forces are applied around the core of the person. This is illustrated in FIGS. 26A and 26B, which show CSG 1900 and tensioning system 1970 in respective relaxed and constricted states. Tensioning system 1970 is merely illustrative and that any suitable tensioning system may be used. For example, commonly owned U.S. Publication No. 2019/0160651 provides several examples of tensioning systems that may be used connection with core support grips according to embodiments discussed here. U.S. Publication No. 2019/0160651 is incorporated by reference in its entirety.

Figure 27A:
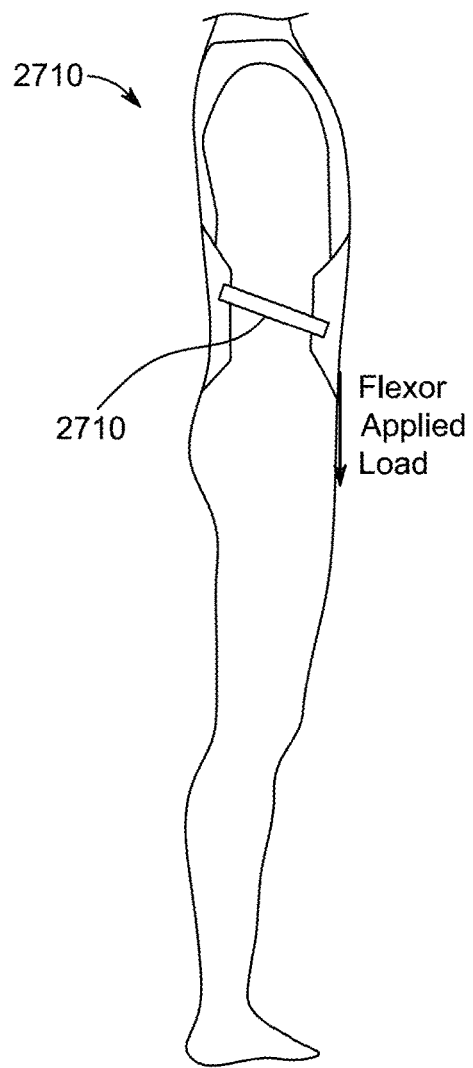
FIGS. 27A-B show side views of a core support grip according to an embodiment.
Figure 27B:
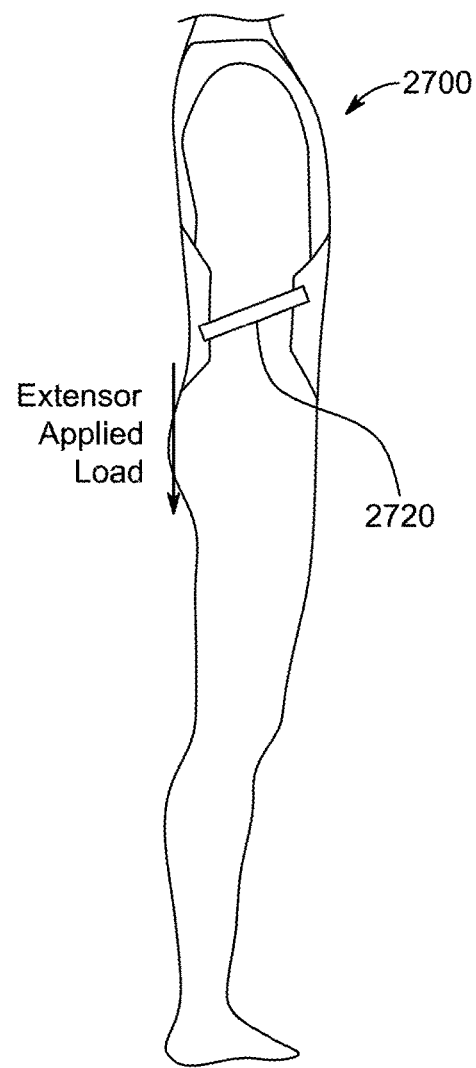

FIGS. 27A-B show side views of a CSG 2700 according to an embodiment. FIG. 27A shows CSG 2700 with cross band 2710 and FIG. 27B shows CSG 2700 with cross band 2720. When a flexor load is being applied, a portion of the flexor load is borne by the front region of CSG 2700, and a portion of the flexor load is transferred to the back region of CSG 2700 via cross band 2710. The degree to which loads are applied can depend on the internal stiction and the tightness of the core support. When an extensor load is being applied, a portion of the extensor load is borne by the back region of CSG 2700, and a portion of the extensor load is transferred to the front region of CSG 2700 via cross band 2720. Cross band 2720 may bear a portion of the pressure.

An exosuit can be operated by electronic controllers disposed on or within the exosuit or in wireless or wired communication with the exosuit. The electronic controllers can be configured in a variety of ways to operate the exosuit and to enable functions of the exosuit. The electronic controllers can access and execute computer-readable programs that are stored in elements of the exosuit or in other systems that are in direct or indirect communications with the exosuit. The computer-readable programs can describe methods for operating the exosuit or can describe other operations relating to a exosuit or to a wearer of a exosuit.

Figure 28:
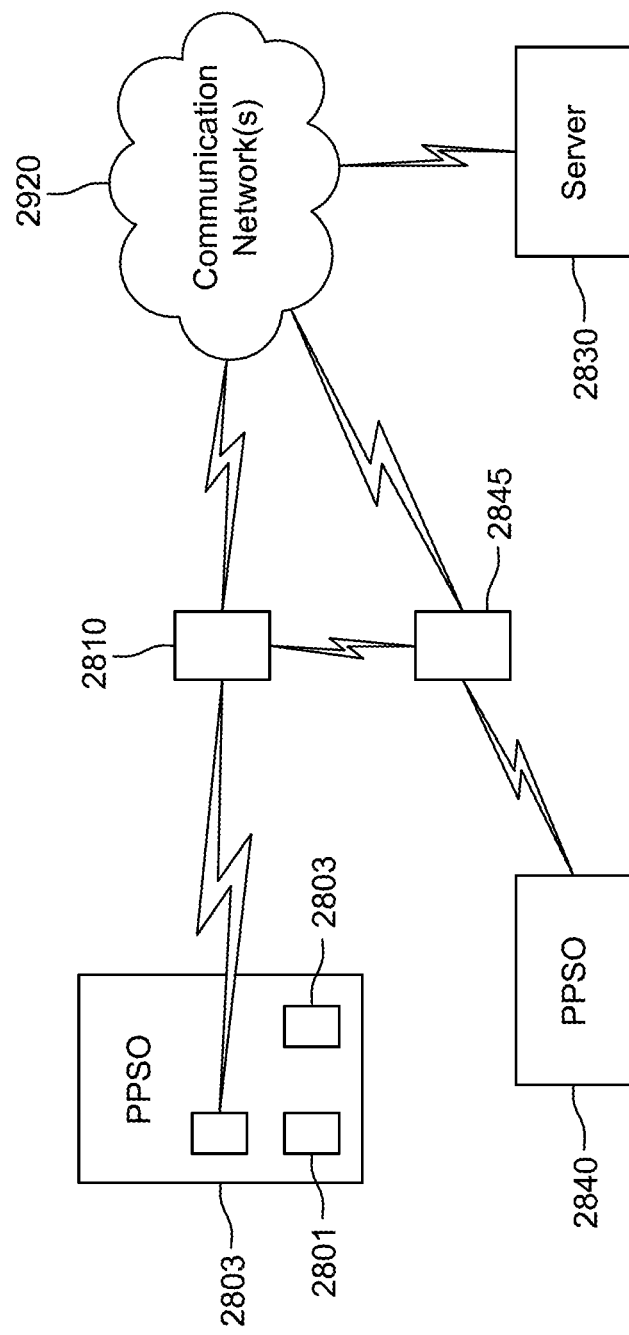
FIG. 28 illustrates an example exosuit according to an embodiment.

FIG. 28 illustrates an example exosuit 2800 that includes actuators 2801, sensors 2803, and a controller configured to operate elements of exosuit 2800 (e.g., 2801, 2803) to enable functions of the exosuit 2800. The controller 2805 is configured to communicate wirelessly with a user interface 2810. The user interface 2810 is configured to present information to a user (e.g., a wearer of the exosuit 2800) and to the controller 2805 of the flexible exosuit or to other systems. The user interface 2810 can be involved in controlling and/or accessing information from elements of the exosuit 2800. For example, an application being executed by the user interface 2810 can access data from the sensors 2803, calculate an operation (e.g., to apply dorsiflexion stretch) of the actuators 2801, and transmit the calculated operation to the exosuit 2800. The user interface 2810 can additionally be configured to enable other functions; for example, the user interface 2810 can be configured to be used as a cellular telephone, a portable computer, an entertainment device, or to operate according to other applications.

The user interface 2810 can be configured to be removably mounted to the exosuit 2800 (e.g., by straps, magnets, Velcro, charging and/or data cables). Alternatively, the user interface 2810 can be configured as a part of the exosuit 2800 and not to be removed during normal operation. In some examples, a user interface can be incorporated as part of the exosuit 2800 (e.g., a touchscreen integrated into a sleeve of the exosuit 2800) and can be used to control and/or access information about the exosuit 2800 in addition to using the user interface 2810 to control and/or access information about the exosuit 2800. In some examples, the controller 2805 or other elements of the exosuit 2800 are configured to enable wireless or wired communication according to a standard protocol (e.g., Bluetooth, ZigBee, WiFi, LTE or other cellular standards, IRdA, Ethernet) such that a variety of systems and devices can be made to operate as the user interface 2810 when configured with complementary communications elements and computer-readable programs to enable such functionality.

The exosuit 2800 can be configured as described in example embodiments herein or in other ways according to an application. The exosuit 2800 can be operated to enable a variety of applications. The exosuit 2800 can be operated to enhance the strength of a wearer by detecting motions of the wearer (e.g., using sensors 2803) and responsively applying torques and/or forces to the body of the wearer (e.g., using actuators 2801) to increase the forces the wearer is able to apply to his/her body and/or environment. The exosuit 2800 can be operated to train a wearer to perform certain physical activities. For example, the exosuit 2800 can be operated to enable rehabilitative therapy of a wearer. The exosuit 2800 can operate to amplify motions and/or forces produced by a wearer undergoing therapy in order to enable the wearer to successfully complete a program of rehabilitative therapy. Additionally or alternatively, the exosuit 2800 can be operated to prohibit disordered movements of the wearer and/or to use the actuators 2801 and/or other elements (e.g., haptic feedback elements) to indicate to the wearer a motion or action to perform and/or motions or actions that should not be performed or that should be terminated. Similarly, other programs of physical training (e.g., dancing, skating, other athletic activities, vocational training) can be enabled by operation of the exosuit 2800 to detect motions, torques, or forces generated by a wearer and/or to apply forces, torques, or other haptic feedback to the wearer. Other applications of the exosuit 2800 and/or user interface 2810 are anticipated.

The user interface 2810 can additionally communicate with communications network(s) 2820. For example, the user interface 2810 can include a WiFi radio, an LTE transceiver or other cellular communications equipment, a wired modem, or some other elements to enable the user interface 2810 and exosuit 2800 to communicate with the Internet. The user interface 2810 can communicate through the communications network 2820 with a server 2830. Communication with the server 2830 can enable functions of the user interface 2810 and exosuit 2800. In some examples, the user interface 2810 can upload telemetry data (e.g., location, configuration of elements 2801, 2803 of the exosuit 2800, physiological data about a wearer of the exosuit 2800) to the server 2830.

In some examples, the server 2830 can be configured to control and/or access information from elements of the exosuit 2800 (e.g., 2801, 2803) to enable some application of the exosuit 2800. For example, the server 2830 can operate elements of the exosuit 2800 to move a wearer out of a dangerous situation if the wearer was injured, unconscious, or otherwise unable to move themselves and/or operate the exosuit 2800 and user interface 2810 to move themselves out of the dangerous situation. Other applications of a server in communications with a exosuit are anticipated.

The user interface 2810 can be configured to communicate with a second user interface 2845 in communication with and configured to operate a second flexible exosuit 2840. Such communication can be direct (e.g., using radio transceivers or other elements to transmit and receive information over a direct wireless or wired link between the user interface 2810 and the second user interface 2845). Additionally or alternatively, communication between the user interface 2810 and the second user interface 2845 can be facilitated by communications network(s) 2820 and/or a server 2830 configured to communicate with the user interface 2810 and the second user interface 2845 through the communications network(s) 2820.

Communication between the user interface 2810 and the second user interface 2845 can enable applications of the exosuit 2800 and second exosuit 2840. In some examples, actions of the exosuit 2800 and second flexible exosuit 2840 and/or of wearers of the exosuit 2800 and second exosuit 2840 can be coordinated. For example, the exosuit 2800 and second exosuit 2840 can be operated to coordinate the lifting of a heavy object by the wearers. The timing of the lift, and the degree of support provided by each of the wearers and/or the exosuit 2800 and second exosuit 2840 can be controlled to increase the stability with which the heavy object was carried, to reduce the risk of injury of the wearers, or according to some other consideration. Coordination of actions of the exosuit 2800 and second exosuit 2840 and/or of wearers thereof can include applying coordinated (in time, amplitude, or other properties) forces and/or torques to the wearers and/or elements of the environment of the wearers and/or applying haptic feedback (though actuators of the exosuits 2800, 2840, through dedicated haptic feedback elements, or through other methods) to the wearers to guide the wearers toward acting in a coordinated manner.

Coordinated operation of the exosuit 2800 and second exosuit 2840 can be implemented in a variety of ways. In some examples, one exosuit (and the wearer thereof) can act as a master, providing commands or other information to the other exosuit such that operations of the exosuit 2800, 2840 are coordinated. For example, the exosuit 2800, 2840 can be operated to enable the wearers to dance (or to engage in some other athletic activity) in a coordinated manner. One of the exosuits can act as the 'lead', transmitting timing or other information about the actions performed by the 'lead' wearer to the other exosuit, enabling coordinated dancing motions to be executed by the other wearer. In some examples, a first wearer of a first exosuit can act as a trainer, modeling motions or other physical activities that a second wearer of a second exosuit can learn to perform. The first exosuit can detect motions, torques, forces, or other physical activities executed by the first wearer and can send information related to the detected activities to the second exosuit. The second exosuit can then apply forces, torques, haptic feedback, or other information to the body of the second wearer to enable the second wearer to learn the motions or other physical activities modeled by the first wearer. In some examples, the server 2830 can send commands or other information to the exosuits 2800, 2840 to enable coordinated operation of the exosuits 2800, 2840.

The exosuit 2800 can be operated to transmit and/or record information about the actions of a wearer, the environment of the wearer, or other information about a wearer of the exosuit 2800. In some examples, kinematics related to motions and actions of the wearer can be recorded and/or sent to the server 2830. These data can be collected for medical, scientific, entertainment, social media, or other applications. The data can be used to operate a system. For example, the exosuit 2800 can be configured to transmit motions, forces, and/or torques generated by a user to a robotic system (e.g., a robotic arm, leg, torso, humanoid body, or some other robotic system) and the robotic system can be configured to mimic the activity of the wearer and/or to map the activity of the wearer into motions, forces, or torques of elements of the robotic system. In another example, the data can be used to operate a virtual avatar of the wearer, such that the motions of the avatar mirrored or were somehow related to the motions of the wearer. The virtual avatar can be instantiated in a virtual environment, presented to an individual or system with which the wearer is communicating, or configured and operated according to some other application.

Conversely, the exosuit 2800 can be operated to present haptic or other data to the wearer. In some examples, the actuators 2801 (e.g., twisted string actuators, exotendons) and/or haptic feedback elements (e.g., EPAM haptic elements) can be operated to apply and/or modulate forces applied to the body of the wearer to indicate mechanical or other information to the wearer. For example, the activation in a certain pattern of a haptic element of the exosuit 2800 disposed in a certain location of the exosuit 2800 can indicate that the wearer had received a call, email, or other communications. In another example, a robotic system can be operated using motions, forces, and/or torques generated by the wearer and transmitted to the robotic system by the exosuit 2800. Forces, moments, and other aspects of the environment and operation of the robotic system can be transmitted to the exosuit 2800 and presented (using actuators 2801 or other haptic feedback elements) to the wearer to enable the wearer to experience force-feedback or other haptic sensations related to the wearer's operation of the robotic system. In another example, haptic data presented to a wearer can be generated by a virtual environment, e.g., an environment containing an avatar of the wearer that is being operated based on motions or other data related to the wearer that is being detected by the exosuit 2800.

Note that the exosuit 2800 illustrated in FIG. 28 is only one example of a exosuit that can be operated by control electronics, software, or algorithms described herein. Control electronics, software, or algorithms as described herein can be configured to control flexible exosuits or other mechatronic and/or robotic system having more, fewer, or different actuators, sensors or other elements. Further, control electronics, software, or algorithms as described herein can be configured to control exosuits configured similarly to or differently from the illustrated exosuit 2800. Further, control electronics, software, or algorithms as described herein can be configured to control flexible exosuits having reconfigurable hardware (i.e., exosuits that are able to have actuators, sensors, or other elements added or removed) and/or to detect a current hardware configuration of the flexible exosuits using a variety of methods.

A controller of a exosuit and/or computer-readable programs executed by the controller can be configured to provide encapsulation of functions and/or components of the flexible exosuit. That is, some elements of the controller (e.g., subroutines, drivers, services, daemons, functions) can be configured to operate specific elements of the exosuit (e.g., a twisted string actuator, a haptic feedback element) and to allow other elements of the controller (e.g., other programs) to operate the specific elements and/or to provide abstracted access to the specific elements (e.g., to translate a command to orient an actuator in a commanded direction into a set of commands sufficient to orient the actuator in the commanded direction). This encapsulation can allow a variety of services, drivers, daemons, or other computer-readable programs to be developed for a variety of applications of a flexible exosuits. Further, by providing encapsulation of functions of a flexible exosuit in a generic, accessible manner (e.g., by specifying and implementing an application programming interface (API) or other interface standard), computer-readable programs can be created to interface with the generic, encapsulated functions such that the computer-readable programs can enable operating modes or functions for a variety of differently-configured exosuit, rather than for a single type or model of flexible exosuit. For example, a virtual avatar communications program can access information about the posture of a wearer of a flexible exosuit by accessing a standard exosuit API. Differently-configured exosuits can include different sensors, actuators, and other elements, but can provide posture information in the same format according to the API. Other functions and features of a flexible exosuit, or other robotic, exoskeletal, assistive, haptic, or other mechatronic system, can be encapsulated by APIs or according to some other standardized computer access and control interface scheme.

Figure 29:
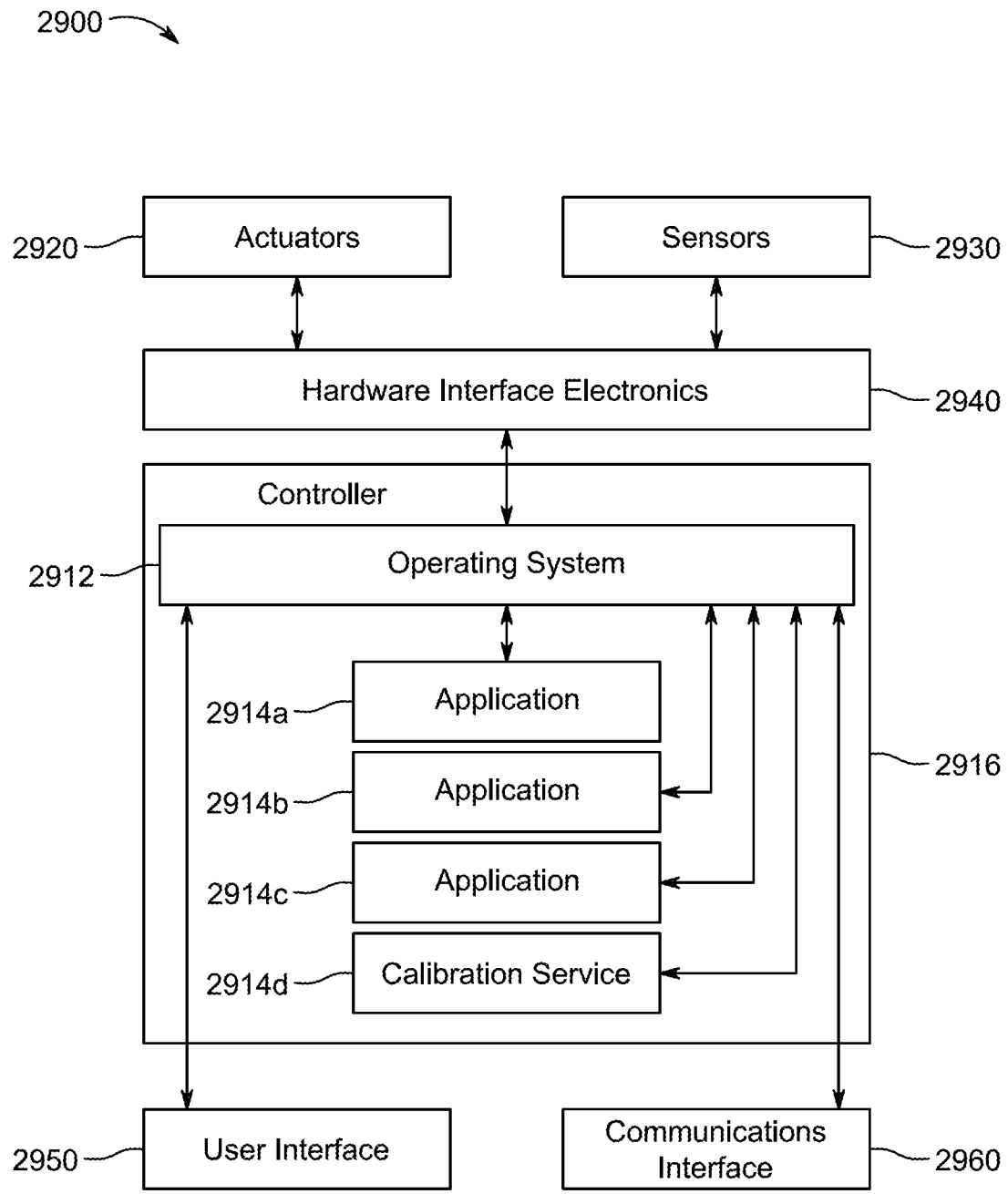
FIG. 29 is a schematic illustrating elements of an exosuit and a hierarchy of control or operating the exosuit according to an embodiment.

FIG. 29 is a schematic illustrating elements of a exosuit 2900 and a hierarchy of control or operating the exosuit 2900. The flexible exosuit includes actuators 2920 and sensors 2930 configured to apply forces and/or torques to and detect one or more properties of, respectively, the exosuit 2900, a wearer of the exosuit 2900, and/or the environment of the wearer. The exosuit 2900 additionally includes a controller 2910 configured to operate the actuators 2920 and sensors 2930 by using hardware interface electronics 2940. The hardware electronics interface 2940 includes electronics configured to interface signals from and to the controller 2910 with signals used to operate the actuators 2920 and sensors 2930. For example, the actuators 2920 can include exotendons, and the hardware interface electronics 2940 can include high-voltage generators, high-voltage switches, and high-voltage capacitance meters to clutch and un-clutch the exotendons and to report the length of the exotendons. The hardware interface electronics 2940 can include voltage regulators, high voltage generators, amplifiers, current detectors, encoders, magnetometers, switches, controlled-current sources, DACs, ADCs, feedback controllers, brushless motor controllers, or other electronic and mechatronic elements.

The controller 2910 additionally operates a user interface 2950 that is configured to present information to a user and/or wearer of the exosuit 2900 and a communications interface 2960 that is configured to facilitate the transfer of information between the controller 2910 and some other system (e.g., by transmitting a wireless signal). Additionally or alternatively, the user interface 2950 can be part of a separate system that is configured to transmit and receive user interface information to/from the controller 2910 using the communications interface 2960 (e.g., the user interface 2950 can be part of a cellphone).

The controller 2910 is configured to execute computer-readable programs describing functions of the flexible exosuit 2912. Among the computer-readable programs executed by the controller 2910 are an operating system 2912, applications 2914 $a$, 2914 $b$, 2914 $c$, and a calibration service 2916. The operating system 2912 manages hardware resources of the controller 2910 (e.g., I/O ports, registers, timers, interrupts, peripherals, memory management units, serial and/or parallel communications units) and, by extension, manages the hardware resources of the exosuit 2900. The operating system 2912 is the only computer-readable program executed by the controller 2910 that has direct access to the hardware interface electronics 2940 and, by extension, the actuators 2920 and sensors 2930 of the exosuit 2900.

The applications 2914 $a$, 2914 $b$, 2914 are computer-readable programs that describe some function, functions, operating mode, or operating modes of the exosuit 2900. For example, application 2914 $a$ can describe a process for transmitting information about the wearer's posture to update a virtual avatar of the wearer that includes accessing information on a wearer's posture from the operating system 2912, maintaining communications with a remote system using the communications interface 2960, formatting the posture information, and sending the posture information to the remote system. The calibration service 2916 is a computer-readable program describing processes to store parameters describing properties of wearers, actuators 2920, and/or or sensors 2930 of the exosuit 2900, to update those parameters based on operation of the actuators 2920, and/or sensors 2930 when a wearer is using the exosuit 2900, to make the parameters available to the operating system 2912 and/or applications 2914 $a$, 2914 $b$, 2914 $c$, and other functions relating to the parameters. Note that applications 2914 $a$, 2914 $b$, 2914 and calibration service 2916 are intended as examples of computer-readable programs that can be run by the operating system 2912 of the controller 2910 to enable functions or operating modes of a exosuit 2900.

The operating system 2912 can provide for low-level control and maintenance of the hardware (e.g., 2920, 2930, 2940). In some examples, the operating system 2912 and/or hardware interface electronics 1540 can detect information about the exosuit 2900, the wearer, and/or the wearer's environment from one or more sensors 2930 at a constant specified rate. The operating system 2912 can generate an estimate of one or more states or properties of the exosuit 2900 or components thereof using the detected information. The operating system 2912 can update the generated estimate at the same rate as the constant specified rate or at a lower rate. The generated estimate can be generated from the detected information using a filter to remove noise, generate an estimate of an indirectly-detected property, or according to some other application. For example, the operating system 2912 can generate the estimate from the detected information using a Kalman filter to remove noise and to generate an estimate of a single directly or indirectly measured property of the exosuit 2900, the wearer, and/or the wearer's environment using more than one sensor. In some examples, the operating system can determine information about the wearer and/or exosuit 2900 based on detected information from multiple points in time. For example, the operating system 2900 can determine an eversion stretch and dorsiflexion stretch.

In some examples, the operating system 2912 and/or hardware interface electronics 2940 can operate and/or provide services related to operation of the actuators 2920. That is, in case where operation of the actuators 2920 requires the generation of control signals over a period of time, knowledge about a state or states of the actuators 2920, or other considerations, the operating system 2912 and/or hardware interface electronics 2940 can translate simple commands to operate the actuators 2920 (e.g., a command to generate a specified level of force using a twisted string actuator (TSA) of the actuators 2920) into the complex and/or state-based commands to the hardware interface electronics 2940 and/or actuators 2920 necessary to effect the simple command (e.g., a sequence of currents applied to windings of a motor of a TSA, based on a starting position of a rotor determined and stored by the operating system 2910, a relative position of the motor detected using an encoder, and a force generated by the TSA detected using a load cell).

In some examples, the operating system 2912 can further encapsulate the operation of the exosuit 2900 by translating a system-level simple command (e.g., a commanded level of force tension applied to the footplate) into commands for multiple actuators, according to the configuration of the exosuit 2900. This encapsulation can enable the creation of general-purpose applications that can effect a function of an exosuit (e.g., allowing a wearer of the exosuit to stretch his foot) without being configured to operate a specific model or type of exosuit (e.g., by being configured to generate a simple force production profile that the operating system 2912 and hardware interface electronics 2940 can translate into actuator commands sufficient to cause the actuators 2920 to apply the commanded force production profile to the footplate).

The operating system 2912 can act as a standard, multi-purpose platform to enable the use of a variety of exosuits having a variety of different hardware configurations to enable a variety of mechatronic, biomedical, human interface, training, rehabilitative, communications, and other applications. The operating system 2912 can make sensors 2930, actuators 2920, or other elements or functions of the exosuit 2900 available to remote systems in communication with the exosuit 2900 (e.g., using the communications interface 2960) and/or a variety of applications, daemons, services, or other computer-readable programs being executed by operating system 2912. The operating system 2912 can make the actuators, sensors, or other elements or functions available in a standard way (e.g., through an API, communications protocol, or other programmatic interface) such that applications, daemons, services, or other computer-readable programs can be created to be installed on, executed by, and operated to enable functions or operating modes of a variety of flexible exosuits having a variety of different configurations. The API, communications protocol, or other programmatic interface made available by the operating system 2912 can encapsulate, translate, or otherwise abstract the operation of the exosuit 2900 to enable the creation of such computer-readable programs that are able to operate to enable functions of a wide variety of differently-configured flexible exosuits.

Additionally or alternatively, the operating system 2912 can be configured to operate a modular flexible exosuit system (i.e., a flexible exosuit system wherein actuators, sensors, or other elements can be added or subtracted from a flexible exosuit to enable operating modes or functions of the flexible exosuit). In some examples, the operating system 2912 can determine the hardware configuration of the exosuit 2900 dynamically and can adjust the operation of the exosuit 2900 relative to the determined current hardware configuration of the exosuit 2900. This operation can be performed in a way that was 'invisible' to computer-readable programs (e.g., 2914 *a*, 2914 *b*, 2914 *c*) accessing the functionality of the exosuit 2900 through a standardized programmatic interface presented by the operating system 2912. For example, the computer-readable program can indicate to the operating system 2912, through the standardized programmatic interface, that a specified level of torque was to be applied to an ankle of a wearer of the exosuit 2900. The operating system 2912 can responsively determine a pattern of operation of the actuators 2920, based on the determined hardware configuration of the exosuit 2900, sufficient to apply the specified level of torque to the ankle of the wearer.

In some examples, the operating system 2912 and/or hardware interface electronics 2940 can operate the actuators 2920 to ensure that the exosuit 2900 does not operate to directly cause the wearer to be injured and/or elements of the exosuit 2900 to be damaged. In some examples, this can include not operating the actuators 2920 to apply forces and/or torques to the body of the wearer that exceeded some maximum threshold. This can be implemented as a watchdog process or some other computer-readable program that can be configured (when executed by the controller 2910) to monitor the forces being applied by the actuators 2920 (e.g., by monitoring commands sent to the actuators 2920 and/or monitoring measurements of forces or other properties detected using the sensors 2930) and to disable and/or change the operation of the actuators 2920 to prevent injury of the wearer. Additionally or alternatively, the hardware interface electronics 2940 can be configured to include circuitry to prevent excessive forces and/or torques from being applied to the wearer (e.g., by channeling to a comparator the output of a load cell that is configured to measure the force generated by a TSA, and configuring the comparator to cut the power to the motor of the TSA when the force exceeded a specified level).

In some examples, operating the actuators 2920 to ensure that the exosuit 2900 does not damage itself can include a watchdog process or circuitry configured to prevent over-current, over-load, over-rotation, or other conditions from occurring that can result in damage to elements of the exosuit 2900. For example, the hardware interface electronics 2940 can include a metal oxide varistor, breaker, shunt diode, or other element configured to limit the voltage and/or current applied to a winding of a motor.

Note that the above functions described as being enabled by the operating system 2912 can additionally or alternatively be implemented by applications 2914 *a*, 2914 *b*, 2914 *c*, services, drivers, daemons, or other computer-readable programs executed by the controller 2900. The applications, drivers, services, daemons, or other computer-readable programs can have special security privileges or other properties to facilitate their use to enable the above functions.

The operating system 2912 can encapsulate the functions of the hardware interface electronics 2940, actuators 2920, and sensors 2930 for use by other computer-readable programs (e.g., applications 2914 *a*, 2914 *b*, 2914 *c*, calibration service 2916), by the user (through the user interface 2950), and/or by some other system (i.e., a system configured to communicate with the controller 2910 through the communications interface 2960). The encapsulation of functions of the exosuit 2900 can take the form of application programming interfaces (APIs), i.e., sets of function calls and procedures that an application running on the controller 2910 can use to access the functionality of elements of the exosuit 2900. In some examples, the operating system 2912 can make available a standard 'exosuit API' to applications being executed by the controller 2910. The 'exosuit API' can enable applications 2914 *a*, 2914 *b*, 2914 *c* to access functions of the exosuit 2900 without requiring those applications 2914 *a*, 2914 *b*, 2914 *c* to be configured to generate whatever complex, time-dependent signals are necessary to operate elements of the exosuit 2900 (e.g., actuators 2920, sensors 2930).

The 'exosuit API' can allow applications 2914 a, 2914 b, 2914 c to send simple commands to the operating system 2912 (e.g., 'begin storing mechanical energy from the ankle of the wearer when the foot of the wearer contacts the ground') in such that the operating system 2912 can interpret those commands and generate the command signals to the hardware interface electronics 2940 or other elements of the exosuit 2900 that are sufficient to effect the simple commands generated by the applications 2914 a, 2914 b, 2914 c (e.g., determining whether the foot of the wearer has contacted the ground based on information detected by the sensors 2930, responsively applying high voltage to an exotendon that crosses the user's ankle).

The 'exosuit API' can be an industry standard (e.g., an ISO standard), a proprietary standard, an open-source standard, or otherwise made available to individuals that can then produce applications for exosuits. The 'exosuit API' can allow applications, drivers, services, daemons, or other computer-readable programs to be created that are able to operate a variety of different types and configurations of exosuits by being configured to interface with the standard 'exosuit API' that is implemented by the variety of different types and configurations of exosuits. Additionally or alternatively, the 'exosuit API' can provide a standard encapsulation of individual exosuit-specific actuators (i.e., actuators that apply forces to specific body segments, where differently-configured exosuits may not include an actuator that applies forces to the same specific body segments) and can provide a standard interface for accessing information on the configuration of whatever exosuit is providing the 'exosuit API'. An application or other program that accesses the 'exosuit API' can access data about the configuration of the exosuit (e.g., locations and forces between body segments generated by actuators, specifications of actuators, locations and specifications of sensors) and can generate simple commands for individual actuators (e.g., generate a force of 30 newtons for 50 milliseconds) based on a model of the exosuit generated by the application and based on the information on the accessed data about the configuration of the exosuit. Additional or alternate functionality can be encapsulated by an 'exosuit API' according to an application.

Applications 2914 a, 2914 b, 2914 c can individually enable all or parts of the functions and operating modes of a flexible exosuit described herein. For example, an application can enable haptic control of a robotic system by transmitting postures, forces, torques, and other information about the activity of a wearer of the exosuit 2900 and by translating received forces and torques from the robotic system into haptic feedback applied to the wearer (i.e., forces and torques applied to the body of the wearer by actuators 2920 and/or haptic feedback elements). In another example, an application can enable a wearer to locomote more efficiently by submitting commands to and receiving data from the operating system 2912 (e.g., through an API) such that actuators 2920 of the exosuit 2900 assist the movement of the user, extract negative work from phases of the wearer's locomotion and inject the stored work to other phases of the wearer's locomotion, or other methods of operating the exosuit 2900. Applications can be installed on the controller 2910 and/or on a computer-readable storage medium included in the exosuit 2900 by a variety of methods. Applications can be installed from a removable computer-readable storage medium or from a system in communication with the controller 2910 through the communications interface 2960. In some examples, the applications can be installed from a web site, a repository of compiled or un-compiled programs on the Internet, an online store (e.g., Google Play, iTunes App Store), or some other source. Further, functions of the applications can be contingent upon the controller 2910 being in continuous or periodic communication with a remote system (e.g., to receive updates, authenticate the application, to provide information about current environmental conditions).

The exosuit 2900 illustrated in FIG. 29 is intended as an illustrative example. Other configurations of flexible exosuits and of operating systems, kernels, applications, drivers, services, daemons, or other computer-readable programs are anticipated. For example, an operating system configured to operate a exosuit can include a real-time operating system component configured to generate low-level commands to operate elements of the exosuit and a non-real-time component to enable less time-sensitive functions, like a clock on a user interface, updating computer-readable programs stored in the exosuit, or other functions. A exosuit can include more than one controller; further, some of those controllers can be configured to execute real-time applications, operating systems, drivers, or other computer-readable programs (e.g., those controllers were configured to have very short interrupt servicing routines, very fast thread switching, or other properties and functions relating to latency-sensitive computations) while other controllers are configured to enable less time-sensitive functions of a flexible exosuit. Additional configurations and operating modes of a exosuit are anticipated. Further, control systems configured as described herein can additionally or alternatively be configured to enable the operation of devices and systems other than exosuit; for example, control systems as described herein can be configured to operate robots, rigid exosuits or exoskeletons, assistive devices, prosthetics, or other mechatronic devices.

Control of actuators of a exosuit can be implemented in a variety of ways according to a variety of control schemes. Generally, one or more hardware and/or software controllers can receive information about the state of the flexible exosuit, a wearer of the exosuit, and/or the environment of the exosuit from sensors disposed on or within the exosuit and/or a remote system in communication with the exosuit. The one or more hardware and/or software controllers can then generate a control output that can be executed by actuators of the exosuit to effect a commanded state of the exosuit and/or to enable some other application. One or more software controllers can be implemented as part of an operating system, kernel, driver, application, service, daemon, or other computer-readable program executed by a processor included in the exosuit.

In some embodiments, a powered assistive exosuit intended primarily for assistive functions can also be adapted to perform exosuit functions. In one embodiment, an assistive exosuit similar to the embodiments described in U.S. Patent Application Publication No. 2018/0056104, titled "Systems and Methods for Assistive Exosuit System," that is used for assistive functions may be adapted to perform exosuit functions. Embodiments of such an assistive exosuit typically include FLAs approximating muscle groups such as hip flexors, gluteal/hip extensors, spinal extensors, or abdominal muscles. In the assistive modes of these exosuits, these FLAs provide assistance for activities such as moving between standing and seated positions, walking, and postural stability. Actuation of specific FLAs within such an exosuit system may also provide stretching assistance. Typically, activation of one or more FLAs approximating a muscle group can stretch the antagonist muscles. For example, activation of one or more FLAs approximating the abdominal muscles might stretch the spinal extensors, or activation of one or more FLAs approximating gluteal/hip extensor muscles can stretch the hip flexors. The exosuit may be adapted to detect when the wearer is ready to initiate a stretch and perform an automated stretching regimen; or the wearer may indicate to the suit to initiate a stretching regimen.

It can be appreciated that assistive exosuits may have multiple applications. Assistive exosuits may be prescribed for medical applications. These may include therapeutic applications, such as assistance with exercise or stretching regimens for rehabilitation, disease mitigation or other therapeutic purposes. Mobility-assistance devices such as wheelchairs, walkers, crutches and scooters are often prescribed for individuals with mobility impairments. Likewise, an assistive exosuit may be prescribed for mobility assistance for patients with mobility impairments. Compared with mobility assistance devices such as wheelchairs, walkers, crutches and scooters, an assistive exosuit may be less bulky, more visually appealing, and conform with activities of daily living such as riding in vehicles, attending community or social functions, using the toilet, and common household activities.

An assistive exosuit may additionally function as primary apparel, fashion items or accessories. The exosuit may be stylized for desired visual appearance. The stylized design may reinforce visual perception of the assistance that the exosuit is intended to provide. For example, an assistive exosuit intended to assist with torso and upper body activities may present a visual appearance of a muscular torso and upper body. Alternatively, the stylized design may be intended to mask or camouflage the functionality of the assistive exosuit through design of the base layer, electro/mechanical integration or other design factors.

Similarly to assistive exosuits intended for medically prescribed mobility assistance, assistive exosuits may be developed and utilized for non-medical mobility assistance, performance enhancement and support. For many, independent aging is associated with greater quality of life, however activities may become more limited with time due to normal aging processes. An assistive exosuit may enable aging individuals living independently to electively enhance their abilities and activities. For example, gait or walking assistance could enable individuals to maintain routines such as social walking or golf. Postural assistance may render social situations more comfortable, with less fatigue. Assistance with transitioning between seated and standing positions may reduce fatigue, increase confidence, and reduce the risk of falls. These types of assistance, while not explicitly medical in nature, may enable more fulfilling, independent living during aging processes.

Athletic applications for an assistive exosuit are also envisioned. In one example, an exosuit may be optimized to assist with a particular activity, such as cycling. In the cycling example, FLAs approximating gluteal or hip extensor muscles may be integrated into bicycle clothing, providing assistance with pedaling. The assistance could be varied based on terrain, fatigue level or strength of the wearer, or other factors. The assistance provided may enable increased performance, injury avoidance, or maintenance of performance in the case of injury or aging. It can be appreciated that assistive exosuits could be optimized to assist with the demands of other sports such as running, jumping, swimming, skiing, or other activities. An athletic assistive exosuit may also be optimized for training in a particular sport or activity. Assistive exosuits may guide the wearer in proper form or technique, such as a golf swing, running stride, skiing form, swimming stroke, or other components of sports or activities. Assistive exosuits may also provide resistance for strength or endurance training. The provided resistance may be according to a regimen, such as high intensity intervals.

Assistive exosuit systems as described above may also be used in gaming applications. Motions of the wearer, detected by the suit, may be incorporated as a game controller system. For example, the suit may sense wearer's motions that simulate running, jumping, throwing, dancing, fighting, or other motions appropriate to a particular game. The suit may provide haptic feedback to the wearer, including resistance or assistance with the motions performed or other haptic feedback to the wearer.

Assistive exosuits as described above may be used for military or first responder applications. Military and first responder personnel are often to be required to perform arduous work where safety or even life may be at stake. An assistive exosuit may provide additional strength or endurance as required for these occupations. An assistive exosuit may connect to one or more communication networks to provide communication services for the wearer, as well as remote monitoring of the suit or wearer.

Assistive exosuits as described above may be used for industrial or occupational safety applications. Exosuits may provide more strength or endurance for specific physical tasks such as lifting or carrying or repetitive tasks such as assembly line work. By providing physical assistance, assistive exosuits may also help avoid or prevent occupational injury due overexertion or repetitive stress.

Assistive exosuits as described above may also be configured as home accessories. Home accessory assistive exosuits may assist with household tasks such as cleaning or yard work, or may be used for recreational or exercise purposes. The communication capabilities of an assistive exosuit may connect to a home network for communication, entertainment or safety monitoring purposes.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art can appreciate that the conception, upon which this disclosure is based, may readily be utilized as a basis for the designing of other structures, systems, methods and media for carrying out the several purposes of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

What is claimed is:
1. An exosuit comprising:
 a core support grip that is positioned around a core of a human body, the core support grip comprising:

first and second front main stays positioned on an anterior side of the human body, each the first and second main stays comprising a rigid portion and a plurality of ports; and
first and second back main stays positioned on a posterior side of the human body, each of the first and second back main stays comprising a rigid portion, a port, and an anchor point; and
a tension system connected to the core support grip, the tension system comprising:
adjustment member;
a first cord that is routed from the adjustment member through the plurality of ports associated with the first front main stay, the port associated with the first back main stay, and secured to the anchor point associated with the with the first back main stay; and
a second cord that is routed from the adjustment member through the plurality of ports associated with the second front main stay, the port associated with the second back main stay, and secured to the anchor point associated with the with the second back main stay;
wherein the adjustment member is operative to adjust tension applied by the first and second cords to increase or decrease forces applied to the core.

2. The exosuit of claim 1, wherein the first cord crosses itself between the first front main stay and the first back main stay, and wherein the second cord crosses itself between the second front main stay and the second back main stay.

3. The exosuit of claim 1, wherein the first and second front main stays each further comprise an attachment point for a flexor power layer, and wherein the first and second back main stays each further comprise an attachment point for an extensor power layer.

4. The exosuit of claim 1, wherein the core support grip further comprises a plurality of side stays positioned on sides of the human body between the anterior and posterior sides.

5. The exosuit of claim 4, wherein the tension system interface with the plurality of side stays to exert forces to the core.

6. The exosuit of claim 1, wherein the core support member further comprises:
first and second front sub-stays, wherein the first and second front main stays are secured above respective first and second front sub-stays; and
a back sub-stay, wherein the first and second back main stays are secured above the back sub-stay.

7. The exosuit of claim 6, wherein each of the first and second front main stays, the first and second back main stays, the first and second front sub-stays, and the back sub-stay is constructed from a stack of layers comprising at least one textile layer and one adhesive layer.

8. The exosuit of claim 6, further comprising a base layer having interior and exterior sides and configured to be in direct contact with the human body, wherein the first and second front main stays and the first and second back main stays interface with the exterior side, and wherein the first and second front sub-stays and the back sub-stay interface with the interior side.

9. The exosuit of claim 1, wherein the adjustment member comprises a manually operated adjustment member or a flexible linear actuator.

10. An exosuit comprising:
a core support grip that is positioned around a core of a human body, the core support grip comprising:
first and second front panels positioned on an anterior side of the human body, each of the first and second front panels comprising a vertical stay; and
a back panel positioned on a posterior side of the human body, the back panel comprising a plurality of vertical stays; and
a tension system connected to the core support grip and operative to increase or decrease pressure applied to the core by the cores support grip.

11. The exosuit of claim 10, wherein the vertical stay associated with the first front panel comprises:
a first plurality of anchor points; and
a first tension interface member;
wherein the vertical stay associated with the second front panel comprises:
a second plurality of anchor points; and
a second tension interface member;
wherein a first vertical stay of the plurality of vertical stays associated with the back panel comprises a third plurality of anchor points; and
wherein a second vertical stay of the plurality of vertical stays associated with the back panel comprises a fourth plurality of anchor points.

12. The exosuit of claim 11, further comprising:
a first plurality of cross bands that are coupled to the first and third plurality of anchor points; and
a second plurality of cross bands that are coupled to the second and fourth plurality of anchor points.

13. The exosuit of claim 12, wherein the first plurality of cross bands cross each other, and wherein the second plurality of cross bands cross each other, and wherein each of the first and second cross bands are adjustable.

14. The exosuit of claim 11, wherein the tension system comprises:
a motor;
a twisted string coupled to the motor;
a first belt segment coupled to the first tension interface member;
a second segment coupled to the second tension interface member; and
wherein then the twisted sting is shortened in length, forces are applied to the body via the core support grip.

15. The exosuit of claim 10, further comprising:
a first shoulder strap coupled to the first and second front panels and the back panel; and
a second shoulder strap coupled to the first and second front panels and the back panel.

16. The exosuit of claim 10, further comprising:
a base layer; and
a plurality of side stays that are secured to the base layer and positioned on sides of the human body between the anterior and posterior sides.

17. The exosuit of claim 10, wherein the first front panel is constructed from a plurality of non-stretch fabrics that sandwich the vertical stay associated with the first front panel, wherein the second front panel is constructed from a plurality of non-stretch fabrics that sandwich the vertical stay associated with the second front panel, wherein the back panel is constructed from a plurality of non-stretch fabrics that sandwich the plurality of vertical stays associated with the back panel.

18. The exosuit of claim 10, wherein each of the verticals stays associated with the first and second front panels and the back panel is constructed from a rigid material designed to distribute force loads across the core.

19. The exosuit of claim 10, wherein each of the verticals stays associated with the first and second front panels has a smaller vertical dimension than the plurality of vertical stays associated with the back panel.

20. The exosuit of claim 10, wherein each of the verticals stays associated with the first and second front panels comprises anchor points for flexor power layer segment, and wherein a subset of the plurality of vertical stays associated with the back panel comprises anchor points for extensor power layer segments.

* * * * *